US008389518B2

(12) United States Patent
Page et al.

(10) Patent No.: US 8,389,518 B2
(45) Date of Patent: Mar. 5, 2013

(54) PYRAZOLO PYRIDINE DERIVATIVES AS NADPH OXIDASE INHIBITORS

(75) Inventors: Patrick Page, Savonni (FR); Mike Orchard, Oxon (GB); Laetitia Fioraso-Cartier, Fillinges (FR); Bianca Mottironi, Geneva (CH)

(73) Assignee: Genkyotex SA, Plan-les-Ouates (CH)

( * ) Notice: Subject to any disclaimer, the term of this patent is extended or adjusted under 35 U.S.C. 154(b) by 49 days.

(21) Appl. No.: 12/532,336

(22) PCT Filed: Mar. 20, 2008

(86) PCT No.: PCT/EP2008/053390
§ 371 (c)(1),
(2), (4) Date: Sep. 21, 2009

(87) PCT Pub. No.: WO2008/113856
PCT Pub. Date: Sep. 25, 2008

(65) Prior Publication Data
US 2010/0048560 A1 Feb. 25, 2010

Related U.S. Application Data

(60) Provisional application No. 60/896,284, filed on Mar. 22, 2007.

(30) Foreign Application Priority Data

Jun. 4, 2007 (EP) .................................... 07109555

(51) Int. Cl.
| A61K 31/5377 | (2006.01) |
| A61K 31/497 | (2006.01) |
| A61K 31/44 | (2006.01) |
| C07D 413/14 | (2006.01) |
| C07D 401/14 | (2006.01) |
| C07D 471/04 | (2006.01) |

(52) U.S. Cl. ................ 514/234.2; 514/253.04; 514/303; 544/127; 544/362; 546/119
(58) Field of Classification Search .............. 514/234.2, 514/253.04, 303; 544/127, 362; 546/119
See application file for complete search history.

(56) References Cited

U.S. PATENT DOCUMENTS

| 3,931,407 | A | 1/1976 | Allen et al. |
| 4,909,827 | A | 3/1990 | Gehring et al. |
| 5,869,516 | A | 2/1999 | Arlt et al. |
| 6,624,309 | B1 | 9/2003 | Lloyd et al. |
| 2009/0099179 | A1 | 4/2009 | Klein et al. |
| 2010/0120749 | A1 | 5/2010 | Page et al. |
| 2011/0172266 | A1 | 7/2011 | Page et al. |
| 2011/0178081 | A1 | 7/2011 | Page et al. |
| 2011/0178082 | A1 | 7/2011 | Page et al. |
| 2011/0269757 | A1 | 11/2011 | Page et al. |

FOREIGN PATENT DOCUMENTS

| DE | 102005048897 | 4/2007 |
| EP | 0274642 A | 7/1988 |
| EP | 1505068 | 2/2005 |
| EP | 2002835 A | 12/2008 |
| WO | WO 2004/005267 | 1/2004 |
| WO | WO 2005/080378 | 9/2005 |
| WO | WO 2006/041874 | 4/2006 |
| WO | WO 2008/116926 | 10/2008 |
| WO | WO 2010/035217 | 4/2010 |
| WO | WO 2010/035219 | 4/2010 |
| WO | WO 2010/035220 | 4/2010 |
| WO | WO 2010/035221 | 4/2010 |

OTHER PUBLICATIONS

Lala et al., Role of nitric oxide in tumor progression: Lessons from experimental tumors, Cancer and Metastasis Reviews (1998),17, 91-106.*
Golub et al., Molecular Classification of Cancer: Class Discovery and Class Prediction by Gene Expression Monitoring, Science (1999), vol. 286, 531-537.*
Wolff et al., Burger's Medicinal Chemistry and Drug Discovery, 1994, Wiley-Interscience, Fifth Edition, vol. I: Principles and Practice, pp. 975-977.*
"Derivative." Merriam-Webster Online Dictionary. 2010. Merriam-Webster Online. Accessed Apr. 20, 2010. <http://merriam-webster.com/dictionary/derivative>.*
Cancer [online], [retrieved on Jul. 6, 2007] Retrieved from the Internet, URL: http://www.nlm.nih.gov/medlineplus/cancer.html.*
Junker, L. M., and Clardy, J., "High-Throughput Screens for Small-Molecule Inhibitors of *Pseudomonas aeruginosa* Biofilm Development", Antimicrobial Agents and Chemotherapy, Oct. 2007, vol. 51, No. 10, pp. 3582-3590.
Djordjevic, T., et al., "Human Urotensin II is a Novel Activator of NADPH Oxidase in Human Pulmonary Artery Smooth Muscle Cells," Arterioscler. Thromb. Vasc. Biol. 2005; 25; 519-525.
Hua, C., et al., "The vascular NAD(P)H oxidases as therapeutic targets in cardiovascular diseases", TRENDS in Pharmacological Sciences, vol. 24, No. 9, Sep. 2003.
Saxena, U, et al., "New approaches for treatment of diabetic nephropathy: the endothelium as a target for drug discovery", Expert Opin. Ther. Targets (2001) 5(5):539-545.
Dornow, A. et al., "Darstellung und Umsetzung einiger substituierter 3-Nitro-pyridine", 1966, Chem. Ber., 99, 244-253.
Ellis, E. A., et al., "Increased $H_2O_2$ Vascular Endothelial Growth Factor and Receptors in the Retina of the BBZ/WOR Diabetic RAT", Free Radical Biology & Medicine, vol. 28, No. 1, pp. 91-101, 2000.
Thabut, G., et al., "Tumor Necrosis Factor-α Increases Airway Smooth Muscle Oxidants Production through a NADPH Oxidase-like System to Enhance Myosin Light Chain Phosphorylation and Contractility", Journal of Biological Chemistry, vol. 227, No. 25, Issue of Jun. 21, 2002, pp. 22814-22821.

(Continued)

*Primary Examiner* — Kristin Bianchi
(74) *Attorney, Agent, or Firm* — Saliwanchik, Lloyd & Eisenschenk

(57) ABSTRACT

The present invention is related to pyrazolo pyridine derivatives of Formula (I), pharmaceutical composition thereof and to their use for the treatment and/or prophylaxis of disorders or conditions related to Nicotinamide adenine dinucleotide phosphate oxidase (NADPH Oxidase).

35 Claims, No Drawings

OTHER PUBLICATIONS

Yang, S., et al., "Characterization of Interferon Gamma Receptors on Osteoclasts: Effect of Interferon Gamma on Osteoclastic Superoxide Generation", Jounal of Cellular Biochemistry 84:645-654, 2002.

Search Report and Written Opinion for PCT/EP2008/053390 issued by the European Patent Office on Jul. 21, 2008.

Banfi, B. et al. "NOX3, a Superoxide-generating NADPH Oxidase of the Inner Ear" *The Journal of Biological Chemistry*, Oct. 29, 2004, pp. 46065-46072, vol. 279, No. 44.

Laleu, B. et al. "First in Class, Potent, and Orally Bioavailable NADPH Oxidase Isoform 4 (Nox4) Inhibitors for the Treatment of Idiopathic Pulmonary Fibrosis" *J. Med. Chem.*, 2010, pp. 7715-7730, vol. 53.

Lambeth, J. D. et al. "NOX enzymes as novel targets for drug development" *Semin Immunopathol*, 2008, pp. 1-25.

Rao, P. V. et al. "Expression of nonphagocytic NADPH oxidase system in the ocular lens" *Molecular Vision*, 2004, pp. 112-121, vol. 10.

Vendrov, A. E. et al. "NADPH Oxidases Regulate CD44 and Hyaluronic Acid Expression in Thrombin-treated Vascular Smooth Muscle Cells and in Atherosclerosis" *The Journal of Biological Chemistry*, Aug. 20, 2010, pp. 26545-26557, vol. 285, No. 34.

Sedeek, M. et al. "Critical role of Nox4-based NADPH oxidase in glucose-induced oxidative stress in the kidney: implications in type 2 diabetic nephropathy" *Am. J. Physiol. Renal Physiol.*, 2010, pp. F1348-F1358, vol. 229.

Cai, H. et al. "The vascular NAD(P)H oxidases as therapeutic targets in cardiovascular diseases" *TRENDS in Pharmacological Sciences*, Sep. 2003, pp. 471-478, vol. 24, No. 9.

Nunomura, A. et al. "Oxidative Damage is the Earliest Event in Alzheimer Disease" *Journal of Neuropathology and Experimental Neurology*, Aug. 2001, pp. 759-767, vol. 60, No. 8.

Shi, Y. et al. "Increased NAD(P)H Oxidase and Reactive Oxygen Species in Coronary Arteries After Balloon Injury" *Arterioscler Thromb Vasc Biol.*, 2001, pp. 739-745, vol. 21.

Bedard, K. et al. "The NOX Family of ROS-Generating NADPH Oxidases: Physiology and Pathophysiology" *Physiological Reviews*, Jan. 2007, pp. 245-313, vol. 87.

Ferrara, N. et al. "Angiogenesis as a therapeutic target" *Nature*, Dec. 15, 2005, pp. 967-974, vol. 438.

Folkman, J. "Angiogenesis" *Annu. Rev. Med.*, 2006, pp. 1-18, vol. 57.

Griendling, K. K. et al. "NAD(P)H Oxidase: Role in Cardiovascular Biology and Disease" *Circulation Research*, 2000, pp. 494-501, vol. 86.

Ray, R. et al. "NADPH oxidase and endothelial cell function" *Clinical Science*, 2005, pp. 217-226, vol. 109.

Wu, D. et al. "NADPH oxidase mediates oxidative stress in the 1-methyl-4-phenyl-1,2,3,6-tetrahydropyridine model of Parkinson's disease" *PNAS*, May 13, 2003, pp. 6145-6150, vol. 100, No. 10.

Garrido-Urbani, S. et al. "Targeting Vascular NADPH Oxidase 1 Blocks Tumor Angiogenesis through a PPARα Mediated Mechanism" *PLoS ONE*, Feb. 2011, pp. 1-13, vol. 6, Issue 2.

Abdelrahman, M. et al. "Inhibitors of NADPH Oxidase Reduce the Organ Injury in Hemorrhagic Shock" *Shock*, 2005, pp. 107-114, vol. 23, No. 2.

Anantharam, V. et al. "Pharmacological inhibition of neuronal NADPH oxidase protects against 1-methyl-4-phenylpyridinium (MPP$^+$)-induced oxidative stress and apoptosis in mesencephalic dopaminergic neuronal cells" *Neuro Toxicology*, 2007, pp. 988-997, vol. 28.

Baker, M. A. et al. "Reactive oxygen species in spermatozoa: methods for monitoring and significance for the origins of genetic disease and infertility" *Reproductive Biology and Endorcinology*, 2005, pp. 1-9, vol. 3, No. 67.

Chen, P. et al. "Role of NADPH oxidase and ANG II in diabetes-induced retinal leukostasis" *Am. J. Physiol. Reul. Integr. Comp. Physiol.*, 2007, pp. R1619-R1629, vol. 293.

Cucoranu, I. et al. "NAD(P)H Oxidase 4 Mediates Transforming Growth Factor-b1-Induced Differentiation of Cardiac Fibroblasts Into Myofibroblasts" *Circulation Research*, 2005, pp. 900-907, vol. 97.

El Benna, J. et al. "NADPH Oxidase Priming and p47phox Phosphorylation in Neutrophils from Synovial Fluid of Patients with Rheumatoid Arthritis and Spondylarthropathy" *Inflammation*, Dec. 2002, pp. 273-278, vol. 26, No. 6.

Ellis E. A. et al. "Time Course of NADH Oxidase, Inducible Nitric Oxide Synthase and Peroxynitrite in Diabetic Retinopathy in the BBZ/WOR Rat" *Nitric Oxide: Biology and Chemistry*, 2002, pp. 295-304, vol. 6, No. 3.

Fukuyama, M. et al. "Overexpression of a novel superoxide-producing enzyme, NADPH oxidase 1, in adenoma and well differentiated adenocarcinoma of the human colon" *Cancer Letters*, 2005, pp. 97-104, vol. 221.

Gavazzi, G. et al. "NOX1 Deficiency Protects from Aortic Dissection in Response to Angiotensin II" *Hypertension*, 2007, pp. 189-196, vol. 50.

Gukovskaya, A. S. et al. "Neutrophils and NADPH Oxidase Mediate Intrapancreatic Trypsin Activation in Murine Experimental Acute Pancreatitis" *Gastroenterology*, 2002, pp. 974-984, vol. 122.

Hausmann, M. et al. "Subtractive screening reveals up-regulation of NADPH oxidase expression in Crohn's disease intestinal macrophages" *Clin. Exp. Immunol.*, 2001, pp. 48-55, vol. 125.

Hoidal, J. R. et al. "The Role of Endogenous NADPH Oxidases in Airway and Pulmonary Vascular Smooth Muscle Function" *Antioxidants & Redox Signaling*, 2003, pp. 751-758, vol. 5.

Inoguchi, T. et al. "NAD(P)H Oxidase Activation: A Potential Target Mechanism for Diabetic Vascular Complications, Progressive β-Cell Dysfunction and Metabolic Syndrome" *Current Drug Targets*, 2005, pp. 495-501, vol. 6.

Jin, L. et al. "NADPH oxidase: recent evidence for its role in erectile dysfunction" *Asian J. Androl.*, Jan. 2008, pp. 6-13, vol. 10.

Kawai, Y. et al. "Relationship of Intracellular Calcium and Oxygen Radicals to Cisplatin-Related Renal Cell Injury" *J. Pharmacol. Sci.*, 2006, pp. 65-72, vol. 100.

Klees, R. F. et al. "Apocynin Derivatives Interrupt Intracellular Signaling Resulting in Decreased Migration in Breast Cancer Cells" *Journal of Biomedicine and Biotechnology*, 2006, pp. 1-10, vol. 2006.

Krijnen, P. A. et al. "Increased Nox2 expression in human cardiomyocytes after acute myocardial infarction" *J. Clin. Pathol.*, 2003, pp. 194-199, vol. 56.

Lanone S. et al. "Bilirubin decreases NOS2 expression via inhibition of NAD(P)H oxidase: implications for protection against endotoxic shock in rats" *The FASEB Journal*, 2005, pp. 1-26.

Lee, N. K. et al. "A crucial role for reactive oxygen species in RANKL-induced osteoclast differentiation" *Blood*, 2005, pp. 852-859, vol. 106.

Liu, Y. et al. "Suppression of Microglial Inflammatory Activity by Myelin Phagocytosis: Role of p47-PHOX-Mediated Generation of Reactive Oxygen Species" *The Journal of Neuroscience*, Dec. 13, 2006, pp. 12904-12913, vol. 26, No. 50.

Nibali, L. et al. "NADPH oxidase (CYBA) and FcγR polymorphisms as risk factors for aggressive periodontitis" *J. Clin. Periodontol*, 2006, pp. 529-539, vol. 33.

Patel, C. et al. "Prolonged Reactive Oxygen Species Generation and Nuclear Factor-↓B Activation after a High-Fat, High-Carbohydrate Meal in the Obese" *The Journal of Clinical Endocrinology & Metabolism*, 2007, pp. 4476-4479, vol. 92, No. 111.

Patel, M. et al. "Activation of NADPH oxidase and extracellular superoxide production in seizure-induced hippocampal damage" *Journal of Neurochemistry*, 2005, pp. 123-131, vol. 92.

Puntambekar, P. et al. "Essential Role of Rac1/NADPH oxidase in nerve growth factor induction of TRPV1 expression" *Journal of Neurochemistry*, 2005, pp. 1689-1703, vol. 95.

Qian, L. et al. "Sinomenine, a natural dextrorotatory morphinan analog, is anti-inflammatory and neuroprotective through inhibition of microglial NADPH oxidase" *Journal of Neuroinflammation*, 2007, pp. 1-14, vol. 4, No. 23.

Ritsick, D. R. et al. "Spring brings breezes, wheezes, and pollen oxidases" *The Journal of Clinical Investigation*, Aug. 2005, vol. 115, No. 8.

Sato, K. et al. "In vivo lipid-derived free radical formation by NADPH oxidase in acute lung injury induced by lipopolysaccharide: a model for ARDS" *FASEB J.*, 2002, pp. 1713-1720, vol. 16.

Satoh, M. et al. "NAD(P)H oxidase and uncoupled nitric oxide synthase are major sources of glomerular superoxide in rats with experimental diabetic nephropathy" *Am. J. Physiol Renal Physiol*, 2005, pp. F1144-F1152, vol. 288.

Sharma, K. et al. "TGF-β impairs renal autoregulation via generation of ROS" *Am. J. Physiol Renal Physiol*, 2005, pp. F1069-F1079, vol. 288.

Sirker, A. et al. "Involvement of NADPH Oxidases in Cardiac Remodelling and Heart Failure" *Am. J. Nephrol*, 2007, pp. 649-660, vol. 27.

Sonta, T. et al. "Evidence for Contribution of Vascular NAD(P)H Oxidase to Increased Oxidative Stress in Animal Models of Diabetes and Obesity" *Free Radical Biology & Medicine*, 2004, pp. 115-123, vol. 37, No. 1.

Vaquero, V. C. et al. "Reactive Oxygen Species Produced by NAD(P)H Oxidase Inhibit Apoptosis in Pancreatic Cancer Cells" *The Journal of Biological Chemistry*, Aug. 13, 2004, pp. 34643-34654, vol. 279, No. 33.

Kerbel, R. S. "Tumor Angiogenesis" *N. Engl J Med*, May 8, 2008, pp. 2039-2049, vol. 358.

Hougee, S. et al. "Oral administration of the NADPH-oxidase inhibitor apocynin partially restores diminished cartilage proteoglycan synthesis and reduces inflammation in mice" *European Journal of Pharmacology*, 2006, pp. 264-269, vol. 531.

Chang, G. et al. "Specific Inhibition of NADP(H) Oxidase (NOX) Abrogates the Tumorigenic Phenotype of Renal Cancer Cells" Poster at Annual Meeting of the Society of Basic Urology, Nov. 2009, New Orleans, USA, p. 1.

Jain, V. K. et al. "NADPH Oxidase and Myeloperoxidase Activity in Psoriasis Leukocytes" *The Journal of Dermatology*, 1985, pp. 425-428, vol. 12.

Office Action dated Mar. 19, 2012 in U.S. Appl. No. 12/532,567.

Klein, C. et al. CAS:147:427219, 2007, Accession No. 2007:1146277, pp. 1-4.

Slade, R. et al. CAS:144:412361, 2006, Accession No. 2006:361235, pp. 1-4.

Chemcats Accession No. 2029347921, Jun. 13, 2008, XP-002514328, p. 1.

Written Opinion in International Application No. PCT/IB2009/054148, Oct. 12, 2009, pp. 1-8.

Office Action dated Apr. 17, 2012 in U.S. Appl. No. 13/120,436.

Written Opinion in International Application No. PCT/IB2009/054150, Oct. 13, 2010, pp. 1-11.

Written Opinion in International Application No. PCT/IB2009/054155, Nov. 6, 2010, pp. 1-7.

Chemcats Accession No. 2049339652, Jun. 13, 2008, XP-002514424, pp. 1-6.

Database CA [Online] Chemical Abstracts Service, Accession No. 2007:341007, 2007, XP-002558729, p. 1.

Database CA [Online] Chemical Abstracts Service, Accession No. 2004:14711, 2003, XP-002558730, pp. 1-2.

Written Opinion in International Application No. PCT/IB2009/054156, Mar. 3, 2010, pp. 1-10.

Office Action dated Apr. 16, 2012 in U.S. Appl. No. 13/120,438.

Written Opinion in International Application No. PCT/EP2008/053704, Jul. 7, 2008, pp. 1-7.

Ushio-Fukai, M. et al. "Reactive oxygen species and angiogenesis: NADPH oxidase as target for cancer therapy" *Cancer Letters*, 2008, pp. 37-52, vol. 266.

Written Opinion in International Application No. PCT/EP2008/053390, Jul. 21, 2008, pp. 1-6.

Sturrock, A. et al. "Nox4 mediates TGF-β1-induced retinoblastoma protein phosphorylation, proliferaton, and hypertrophy in human airway smooth muscle cells" *Am. J Physiol. Lung. Cell Mol. Physiol.*, 2007, pp. L1543-1555. vol. 292, No. 6.

Wu, D.-C. et al. "The inflammatory NADPh oxidase enzyme modulates motor neuron degeneration in amyotrophic lateral sclerosis mice" *PNAS*, Aug. 8, 2006, pp. 12132-12137, vol. 103, No. 32.

\* cited by examiner

PYRAZOLO PYRIDINE DERIVATIVES AS NADPH OXIDASE INHIBITORS

CROSS-REFERENCE TO RELATED APPLICATION

This application is a National Stage filing of PCT International Application Ser. No. PCT/EP2008/053390, filed Mar. 20, 2008, which claims the benefit of U.S. Provisional Application Ser. No. 60/896,284, filed Mar. 22, 2007, the disclosures each of which are expressly incorporated herein by reference.

FIELD OF THE INVENTION

The present invention relates to pyrazolo pyridine derivatives of Formula (I), pharmaceutical composition thereof and to their use for the preparation of a medicament for the treatment and/or prophylaxis of cardiovascular diseases, respiratory disorders, disorders affecting the metabolism, skin and/or bone diseases, neurodegenerative diseases, kidney diseases, reproduction disorders, inflammatory disorders and cancers. Specifically, the present invention is related to pyrazolo pyridine derivatives useful for the preparation of a pharmaceutical formulation for the modulation, notably the inhibition of the activity or function of the Nicotinamide adenine dinucleotide phosphate oxidase (NADPH Oxidase).

BACKGROUND OF THE INVENTION

NADPH oxidases (NOX) are proteins that transfer electrons across biological membranes. In general, the electron acceptor is oxygen and the product of the electron transfer reaction is superoxide. The biological function of NOX enzymes is therefore the generation of reactive oxygen species (ROS) from oxygen. Reactive oxygen species (ROS) are oxygen-derived small molecules, including oxygen radicals (super-oxide anion [$.O_2^-$], hydroxyl [HO.], peroxyl [ROO.], alkoxyl [RO.] and hydroperoxyl [HOO.]) and certain non-radicals that are either oxidizing agents and/or are easily converted into radicals. Nitrogen-containing oxidizing agents, such as nitric oxide are also called reactive nitrogen species (RNS). ROS generation is generally a cascade of reactions that starts with the production of superoxide. Superoxide rapidly dismutates to hydrogen peroxide either spontaneously, particularly at low pH or catalyzed by superoxide dismutase. Other elements in the cascade of ROS generation include the reaction of superoxide with nitric oxide to form peroxynitrite, the peroxidase-catalyzed formation of hypochlorous acid from hydrogen peroxide, and the iron-catalyzed Fenton reaction leading to the generation of hydroxyl radical.

ROS avidly interact with a large number of molecules including other small inorganic molecules as well as DNA, proteins, lipids, carbohydrates and nucleic acids. This initial reaction may generate a second radical, thus multiplying the potential damage. ROS are involved not only in cellular damage and killing of pathogens, but also in a large number of reversible regulatory processes in virtually all cells and tissues. However, despite the importance of ROS in the regulation of fundamental physiological processes, ROS production can also irreversibly destroy or alter the function of the target molecule. Consequently, ROS have been increasingly identified as major contributors to damage in biological organisms, so-called "oxidative stress".

During inflammation, NADPH oxidase is one of the most important sources of ROS production in vascular cells under inflammatory conditions (Thabut et al., 2002, *J. Biol. Chem.*, 277:22814-22821).

In the lung, tissues are constantly exposed to oxidants that are generated either endogenously by metabolic reactions (e.g. by mitochondrial respiration or activation of recruited inflammatory cells) or exogenously in the air (e.g. cigarette smoke or air pollutants). Further, the lungs, constantly exposed to high oxygen tensions as compared to other tissues, have a considerable surface area and blood supply and are particularly susceptible to injury mediated by ROS (Brigham, 1986, *Chest*, 89(6): 859-863). NADPH oxidase-dependent ROS generation has been described in pulmonary endothelial cells and smooth muscle cells. NADPH oxidase activation in response to stimuli has been thought to be involved in the development of respiratory disorders such as pulmonary hypertension and enhancement of pulmonary vasoconstriction (Djordjevic et al., 2005, *Arterioscler. Thromb. Vasc. Biol.*, 25, 519-525; Liua et al., 2004, *Am. J. Physiol. Lung, Cell. Mol. Physiol.*, 287: L111-118). Further, pulmonary fibrosis has been characterized by lung inflammation and excessive generation of ROS.

Osteoclasts, which are macrophage-like cells that play a crucial role in bone turn-over (e.g. bone resorption), generate ROS through NADPH oxidase-dependent mechanisms (Yang et al., 2002, *J. Cell. Chem.* 84, 645-654).

Diabetes is known to increase oxidative stress (e.g. increased generation of ROS by auto-oxidation of glucose) both in humans and animals and increased oxidative stress has been said to play an important role in the development of diabetic complications. It has been shown that increased peroxide localization and endothelial cell dysfunction in the central retina of diabetic rats coincides with the areas of NADPH oxidase activity in the retinal endothelial cells (Ellis et al., 2000, *Free Rad. Biol. Med.*, 28:91-101). Further, it has been suggested that controlling oxidative stress (ROS) in mitochondria and/or inflammation may be a beneficial approach for the treatment of diabetes (Pillarisetti et al., 2004, *Expert Opin. Ther. Targets*, 8(5):401-408).

ROS are also strongly implicated in the pathogenesis of atherosclerosis, cell proliferation, hypertension and reperfusion injury cardiovascular diseases in general (Cai et al., 2003, *Trends Pharmacol. Sci.*, 24:471-478). Not only is superoxide production, for example in the arterial wall, increased by all risk factors for atherosclerosis, but ROS also induce many "proatherogenic" in vitro cellular responses. An important consequence of the formation of ROS in vascular cells is the consumption of nitric oxide (NO). NO inhibits the development of vascular diseases, and loss of NO is important in the pathogenesis of cardiovascular diseases. The increase in NADPH oxidase activity in vascular wall after balloon injury has been reported (Shi et al., 2001, *Throm. Vasc. Biol.*, 2001, 21, 739-745)

It is believed that oxidative stress or free radical damage is also a major causative factor in neurodegenerative diseases. Such damages may include mitochondrial abnormalities, neuronal demyelination, apoptosis, neuronal death and reduced cognitive performance, potentially leading to the development of progressive neurodegenerative disorders (Nunomura et al., 2001, *J. Neuropathol. Exp. Neurol.*, 60:759-767; Girouard, 2006, *J. Appl. Physiol.* 100:328-335).

Further, the generation of ROS by sperm has been demonstrated in a large number of species and has been suggested to be attributed to an NADPH oxidase within spermatozoa (Vernet et al., *Biol. Reprod.*, 2001, 65:1102-1113). Excessive ROS generation has been suggested to be implicated in sperm pathology, including male infertility and also in some penile disorders and prostate cancer.

NADPH oxidases are multi-subunit enzymes made up of a membrane-bound cytochrome b558 domain and three cytosolic protein subunits, p47phox, p67phox and a small GTPase, Rac. Seven isoforms of NOX enzymes have been identified including NOX1, NOX2, NOX3, NOX4, NOX5, DUOX1 and DUOX2 (Leto et al., 2006, *Antioxid Redox Signal*, 8(9-10):1549-61; Cheng et al., 2001, *Gene*, 16; 269(1-2):131-40).

Thus, ROS derived from NADPH contribute to the pathogenesis of numerous diseases, especially cardiovascular diseases or disorders, respiratory disorder or disease, disease or disorder affecting the metabolism, bone disorders, neurodegenerative diseases, inflammatory diseases, reproduction disorder or disease, pain, cancer and disease or disorders of the gastrointestinal system. Therefore, it would be highly desirable to develop new active agents focusing on the ROS signalling cascade, especially on NADPH oxidases (NOX).

SUMMARY OF THE INVENTION

The present invention is directed towards new molecules useful in the treatment and/or prophylaxis of Nicotinamide adenine dinucleotide phosphate oxidase (NADPH Oxidase) related disorders such as cardiovascular diseases, respiratory disorders, disorders affecting the metabolism, skin and/or bone diseases, neurodegenerative diseases, kidney diseases, reproduction disorders, inflammatory disorders, cancers, allergic disorders, traumatisms, septic, hemorrhagic and anaphylactic shock, diseases or disorders of the gastrointestinal system and/or other diseases and disorders associated with Nicotinamide adenine dinucleotide phosphate oxidase (NADPH Oxidase). Notably, the invention is related to new molecules useful in the inhibition or reduction of ROS production in cells.

A first aspect of the invention provides a pyrazolo pyridine derivative according to Formula (I), wherein $G_1$, $G_2$, $G_3$, $G_4$ and $G_5$ are as defined below, as well as pharmaceutically acceptable salts and pharmaceutically active derivative thereof for use as a medicament.

A second aspect of the invention relates to a pharmaceutical composition containing at least one a pyrazolo pyridine derivative according to the invention, as well as pharmaceutically acceptable salts and pharmaceutically active derivative thereof and a pharmaceutically acceptable carrier, diluent or excipient thereof.

A third aspect of the invention resides in a use of a pyrazolo pyridine derivative according to the invention as well as pharmaceutically acceptable salts and pharmaceutically active derivative thereof for the preparation of a pharmaceutical composition for the treatment or prophylaxis of a disease or condition selected from cardiovascular disorders, respiratory disorders, metabolism disorders, skin disorders, bone disorders, neuroinflammatory and/or neurodegenerative disorders, kidney diseases, reproduction disorders, diseases affecting the eye and/or the lens and/or conditions affecting the inner ear, inflammatory disorders, liver diseases, pain, cancers, allergic disorders, traumatisms, septic, hemorrhagic and anaphylactic shock, diseases or disorders of the gastrointestinal system and/or other diseases and disorders associated with Nicotinamide adenine dinucleotide phosphate oxidase (NADPH Oxidase).

A fourth aspect of the invention relates to a method for treating a patient suffering from a disease or condition selected from cardiovascular disorders, respiratory disorders, metabolism disorders, skin disorders, bone disorders, neuroinflammatory and/or neurodegenerative disorders, kidney diseases, reproduction disorders, diseases affecting the eye and/or the lens and/or conditions affecting the inner ear, inflammatory disorders, liver diseases, pain, cancers, allergic disorders, traumatisms, septic, hemorrhagic and anaphylactic shock, diseases or disorders of the gastrointestinal system and other diseases and/or disorders associated with Nicotinamide adenine dinucleotide phosphate oxidase (NADPH Oxidase). The method comprises administering a pyrazolo pyridine derivative according to Formula (I), wherein $G_1$, $G_2$, $G_3$, $G_4$ and $G_5$ are as defined below, as well as pharmaceutically acceptable salts and pharmaceutically active derivative thereof in a patient in need thereof.

A fifth aspect of the invention relates to a pyrazolo pyridine derivative according to Formula (I), wherein $G_1$, $G_2$, $G_3$, $G_4$ and $G_5$ are as defined below, as well as pharmaceutically acceptable salts and pharmaceutically active derivative thereof, for use in the treatment of a disease or condition selected from cardiovascular disorders, respiratory disorders, metabolism disorders, skin disorders, bone disorders, neuroinflammatory and/or neurodegenerative disorders, kidney diseases, reproduction disorders, diseases affecting the eye and/or the lens and/or conditions affecting the inner ear, inflammatory disorders, liver diseases, pain, cancers, allergic disorders, traumatisms, septic, hemorrhagic and anaphylactic shock, diseases or disorders of the gastrointestinal system and other diseases and/or disorders associated with Nicotinamide adenine dinucleotide phosphate oxidase (NADPH Oxidase).

Other features and advantages of the invention will be apparent from the following detailed description.

DETAILED DESCRIPTION OF THE INVENTION

The following paragraphs provide definitions of the various chemical moieties that make up the compounds according to the invention and are intended to apply uniformly through-out the specification and claims, unless an otherwise expressly set out definition provides a broader definition.

The term "alkyl" when used alone or in combination with other terms, comprises a straight chain or branched $C_1$-$C_{20}$ alkyl which refers to monovalent alkyl groups having 1 to 20 carbon atoms. This term is exemplified by groups such as methyl, ethyl, n-propyl, i-propyl, n-butyl, s-butyl, i-butyl, t-butyl, n-pentyl, 1-ethylpropyl, 2-methylbutyl, 3-methylbutyl, 2,2-dimethylpropyl, n-hexyl, 2-methylpentyl, 3-methylpentyl, 4-methylpentyl, n-heptyl, 2-methylhexyl, 3-methylhexyl, 4-methylhexyl, 5-methylhexyl, n-heptyl, n-octyl, n-nonyl, n-decyl, tetrahydrogeranyl, n-dodecyl, n-tridecyl, n-tetradecyl, n-pentadecyl, n-hexadecyl, n-octadecyl, n-nonadecyl, and n-eicosanyl and the like. Preferably, these include $C_1$-$C_9$ alkyl, more preferably $C_1$-$C_6$ alkyl, especially preferably $C_1$-$C_4$ alkyl, which, by analogy, refer respectively to monovalent alkyl groups having 1 to 9 carbon atoms, monovalent alkyl groups having 1 to 6 carbon atoms and monovalent alkyl groups having 1 to 4 carbon atoms.

The term "alkenyl" when used alone or in combination with other terms, comprises a straight chain or branched $C_2$-$C_{20}$ alkenyl. It may have any available number of double bonds in any available positions, and the configuration of the double bond may be the (E) or (Z) configuration. This term is exemplified by groups such as vinyl, allyl, isopropenyl, 1-propenyl, 2-methyl-1-propenyl, 1-butenyl, 2-butenyl, 3-butenyl, 2-ethyl-1-butenyl, 3-methyl-2-butenyl, 1-pentenyl, 2-pentenyl, 3-pentenyl, 4-pentenyl, 4-methyl-3-pentenyl, 1-hexenyl, 2-hexenyl, 3-hexenyl, 4-hexenyl, 5-hexenyl, 1-heptenyl, 1-octenyl, geranyl, 1-decenyl, 1-tetradecenyl, 1-octadecenyl, 9-octadecenyl, 1-eicosenyl, and 3, 7, 11,15-tetramethyl-1-hexadecenyl, and the like. Preferably, these include $C_2$-$C_8$ alkenyl, more preferably $C_2$-$C_6$ alkenyl. Among others, especially preferred are vinyl or ethenyl (—CH=$CH_2$), n-2-propenyl (allyl, —$CH_2$CH=$CH_2$), isopropenyl, 1-propenyl, 2-methyl-1-propenyl, 1-butenyl, 2-butenyl, and 3-methyl-2-butenyl and the like.

The term "alkynyl" when used alone or in combination with other terms, comprises a straight chain or branched $C_2$-$C_{20}$ alkynyl. It may have any available number of triple bonds in any available positions. This term is exemplified by groups such as alkynyl groups that may have a carbon number of 2-20, and optionally a double bond, such as ethynyl (—C≡CH), 1-propynyl, 2-propynyl (propargyl: —$CH_2$C≡CH), 2-butynyl, 2-pentene-4-ynyl, and the like. Preferably, these include $C_2$-$C_8$ alkynyl, more preferably $C_2$-$C_6$ alkynyl and the like.

The term "heteroalkyl" refers to $C_1$-$C_{12}$-alkyl, preferably $C_1$-$C_6$-alkyl, wherein at least one carbon has been replaced by a heteroatom selected from O, N or S, including 2-methoxy ethyl and the like.

The term "aryl" refers to an unsaturated aromatic carbocyclic group of from 6 to 14 carbon atoms having a single ring (e.g., phenyl) or multiple condensed rings (e.g., indenyl, naphthyl). Aryl include phenyl, naphthyl, anthryl, phenanthrenyl and the like.

The term "alkyl aryl" refers to aryl groups having an alkyl substituent, including methyl phenyl, ethyl phenyl and the like.

The term "aryl alkyl" refers to alkyl groups having an aryl substituent, including 3-phenylpropanyl, benzyl and the like.

The term "heteroaryl" refers to a monocyclic heteroaromatic, or a bicyclic or a tricyclic fused-ring heteroaromatic group. Particular examples of heteroaromatic groups include optionally substituted pyridyl, pyrrolyl, pyrimidinyl, furyl, thienyl, imidazolyl, oxazolyl, isoxazolyl, thiazolyl, isothiazolyl, pyrazolyl, 1,2,3-triazolyl, 1,2,4-triazolyl, 1,2,3-oxadiazolyl, 1,2,4-oxadia-zolyl, 1,2,5-oxadiazolyl, 1,3,4-oxadiazolyl, 1,3,4-triazinyl, 1,2,3-triazinyl, benzofuryl, [2,3-dihydro]benzofuryl, isobenzofuryl, benzothienyl, benzotriazolyl, isobenzothienyl, indolyl, isoindolyl, 3H-indolyl, benzimidazolyl, imidazo[1,2-a]pyridyl, benzothiazolyl, benzoxa-zolyl, quinolizinyl, quinazolinyl, pthalazinyl, quinoxalinyl, cinnolinyl, napthyridinyl, pyrido[3,4-b]pyridyl, pyrido[3,2-b]pyridyl, pyrido[4,3-b]pyridyl, quinolyl, isoquinolyl, tetrazolyl, 5,6,7,8-tetrahydroquinolyl, 5,6,7,8-tetrahydroisoquinolyl, purinyl, pteridinyl, carbazolyl, xanthenyl or benzoquinolyl.

The term "alkyl heteroaryl" refers to heteroaryl groups having an alkyl substituent, including methyl furyl and the like.

The term "heteroaryl alkyl" refers to alkyl groups having a heteroaryl substituent, including furyl methyl and the like.

The term "alkenyl aryl" refers to an aryl groups having an alkenyl substituent, including vinyl phenyl and the like.

The term "aryl alkenyl" refers to an alkenyl groups having an aryl substituent, including phenyl vinyl and the like.

The term "alkenyl heteroaryl" refers to heteroaryl groups having an alkenyl substituent, including vinyl pyridinyl and the like.

The term "heteroaryl alkenyl" refers to alkenyl groups having a Heteroaryl substituent, including pyridinyl vinyl and the like.

The term "$C_3$-$C_8$-cycloalkyl" refers to a saturated carbocyclic group of from 3 to 8 carbon atoms having a single ring (e.g., cyclohexyl) or multiple condensed rings (e.g., norbornyl). $C_3$-$C_8$-cycloalkyl includes cyclopentyl, cyclohexyl, norbornyl and the like.

The term "heterocycloalkyl" refers to a $C_3$-$C_8$-cycloalkyl group according to the definition above, in which up to 3 carbon atoms are replaced by heteroatoms chosen from the group consisting of O, S, NR, R being defined as hydrogen or methyl. Heterocycloalkyl include pyrrolidinyl, piperidinyl, piperazinyl, morpholinyl, tetrahydrofuranyl and the like.

The term "alkyl $C_3$-$C_8$-cycloalkyl" refers to $C_3$-$C_8$-cycloalkyl groups having an alkyl substituent, including methyl cyclopentyl and the like.

The term "$C_3$-$C_8$-cycloalkyl alkyl" refers to alkyl groups having a $C_3$-$C_8$-cycloalkyl substituent, including 3-cyclopentyl propyl and the like.

The term "alkyl heterocycloalkyl" refers to heterocycloalkyl groups having an alkyl substituent, including 4-methylpiperidinyl and the like.

The term "heterocycloalkyl alkyl" refers to alkyl groups having a heterocycloalkyl substituent, including (1-methylpiperidin-4-yl)methyl and the like.

The term "carboxy" refers to the group —C(O)OH.

The term "carboxy alkyl" refers to alkyl groups having a carboxy substituent, including 2-carboxyethyl and the like.

The term "acyl" refers to the group —C(O)R where R includes H, "alkyl," preferably "alkyl," "aryl," "heteroaryl," "$C_3$-$C_8$-cycloalkyl," "heterocycloalkyl," "aryl alkyl," "heteroaryl alkyl," "$C_3$-$C_8$-cycloalkyl alkyl" or "heterocycloalkyl alkyl", including acetyl and the like.

The term "acyl alkyl" to alkyl groups having an acyl substituent, including 2-acetylethyl and the like.

The term "acyl aryl" refers to aryl groups having an acyl substituent, including 2-acetylphenyl and the like.

The term "acyloxy" refers to the group —OC(O)R where R includes H, "alkyl", "alkenyl," "alkynyl," "$C_3$-$C_8$-cycloalkyl," "heterocycloalkyl," "aryl," "heteroaryl," "aryl alkyl", "heteroaryl alkyl," "aryl alkenyl," "heteroaryl alkenyl," "aryl alkynyl," "heteroaryl alkynyl," "$C_3$-$C_8$-cycloalkyl alkyl," or "heterocycloalkyl alkyl", including acetyloxy and the like.

The term "acyloxy alkyl" refers to alkyl groups having an acyloxy substituent, including 2-(ethylcarbonyloxy)ethyl and the like.

The term "alkoxy" refers to the group —O—R where R includes "alkyl", "aryl", "heteroaryl", "aryl alkyl" or "heteroaryl alkyl". Preferred alkoxy groups include for example, methoxy, ethoxy, phenoxy and the like.

The term "alkoxy alkyl" refers to alkyl groups having an alkoxy substituent, including methoxyethyl and the like.

The term "alkoxycarbonyl" refers to the group —C(O)OR where R includes "alkyl", "aryl", "heteroaryl", "aryl alkyl", "heteroaryl alkyl" or "heteroalkyl".

The term "alkoxycarbonyl alkyl" refers to alkyl groups having an alkoxycarbonyl substituent, including 2-(benzyloxycarbonyl)ethyl and the like.

The term "aminocarbonyl" refers to the group —C(O)NRR' where R and R' are independently H, alkyl, aryl, heteroaryl, "aryl alkyl" or "heteroaryl alkyl," including N-phenyl carbonyl and the like.

The term "aminocarbonyl alkyl" refers to alkyl groups having an aminocarbonyl substituent, including 2-(dimethylaminocarbonyl)ethyl, N-ethyl acetamidyl, N,N-Diethyl-acetamidyl and the like.

The term "acylamino" refers to the group —NRC(O)R' where R and R' are independently H, "alkyl," "alkenyl," "alkynyl," "$C_3$-$C_8$-cycloalkyl," "heterocycloalkyl," "aryl," "heteroaryl," "aryl alkyl", "heteroaryl alkyl," "aryl alkenyl," "heteroaryl alkenyl," "aryl alkynyl," "heteroaryl alkynyl," "cycloalkyl alkyl," or "heterocycloalkyl alkyl", including acetylamino and the like.

The term "acylamino alkyl" refers to alkyl groups having an acylamino substituent, including 2-(propionylamino)ethyl and the like.

The term "ureido" refers to the group —NRC(O)NR'R" where R, R' and R" are independently H, "alkyl," "alkenyl," "alkynyl," "$C_3$-$C_8$-cycloalkyl," "heterocycloalkyl," "aryl," "heteroaryl," "aryl alkyl", "heteroaryl alkyl," "aryl alkenyl," "heteroaryl alkenyl," "aryl alkynyl," "heteroaryl alkynyl," "cycloalkyl alkyl," or "heterocycloalkyl alkyl," and where R' and R", together with the nitrogen atom to which they are attached, can optionally form a 3-8-membered heterocycloalkyl ring.

The term "ureido alkyl" refers to -alkyl groups having an ureido substituent, including 2-(N'-methylureido)ethyl and the like.

The term "carbamate" refers to the group —NRC(O)OR' where R and R' are independently "alkyl," "alkenyl," "alkynyl," "$C_3$-$C_8$-cycloalkyl," "heterocycloalkyl," "aryl," "heteroaryl," "alkyl aryl", "heteroaryl alkyl," "aryl alkenyl," "heteroaryl alkenyl," "aryl alkynyl," "heteroaryl alkynyl," "cycloalkyl alkyl," or "heterocycloalkyl alkyl" and optionally R can also be hydrogen.

The term "amino" refers to the group —NRR' where R and R' are independently H, "alkyl", "aryl", "heteroaryl", "alkyl aryl", "alkyl heteroaryl," "cycloalkyl," or "heterocycloalkyl," and where R and R', together with the nitrogen atom to which they are attached, can optionally form a 3-8-membered heterocycloalkyl ring.

The term "amino alkyl" refers to alkyl groups having an amino substituent, including 2-(1-pyrrolidinyl)ethyl and the like.

The term "ammonium" refers to a positively charged group —N$^+$RR'R" where R, R' and R" are independently "alkyl", "alkyl aryl", "alkyl heteroaryl," "cycloalkyl," or "heterocycloalkyl," and where R and R', together with the nitrogen atom to which they are attached, can optionally form a 3-8-membered heterocycloalkyl ring.

The term "ammonium alkyl" refers to alkyl groups having an ammonium substituent, including 1-ethylpyrrolidinium and the like.

The term "halogen" refers to fluoro, chloro, bromo and iodo atoms.

The term "sulfonyloxy" refers to a group —OSO$_2$—R wherein R is selected from "alkyl," "alkyl" substituted with halogens, e.g., an —OSO$_2$—CF$_3$ group, "alkenyl," "alkynyl," "$C_3$-$C_8$-cycloalkyl," "heterocycloalkyl," "aryl," "heteroaryl," "aryl alkyl", "heteroaryl alkyl," "aryl alkenyl," "heteroaryl alkenyl," "aryl alkynyl," "heteroaryl alkynyl," "cycloalkyl alkyl," or "heterocycloalkyl alkyl".

The term "sulfonyloxy alkyl" refers to alkyl groups having a sulfonyloxy substituent, including 2-(methylsulfonyloxy)ethyl and the like.

The term "sulfonyl" refers to group "—SO$_2$—R" wherein R is selected from "aryl," "heteroaryl," "alkyl," "alkyl" substituted with halogens, e.g., an —SO$_2$—CF$_3$ group, "alkenyl," "alkynyl," "$C_3$-$C_8$-cycloalkyl," "heterocycloalkyl," "aryl," "heteroaryl," "aryl alkyl", "heteroaryl alkyl," "aryl alkenyl," "heteroaryl alkenyl," "aryl alkynyl," "heteroaryl alkynyl," "cycloalkyl alkyl," or "heterocycloalkyl alkyl".

The term "sulfonyl alkyl" refers to alkyl groups having a sulfonyl substituent, including 2-(methylsulfonyl)ethyl and the like.

The term "sulfinyl" refers to a group "—S(O)—R" wherein R is selected from "alkyl," "alkyl" substituted with halogens, e.g., a —SO—CF$_3$ group, "alkenyl," "alkynyl," "$C_3$-$C_8$-cycloalkyl," "heterocycloalkyl," "aryl," "heteroaryl," "aryl alkyl", "heteroaryl alkyl," "aryl alkenyl," "heteroaryl alkenyl," "aryl alkynyl," "heteroaryl alkynyl," "$C_3$-$C_8$-cycloalkyl alkyl," or "heterocycloalkyl alkyl".

The term "sulfinyl alkyl" refers to alkyl groups having a sulfinyl substituent, including 2-(methylsulfinyl)ethyl and the like.

The term "sulfanyl" refers to groups —S—R where R includes H, "alkyl," "alkyl" substituted with halogens, e.g., a —S—CF$_3$ group, "alkenyl," "alkynyl," "$C_3$-$C_8$-cycloalkyl," "heterocycloalkyl," "aryl," "heteroaryl," "aryl alkyl", "heteroaryl alkyl," "aryl alkenyl," "heteroaryl alkenyl," "aryl alkynyl," "alkynylheteroaryl," "cycloalkyl alkyl," or "heterocycloalkyl alkyl". Preferred sulfanyl groups include methylsulfanyl, ethylsulfanyl, and the like.

The term "sulfanyl alkyl" refers to $C_1$-$C_5$-alkyl groups having a sulfanyl substituent, including 2-(ethylsulfanyl) ethyl and the like.

The term "sulfonylamino" refers to a group —NRSO$_2$—R' where R and R' are independently "alkyl," "alkenyl," "alkynyl," "$C_3$-$C_8$-cycloalkyl," "heterocycloalkyl," "aryl," "heteroaryl," "aryl alkyl", "heteroaryl alkyl," "aryl alkenyl," "heteroaryl alkenyl," "aryl alkynyl," "heteroaryl alkynyl," "$C_3$-$C_8$-cycloalkyl alkyl," or "heterocycloalkyl alkyl".

The term "sulfonylamino alkyl" refers to alkyl groups having a sulfonylamino substituent, including 2-(ethylsulfonylamino)ethyl and the like.

The term "aminosulfonyl" refers to a group —SO$_2$—NRR' where R and R' are independently H, "alkyl," "alkenyl," "alkynyl," "$C_3$-$C_8$-cycloalkyl," "heterocycloalkyl," "aryl," "heteroaryl," "aryl alkyl", "heteroaryl alkyl," "aryl alkenyl," "heteroaryl alkenyl," "aryl alkynyl," "heteroaryl alkynyl," "$C_3$-$C_8$-cycloalkyl alkyl," or "heterocycloalkyl alkyl", and where R and R', together with the nitrogen atom to which they are attached, can optionally form a 3-8-membered heterocycloalkyl ring. Aminosulfonyl groups include cyclohexylaminosulfonyl, piperidinylsulfonyl and the like.

The term "aminosulfonyl alkyl" refers to alkyl groups having an aminosulfonyl substituent, including 2-(cyclohexylaminosulfonyl)ethyl and the like.

Unless otherwise constrained by the definition of the individual substituent, the term "substituted" refers to groups substituted with from 1 to 5 substituents selected from the group consisting of "alkyl," "alkenyl," "alkynyl," "$C_3$-$C_8$-cycloalkyl," "heterocycloalkyl," "alkyl aryl," "alkyl heteroaryl," "alkyl cycloalkyl," "alkyl heterocycloalkyl," "amino," "aminosulfonyl," "ammonium," "acyl amino," "amino carbonyl," "aryl," "heteroaryl," "sulfinyl," "sulfonyl," "alkoxy," "alkoxy carbonyl," "carbamate," "sulfanyl," "halogen," trihalomethyl, cyano, hydroxy, mercapto, nitro, and the like.

The term "pharmaceutically acceptable salts or complexes" refers to salts or complexes of the below-specified compounds of Formula (I). Examples of such salts include, but are not restricted, to base addition salts formed by reaction of compounds of Formula (I) with organic or inorganic bases such as hydroxide, carbonate or bicarbonate of a metal cation such as those selected in the group consisting of alkali metals (sodium, potassium or lithium), alkaline earth metals (e.g. calcium or magnesium), or with an organic primary, secondary or tertiary alkyl amine. Amine salts derived from methylamine, dimethylamine, trimethylamine, ethylamine, diethylamine, triethylamine, morpholine, N-Me-D-glucamine, N,N'-bis(phenylmethyl)-1,2-ethanediamine, tromethamine, ethanolamine, diethanolamine, ethylenediamine, N-methylmorpholine, procaine, piperidine, piperazine and the like are contemplated being within the scope of the instant invention.

Also comprised are salts which are formed from to acid addition salts formed with inorganic acids (e.g. hydrochloric acid, hydrobromic acid, sulfuric acid, phosphoric acid, nitric acid, and the like), as well as salts formed with organic acids such as acetic acid, oxalic acid, tartaric acid, succinic acid, malic acid, fumaric acid, maleic acid, ascorbic acid, benzoic acid, tannic acid, palmoic acid, alginic acid, polyglutamic acid, naphthalene sulfonic acid, naphthalene disulfonic acid, and poly-galacturonic acid.

"Pharmaceutically active derivative" refers to any compound that upon administration to the recipient, is capable of providing directly or indirectly, the activity disclosed herein. The term "indirectly" also encompasses prodrugs which may be converted to the active form of the drug via endogenous enzymes or metabolism. The prodrug is a derivative of the compound according to the invention and presenting NADPH oxidase inhibiting activity that has a chemically or metabolically decomposable group, and a compound that may be converted into a pharmaceutically active compound in vivo by solvolysis under physiological conditions. The invention further encompasses any tautomers of the compounds according to the invention.

The term "cardiovascular disorder or disease" comprises atherosclerosis, especially diseases or disorders associated with endothelial dysfunction including but not limited to hypertension, cardiovascular complications of Type I or Type II diabetes, intimal hyperplasia, coronary heart disease, cerebral, coronary or arterial vasospasm, endothelial dysfunction, heart failure including congestive heart failure, peripheral artery disease, restenosis, trauma caused by a stent, stroke, ischemic attack, vascular complications such as after organ transplantation, or viral or bacterial infections, myocardial infarction, hypertension, formation of atherosclerotic plaques, platelet aggregation, angina pectoris, aneurysm, aortic dissection, ischemic heart disease, cardiac hypertrophy, pulmonary embolus, thrombotic events including deep vein thrombosis, injury caused after ischemia by restoration of blood flow or oxygen delivery as in organ transplantation, open heart surgery, angioplasty, hemorrhagic shock, angioplasty of ischemic organs including heart, brain, liver, kidney, retina and bowel.

The term "respiratory disorder or disease" comprises bronchial asthma, bronchitis, allergic rhinitis, adult respiratory syndrome, cystic fibrosis, lung viral infection (influenza), pulmonary hypertension and chronic obstructive pulmonary diseases (COPD).

The term "allergic disorder" includes hay fever and asthma.

The term "traumatism" includes polytraumatism.

The term "disease or disorder affecting the metabolism" includes obesity, metabolic syndrome and Type II diabetes.

The term "skin disease" or disorder" includes psoriasis, eczema, dermatitis, wound healing and scar formation.

The term "bone disorder" includes osteoporosis, osteoporasis, osteosclerosis, periodontitis, and hyperparathyroidism.

The term "neurodegenerative disease or disorder" comprises a disease or a state characterized by a central nervous system (CNS) degeneration or alteration, especially at the level of the neurons such as Alzheimer's disease, Parkinson's disease, Huntington's disease, amyotrophic lateral sclerosis, epilepsy and muscular dystrophy. It further comprises neuroinflammatory and demyelinating states or diseases such as leukoencephalopathies, and leukodystrophies.

The term "demyelinating" is referring to a state or a disease of the CNS comprising the degradation of the myelin around the axons. In the context of the invention, the term demyelinating disease is intended to comprise conditions which comprise a process that demyelinate cells such as multiple sclerosis, progressive multifocal leukoencephalopathy (PML), myelopathies, any neuroinflammatory condition involving autoreactive leukocyte within the CNS, congenital metabolic disorder, a neuropathy with abnormal myelination, drug induced demyelination, radiation induced demyelination, a hereditary demyelinating condition, a prion induced demyelinating condition, encephalitis induced demyelination or a spinal cord injury. Preferably, the condition is multiple sclerosis.

The term "kidney disease or disorder" includes diabetic nephropathy, renal failure, glomerulonephritis, nephrotoxicity of aminoglycosides and platinum compounds and hyperactive bladder.

The term "reproduction disorder or disease" includes erectile dysfunction, fertility disorders, prostatic hypertrophy and benign prostatic hypertrophy.

The term "disease or disorder affecting the eye and/or the lens" includes cataract including diabetic cataract, re-opacification of the lens post cataract surgery, diabetic and other forms of retinopathy.

The term "conditions affecting the inner ear" includes presbyacusis, tinnitus, Meniere's disease and other balance problems, utriculolithiasis, vestibular migraine, and noise induced hearing loss and drug induced hearing loss (ototoxicity).

The term "inflammatory disorder or disease" means inflammatory bowel disease, sepsis, septic shock, adult respiratory distress syndrome, pancreatitis, shock induced by trauma, bronchial asthma, allergic rhinitis, rheumatoid arthritis, chronic rheumatoid arthritis, arteriosclerosis, intracerebral hemorrhage, cerebral infarction, heart failure, myocardial infarction, psoriasis, cystic fibrosis, stroke, acute bronchitis, chronic bronchitis, acute bronchiolitis, chronic bronchiolitis, osteoarthritis, gout, myelitis, ankylosing spondylitis, Reuter syndrome, psoriatic arthritis, spondylarthritis, juvenile arthritis or juvenile ankylosing spondylitis, reactive arthritis, infectious arthritis or arthritis after infection, gonococcal arthritis, tuberculous arthritis, viral arthritis, arthritis by bacteria, syphilitic arthritis, Lyme disease, arthritis induced by "angiitis syndrome," polyarteritis nodosa, anaphylactic angiitis, Luegenec granulomatosis, rheumatoid polymyalgia, articular cell rheumatism, calcium crystal deposition arthritis, pseudogout, non-arthritic rheumatism, bursitis, tendosynovitis, epicondyle inflammation (tennis elbow), carpal tunnel syndrome, disorders by repetitive use (typing), mixed form of arthritis, neuropathic arthropathy, hemorrhagic arthritis, vascular peliosis, hypertrophic osteoarthropathy, multicentric reticulohistiocytosis, arthritis induced by specific diseases, blood pigmentation, sickle cell disease and other hemoglobin abnormality, hyperlipoproteinemia, dysgammaglobulinemia, hyperparathyroidism, acromegaly, familial Mediterranean fever, Bechet's disease, systemic autoimmune disease erythematosus, multiple sclerosis and Crohn's disease or diseases like relapsing polychondritis, chronic inflammatory bowel diseases (IBD) or the related diseases which require the administration to a mammal in a therapeutic effective dose of a compound expressed by Formula (I) in a sufficient dose to inhibit NADPH oxidase.

The term liver diseases or disorders include liver fibrosis, alcohol induced fibrosis, steatosis and non alcoholic steatohepatitis.

The term "arthritis" means acute rheumatic arthritis, chronic rheumatoid arthritis, chlamydial arthritis, chronic absorptive arthritis, chylous arthritis, arthritis based on bowel disease, filarial arthritis, gonorrheal arthritis, gouty arthritis, hemophilic arthritis, hypertrophic arthritis, juvenile chronic arthritis, Lyme arthritis, neonatal foal arthritis, nodular arthritis, ochronotic arthritis, psoriatic arthritis or suppurative arthritis, or the related diseases which require the administration to a mammal in a therapeutic effective dose of a compound expressed by Formula (I) in a sufficient dose to inhibit NADPH oxidase.

The term "pain" includes hyperalgesia associated with inflammatory pain.

The term "cancer" means carcinoma (e.g., fibrosarcoma, myxosarcoma, liposarcoma, chondrosarcoma, osteogenic sarcoma, chordoma, angiosarcoma, endothelium sarcoma, lymphangiosarcoma, lymphangioendothelioma, periosteoma, mesothelioma, Ewing's tumor, leiomyosarcoma, rhabdomyosarcoma, colon carcinoma, pancreatic cancer, breast cancer, ovarian cancer, prostatic carcinoma, squamous cell carcinoma, basal cell carcinoma, adenocarcinoma, sweat gland carcinoma, sebaceous gland carcinoma, papillary carcinoma, papillary adenocarcinoma, cystadenocarcinoma, medullary carcinoma, bronchogenic carcinoma, renal cell carcinoma, hepatocellular carcinoma, cholangiocarcinoma, choriocarcinoma, seminoma, embryonal carcinoma, Wilms' tumor, cervical cancer, orchioncus, lung cancer, small-cell lung cancer, bladder cancer or epithelial cancer) or the related diseases which require the administration to a mammal in a therapeutic effective dose of a compound expressed by the Formula (I) in a sufficient dose to inhibit NADPH oxidase.

The term "disease or disorders of the gastrointestinal system", includes gastric mucosa disorders ischemic bowel disease management, enteritis/colitis, cancer chemotherapy, or neutropenia.

As used herein, "treatment" and "treating" and the like generally mean obtaining a desired pharmacological and physiological effect. The effect may be prophylactic in terms of preventing or partially preventing a disease, symptom or condition thereof and/or may be therapeutic in terms of a partial or complete cure of a disease, condition, symptom or adverse effect attributed to the disease. The term "treatment" as used herein covers any treatment of a disease in a mammal, particularly a human, and includes: (a) preventing the disease from occurring in a subject which may be predisposed to the disease but has not yet been diagnosed as having it; (b) inhibiting the disease, i.e., arresting its development; or relieving the disease, i.e., causing regression of the disease and/or its symptoms or conditions.

The term "subject" as used herein refers to mammals. For examples, mammals contemplated by the present invention include human, primates, domesticated animals such as cattle, sheep, pigs, horses and the like.

The term "inhibitor" used in the context of the invention is defined as a molecule that inhibits completely or partially the activity of NADPH oxidase and/or inhibit or reduce the generation of reactive oxygen species (ROS).

Compositions

The invention provides pharmaceutical or therapeutic agents as compositions and methods for treating a patient, preferably a mammalian patient, and most preferably a human patient who is suffering from a medical disorder, and in particular a disorder mediated by NADPH oxidase, such as a cardiovascular disorder or disease, a respiratory disorder or disease, a disease or disorder affecting the metabolism, a skin disorder, a bone disorder, a neuroinflammatory disorder, a neurodegenerative disorder, a kidney disease, a reproduction disorder, a disease or disorder affecting the eye and/or the lens, a condition affecting the inner ear, an inflammatory disorder or disease, a liver disease, pain, a cancer and/or a disease or disorders of the gastrointestinal system.

Pharmaceutical compositions of the invention can contain one or more pyrazolo pyridine derivative in any form described herein. Compositions of this invention may further comprise one or more pharmaceutically acceptable additional ingredient(s), such as alum, stabilizers, antimicrobial agents, buffers, coloring agents, flavoring agents, adjuvants, and the like.

The compounds of the invention, together with a conventionally employed adjuvant, carrier, diluent or excipient may be placed into the form of pharmaceutical compositions and unit dosages thereof, and in such form may be employed as solids, such as tablets or filled capsules, or liquids such as solutions, suspensions, emulsions, elixirs, or capsules filled with the same, all for oral use, or in the form of sterile injectable solutions for parenteral (including subcutaneous) use. Such pharmaceutical compositions and unit dosage forms thereof may comprise ingredients in conventional proportions, with or without additional active compounds or principles, and such unit dosage forms may contain any suitable effective amount of the active ingredient commensurate with the intended daily dosage range to be employed. Compositions according to the invention are preferably injectable.

Compositions of this invention may also be liquid formulations, including, but not limited to, aqueous or oily suspensions, solutions, emulsions, syrups, and elixirs. Liquid forms suitable for oral administration may include a suitable aqueous or non-aqueous vehicle with buffers, suspending and dispensing agents, colorants, flavors and the like. The compositions may also be formulated as a dry product for reconstitution with water or other suitable vehicle before use. Such liquid preparations may contain additives, including, but not limited to, suspending agents, emulsifying agents, non-aqueous vehicles and preservatives. Suspending agents include, but are not limited to, sorbitol syrup, methyl cellulose, glucose/sugar syrup, gelatin, hydroxyethylcellulose, carboxymethyl cellulose, aluminum stearate gel, and hydrogenated edible fats. Emulsifying agents include, but are not limited to, lecithin, sorbitan monooleate, and acacia. Nonaqueous vehicles include, but are not limited to, edible oils, almond oil, fractionated coconut oil, oily esters, propylene glycol, and ethyl alcohol. Preservatives include, but are not limited to, methyl or propyl p-hydroxybenzoate and sorbic acid. Further materials as well as processing techniques and the like are set out in Part 5 of *Remington's Pharmaceutical Sciences*, $20^{th}$ Edition, 2000, Merck Publishing Company, Easton, Pa., which is incorporated herein by reference.

Solid compositions of this invention may be in the form of tablets or lozenges formulated in a conventional manner. For example, tablets and capsules for oral administration may contain conventional excipients including, but not limited to, binding agents, fillers, lubricants, disintegrants and wetting agents. Binding agents include, but are not limited to, syrup, accacia, gelatin, sorbitol, tragacanth, mucilage of starch and polyvinylpyrrolidone. Fillers include, but are not limited to, lactose, sugar, microcrystalline cellulose, maizestarch, calcium phosphate, and sorbitol. Lubricants include, but are not limited to, magnesium stearate, stearic acid, talc, polyethylene glycol, and silica. Disintegrants include, but are not limited to, potato starch and sodium starch glycollate. Wetting agents include, but are not limited to, sodium lauryl sulfate. Tablets may be coated according to methods well known in the art.

Injectable compositions are typically based upon injectable sterile saline or phosphate-buffered saline or other injectable carriers known in the art.

Compositions of this invention may also be formulated as suppositories, which may contain suppository bases including, but not limited to, cocoa butter or glycerides. Compositions of this invention may also be formulated for inhalation, which may be in a form including, but not limited to, a solution, suspension, or emulsion that may be administered as a dry powder or in the form of an aerosol using a propellant, such as dichlorodifluoromethane or trichlorofluoromethane. Compositions of this invention may also be formulated transdermal formulations comprising aqueous or non-aqueous vehicles including, but not limited to, creams, ointments, lotions, pastes, medicated plaster, patch, or membrane.

Compositions of this invention may also be formulated for parenteral administration, including, but not limited to, by injection or continuous infusion. Formulations for injection may be in the form of suspensions, solutions, or emulsions in oily or aqueous vehicles, and may contain formulation agents including, but not limited to, suspending, stabilizing, and dispersing agents. The composition may also be provided in a powder form for reconstitution with a suitable vehicle including, but not limited to, sterile, pyrogen-free water.

Compositions of this invention may also be formulated as a depot preparation, which may be administered by implantation or by intramuscular injection. The compositions may be formulated with suitable polymeric or hydrophobic materials (as an emulsion in an acceptable oil, for example), ion exchange resins, or as sparingly soluble derivatives (as a sparingly soluble salt, for example).

Compositions of this invention may also be formulated as a liposome preparation. The liposome preparation can comprise liposomes which penetrate the cells of interest or the stratum corneum, and fuse with the cell membrane, resulting in delivery of the contents of the liposome into the cell. Other suitable formulations can employ niosomes. Niosomes are lipid vesicles similar to liposomes, with membranes consisting largely of non-ionic lipids, some forms of which are effective for transporting compounds across the stratum corneum. The compounds of this invention can also be administered in sustained release forms or from sustained release drug delivery systems. A description of representative sustained release materials can also be found in the incorporated materials in *Remington's Pharmaceutical Sciences*.

Mode of Administration

Compositions of this invention may be administered in any manner, including, but not limited to, orally, parenterally, sublingually, transdermally, rectally, transmucosally, topically, via inhalation, via buccal or intranasal administration, or combinations thereof. Parenteral administration includes, but is not limited to, intravenous, intra-arterial, intra-peritoneal, subcutaneous, intramuscular, intra-thecal, and intra-articular. The compositions of this invention may also be administered in the form of an implant, which allows slow release of the compositions as well as a slow controlled i.v. infusion. In a preferred embodiment, pyrazolo pyridine derivatives according to the invention are administered intravenously or subcutaneously.

This invention is further illustrated by the following examples that are not intended to limit the scope of the invention in any way.

The dosage administered, as single or multiple doses, to an individual will vary depending upon a variety of factors, including pharmacokinetic properties, patient conditions and characteristics (sex, age, body weight, health, size), extent of symptoms, concurrent treatments, frequency of treatment and the effect desired.

Patients

In an embodiment, patients according to the invention are patients suffering from a cardiovascular disorder or disease.

In another embodiment, patients according to the invention are patients suffering from a respiratory disorder or disease.

In another embodiment, patients according to the invention are patients suffering from a disease or disorder affecting the metabolism.

In another embodiment, patients according to the invention are patients suffering from a skin disorder.

In another embodiment, patients according to the invention are patients suffering from a bone disorder.

In another embodiment, patients according to the invention are patients suffering from a neuroinflammatory disorder and/or a neurodegenerative disorder.

In another embodiment, patients according to the invention are patients suffering from a kidney disease.

In another embodiment, patients according to the invention are patients suffering from a reproduction disorder.

In another embodiment, patients according to the invention are patients suffering from a disease or disorder affecting the eye and/or the lens and/or a condition affecting the inner ear.

In another embodiment, patients according to the invention are patients suffering from an inflammatory disorder or disease.

In another embodiment, patients according to the invention are patients suffering from a liver disease.

In another embodiment, patients according to the invention are patients suffering from pain, such as inflammatory pain.

In another embodiment, patients according to the invention are patients suffering from a cancer.

In another embodiment, patients according to the invention are patients suffering from allergic disorders.

In another embodiment, patients according to the invention are patients suffering from traumatisms.

In another embodiment, patients according to the invention are patients suffering from septic, hemorrhagic and anaphylactic shock.

In another embodiment, patients according to the invention are patients suffering from a disease or disorders of the gastrointestinal system.

Use According to the Invention

In one embodiment, the invention provides a pyrazolo pyridine derivative according to Formula (I):

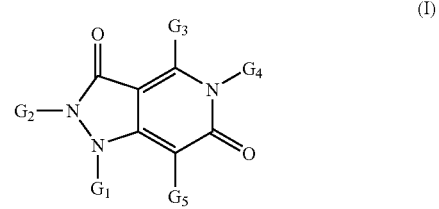

(I)

wherein $G_1$ is selected from H, optionally substituted alkyl such as aminocarbonyl alkyl (e.g. phenylacetamide), optionally substituted $C_3$-$C_8$-cycloalkyl alkyl, optionally substituted heterocycloalkyl alkyl, optionally substituted aryl alkyl such as optionally substituted phenyl alkyl like optionally substituted phenyl methyl (e.g. phenyl methyl or 3-methyl phenyl methyl or 4-fluorobenzyl or 2-chlorobenzyl or 4-chlorobenzyl or 4-methyl benzyl or 4-bromobenzyl); and optionally substituted heteroaryl alkyl such as optionally substituted pyridine alkyl like pyridine-2-yl methyl;

$G_2$ is selected from H; optionally substituted alkyl; optionally substituted alkenyl; optionally substituted alkynyl; optionally substituted aryl such as optionally substituted phenyl (e.g. phenyl or 4-fluorophenyl or 4-methoxyphenyl or 4-nitrophenyl or 2-chlorophenyl or 2-methyl phenyl or 4-(trifluoromethyl)phenyl or 4-(trifluoromethoxy)phenyl or 2,5-difluorophenyl or 2-methoxyphenyl); optionally substituted alkyl aryl; optionally substituted aryl alkyl; optionally substituted heteroaryl, such as optionally substituted benzothiazolyl (e.g. 1,3-benzothiazol-2-yl) or optionally substituted pyridinyl (e.g. pyridin-2-yl); optionally substituted alkyl heteroaryl; optionally substituted heteroaryl alkyl; optionally substituted alkenyl aryl; optionally substituted aryl alkenyl; optionally substituted alkenyl heteroaryl; optionally substituted heteroaryl alkenyl; optionally substituted $C_3$-$C_8$-cycloalkyl; optionally substituted heterocycloalkyl; optionally substituted alkyl $C_3$-$C_8$-cycloalkyl; optionally substituted $C_3$-$C_8$-cycloalkyl alkyl; optionally substituted alkyl heterocycloalkyl and optionally substituted heterocycloalkyl alkyl;

$G_3$ is selected from H; optionally substituted alkyl such as methyl or ethyl; optionally substituted alkenyl; optionally substituted alkynyl; optionally substituted aryl such as optionally substituted phenyl (e.g. phenyl); optionally substituted alkyl aryl; optionally substituted aryl alkyl; optionally substituted heteroaryl; optionally substituted alkyl heteroaryl; optionally substituted heteroaryl alkyl; optionally substituted alkenyl aryl; optionally substituted aryl alkenyl; optionally substituted alkenyl heteroaryl; optionally substituted heteroaryl alkenyl; optionally substituted $C_3$-$C_8$-cycloalkyl; optionally substituted heterocycloalkyl; optionally substituted alkyl $C_3$-$C_8$-cycloalkyl; optionally substituted $C_3$-$C_8$-cycloalkyl alkyl; optionally substituted alkyl heterocycloalkyl and optionally substituted heterocycloalkyl alkyl;

$G_4$ is selected from H, optionally substituted alkyl such as optionally substituted pentyl (e.g. isopentyl) or optionally substituted heteroalkyl such as optionally substituted methoxy (e.g. 2-methoxyethyl); optionally substituted alkenyl; optionally substituted alkynyl; optionally substituted aryl; optionally substituted alkyl aryl; optionally substituted aryl alkyl such as optionally substituted phenyl methyl (e.g. benzoic acid methyl or benzyl) or optionally substituted phenyl ethyl (e.g. 2-phenyl ethyl, 4-methoxyphenyl ethyl); optionally substituted heteroaryl; optionally substituted alkyl heteroaryl; optionally substituted heteroaryl alkyl such as optionally substituted thiophenyl alkyl like optionally substituted thiophenyl methyl (e.g. thiophen-2-yl methyl) or optionally substituted imidazolyl alkyl like optionally substituted imidazolyl ethyl (e.g. imidazol-4-yl ethyl) or optionally substituted indolyl alkyl like optionally substituted indolyl ethyl (e.g. indol-3-yl ethyl) or optionally substituted furanyl alkyl like optionally substituted furanyl methyl (e.g. furan-2-yl methyl) or optionally substituted benzodioxolyl alkyl like optionally substituted benzodioxolyl methyl (e.g. 1,3-benzodioxol-5-yl methyl) or optionally substituted pyridinyl alkyl like optionally substituted pyridinyl methyl (e.g. pyridine-3-yl methyl or pyridin-2-yl methyl); optionally substituted alkenyl aryl; optionally substituted aryl alkenyl; optionally substituted alkenyl heteroaryl; optionally substituted heteroaryl alkenyl; optionally substituted $C_3$-$C_8$-cycloalkyl; optionally substituted heterocycloalkyl such as optionally substituted morpholinyl (e.g. 5-morpholin-4-yl) or optionally substituted piperazinyl (e.g. 4-methyl piperazinyl) or optionally substituted piperidinyl (e.g. 4-methylbenzyl)piperidin-4-yl); optionally substituted alkyl $C_3$-$C_8$-cycloalkyl; and optionally substituted $C_3$-$C_8$-cycloalkyl alkyl; optionally substituted alkyl heterocycloalkyl and optionally substituted heterocycloalkyl alkyl such as optionally substituted morpholinyl alkyl like optionally substituted morpholinyl propyl (e.g. 3-(morpholin-4-yl) propyl)) optionally substituted morpholinyl ethyl (e.g. 2-morpholin-4-ylethyl); or optionally substituted piperazinyl alkyl like optionally substituted piperazinyl ethyl (e.g. 2-(4-acetylpiperazin-1-yl)ethyl or 2-(4-hexanoyl piperazin-1-yl)ethyl) or optionally substituted pyrrolidinyl alkyl like optionally substituted pyrrolidinyl propyl (e.g. 3-(2-oxopyrrolidin-1-yl) propyl) or optionally substituted tetrahydrofuranyl alkyl like optionally substituted tetrahydrofuranyl methyl (e.g. tetrahydrofuran-2-yl methyl);

$G_5$ is selected from H, optionally substituted alkyl; optionally substituted alkenyl; optionally substituted alkynyl; optionally substituted aryl; optionally substituted alkyl aryl; optionally substituted aryl alkyl; optionally substituted heteroaryl; optionally substituted alkyl heteroaryl; optionally substituted heteroaryl alkyl; optionally substituted alkenyl aryl; optionally substituted aryl alkenyl; optionally substituted alkenyl heteroaryl; optionally substituted heteroaryl alkenyl; optionally substituted $C_3$-$C_8$-cycloalkyl; optionally substituted heterocycloalkyl; optionally substituted alkyl $C_3$-$C_8$-cycloalkyl; optionally substituted $C_3$-$C_8$-cycloalkyl alkyl; optionally substituted alkyl heterocycloalkyl and optionally substituted heterocycloalkyl alkyl; as well as pharmaceutically acceptable salts and pharmaceutically active derivative thereof, for use as a medicament.

In a further embodiment, the invention provides a pyrazolo pyridine derivative according to the invention wherein $G_1$ is H.

In another further embodiment, the invention provides a pyrazolo pyridine derivative according to the invention wherein $G_1$ is selected from optionally substituted aryl alkyl and optionally substituted heteroaryl alkyl.

In another further embodiment, the invention provides a pyrazolo pyridine derivative according to the invention wherein $G_1$ is optionally substituted alkyl.

In another further embodiment, the invention provides a pyrazolo pyridine derivative according to the invention wherein $G_2$ is selected from optionally substituted aryl and optionally substituted heteroaryl.

In another further embodiment, the invention provides a pyrazolo pyridine derivative according to the invention wherein $G_3$ is H.

In another further embodiment, the invention provides a pyrazolo pyridine derivative according to the invention wherein $G_3$ is optionally substituted alkyl, such as optionally substituted methyl.

In another further embodiment, the invention provides a pyrazolo pyridine derivative according to the invention wherein $G_3$ is optionally substituted aryl.

In another further embodiment, the invention provides a pyrazolo pyridine derivative according to the invention wherein $G_4$ is selected from optionally substituted alkyl; optionally substituted alkenyl and optionally substituted alkynyl.

In another further embodiment, the invention provides a pyrazolo pyridine derivative according to the invention wherein $G_4$ is selected from optionally substituted optionally substituted aryl alkyl and substituted heteroaryl alkyl.

In another further embodiment, the invention provides a pyrazolo pyridine derivative according to the invention wherein G$_4$ is optionally substituted optionally substituted C$_3$-C$_8$-cycloalkyl alkyl and optionally substituted heterocycloalkyl alkyl.

In another further embodiment, the invention provides a pyrazolo pyridine derivative according to the invention wherein G$_4$ is optionally substituted heterocycloalkyl.

In another further embodiment, the invention provides a pyrazolo pyridine derivative according to the invention wherein G$_5$ is H.

In another embodiment, the invention provides a use of a pyrazolo pyridine derivative according to Formula (I):

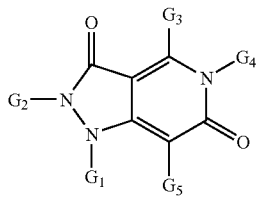

(I)

wherein G$_1$ is selected from H, optionally substituted alkyl such as aminocarbonyl alkyl (e.g. phenylacetamide), optionally substituted cycloalkyl alkyl, optionally substituted heterocycloalkyl alkyl, optionally substituted aryl alkyl such as optionally substituted phenyl alkyl like optionally substituted phenyl methyl (e.g. phenyl methyl or 3-methyl phenyl methyl or 4-fluorobenzyl or 2-chlorobenzyl or 4-chlorobenzyl or 4-methyl benzyl or 4-bromobenzyl); and optionally substituted heteroaryl alkyl such as optionally substituted pyridine alkyl like pyridine-2-yl methyl;

G$_2$ is selected from H; optionally substituted alkyl; optionally substituted alkenyl; optionally substituted alkynyl; optionally substituted aryl such as optionally substituted phenyl (e.g. phenyl or 4-fluorophenyl or 4-methoxyphenyl or 4-nitrophenyl or 2-chlorophenyl or 2-methyl phenyl or 4-(trifluoromethyl)phenyl or 4-(trifluoromethoxy)phenyl or 2,5-difluorophenyl or 2-methoxyphenyl); optionally substituted alkyl aryl; optionally substituted aryl alkyl; optionally substituted heteroaryl, such as optionally substituted benzothiazolyl (e.g. 1,3-benzothiazol-2-yl) or optionally substituted pyridinyl (e.g. pyridin-2-yl); optionally substituted alkyl heteroaryl; optionally substituted heteroaryl alkyl; optionally substituted alkenyl aryl; optionally substituted aryl alkenyl; optionally substituted alkenyl heteroaryl; optionally substituted heteroaryl alkenyl; optionally substituted C$_3$-C$_8$-cycloalkyl; optionally substituted heterocycloalkyl; optionally substituted alkyl C$_3$-C$_8$-cycloalkyl; optionally substituted C$_3$-C$_8$-cycloalkyl alkyl; optionally substituted alkyl heterocycloalkyl and optionally substituted heterocycloalkyl alkyl;

G$_3$ is selected from H; optionally substituted alkyl such as methyl or ethyl; optionally substituted alkenyl; optionally substituted alkynyl; optionally substituted aryl such as optionally substituted phenyl (e.g. phenyl); optionally substituted alkyl aryl; optionally substituted aryl alkyl; optionally substituted heteroaryl; optionally substituted alkyl heteroaryl; optionally substituted heteroaryl alkyl; optionally substituted alkenyl aryl; optionally substituted aryl alkenyl; optionally substituted alkenyl heteroaryl; optionally substituted heteroaryl alkenyl; optionally substituted C$_3$-C$_8$-cycloalkyl; optionally substituted heterocycloalkyl; optionally substituted alkyl C$_3$-C$_8$-cycloalkyl; optionally substituted C$_3$-C$_8$-cycloalkyl alkyl; optionally substituted alkyl heterocycloalkyl and optionally substituted heterocycloalkyl alkyl;

G$_4$ is selected from H, optionally substituted alkyl such as pentyl (e.g. isopentyl) or optionally substituted heteroalkyl such as optionally substituted methoxy (e.g. 2-methoxyethyl); optionally substituted alkenyl; optionally substituted alkynyl; optionally substituted aryl; optionally substituted alkyl aryl; optionally substituted aryl alkyl; optionally substituted phenyl methyl (e.g. benzoic acid methyl or benzyl) or optionally substituted phenyl ethyl (e.g. 2-phenyl ethyl, 2-(4-methoxyphenyl)ethyl); optionally substituted heteroaryl; optionally substituted alkyl heteroaryl; optionally substituted heteroaryl alkyl such as optionally substituted thiophenyl alkyl like optionally substituted thiophenyl methyl (e.g. thiophen-2-yl methyl) or optionally substituted imidazolyl alkyl like optionally substituted imidazolyl ethyl (e.g. imidazol-4-yl ethyl) or optionally substituted indolyl alkyl like optionally substituted indolyl ethyl (e.g. indol-3-yl ethyl) or optionally substituted furanyl alkyl like optionally substituted furanyl methyl (e.g. furan-2-yl methyl) or optionally substituted benzodioxolyl alkyl like optionally substituted benzodioxolyl methyl (e.g. 1,3-benzodioxol-5-yl methyl) or optionally substituted pyridinyl alkyl like optionally substituted pyridinyl methyl (e.g. pyridine-3-yl methyl or pyridin-2-yl methyl); optionally substituted alkenyl aryl; optionally substituted aryl alkenyl; optionally substituted alkenyl heteroaryl; optionally substituted heteroaryl alkenyl; optionally substituted C$_3$-C$_8$-cycloalkyl; optionally substituted heterocycloalkyl such as optionally substituted morpholinyl (e.g. 5-morpholin-4-yl) or optionally substituted piperazinyl (e.g. 4-methyl piperazinyl) or optionally substituted piperidinyl (e.g. 4-methylbenzyl)piperidin-4-yl); optionally substituted alkyl C$_3$-C$_8$-cycloalkyl; and optionally substituted C$_3$-C$_8$-cycloalkyl alkyl; optionally substituted alkyl heterocycloalkyl and optionally substituted heterocycloalkyl alkyl such as optionally substituted morpholinyl alkyl like optionally substituted morpholinyl propyl (e.g. 3-(morpholin-4-yl) propyl)), optionally substituted morpholinyl ethyl (e.g. 2-morpholin-4-ylethyl); or optionally substituted piperazinyl alkyl like optionally substituted piperazinyl ethyl (e.g. 2-(4-acetylpiperazin-1-yl)ethyl or 2-(4-hexanoyl piperazin-1-yl)ethyl) or optionally substituted pyrrolidinyl alkyl like optionally substituted pyrrolidinyl propyl (e.g. 3-(2-oxopyrrolidin-1-yl) propyl) or optionally substituted tetrahydrofuranyl alkyl like optionally substituted tetrahydrofuranyl methyl (e.g. tetrahydrofuran-2-yl methyl);

G$_5$ is selected from H, optionally substituted alkyl; optionally substituted alkenyl; optionally substituted alkynyl; optionally substituted aryl; optionally substituted alkyl aryl; optionally substituted aryl alkyl; optionally substituted heteroaryl; optionally substituted alkyl heteroaryl; optionally substituted heteroaryl alkyl; optionally substituted alkenyl aryl; optionally substituted aryl alkenyl; optionally substituted alkenyl heteroaryl; optionally substituted heteroaryl alkenyl; optionally substituted C$_3$-C$_8$-cycloalkyl; optionally substituted heterocycloalkyl; optionally substituted alkyl C$_3$-C$_8$-cycloalkyl; optionally substituted C$_3$-C$_8$-cycloalkyl alkyl; optionally substituted alkyl heterocycloalkyl and optionally substituted heterocycloalkyl alkyl; as well as pharmaceutically acceptable salts and pharmaceutically active derivative thereof, for the preparation of a pharmaceutical composition for the treatment or prophylaxis of a disease or condition selected from cardiovascular disorders, respiratory disorders, metabolism disorders, skin disorders, bone disorders, neuroinflammatory and/or neurodegenerative disorders, kidney diseases, reproduction disorders, diseases affecting the eye and/or the lens and/or conditions affecting the inner ear, inflammatory disorders, liver diseases, pain, cancers, allergic disorders, traumatisms, septic, hemorrhagic and anaphylactic shock, disorders of the gastrointestinal system and other diseases and disorders associated with Nicotinamide adenine dinucleotide phosphate oxidase (NADPH Oxidase).

In another embodiment, the invention provides a pyrazolo pyridine derivative according to Formula (I):

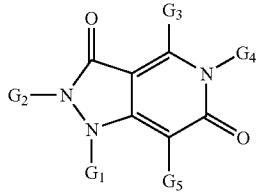

wherein $G_1$, $G_2$, $G_3$, $G_4$ and $G_5$ are as described herein; as well as pharmaceutically acceptable salts and pharmaceutically active derivative thereof, for use in the treatment or prophylaxis of a disease or condition selected from cardiovascular disorders, respiratory disorders, metabolism disorders, skin disorders, bone disorders, neuroinflammatory and/or neurodegenerative disorders, kidney diseases, reproduction disorders, diseases affecting the eye and/or the lens and/or conditions affecting the inner ear, inflammatory disorders, liver diseases, pain, cancers, allergic disorders, traumatisms, septic, hemorrhagic and anaphylactic shock, disorders of the gastrointestinal system and other diseases and disorders associated with Nicotinamide adenine dinucleotide phosphate oxidase (NADPH Oxidase).

Compounds of the present invention include in particular those selected from the following group:
4-methyl-2-phenyl-5-(thiophen-2-ylmethyl)-1H-pyrazolo[4,3-c]pyridine-3,6(2H,5H)-dione;
2-(1,3-benzothiazol-2-yl)-5-[2-(1H-imidazol-4-yl)ethyl]-4-methyl-1H-pyrazolo[4,3-c]pyridine-3,6(2H,5H)-dione;
2-(1,3-benzothiazol-2-yl)-5-[2-(1H-indol-3-yl)ethyl]-4-methyl-1H-pyrazolo[4,3-c]pyridine-3,6(2H,5H)-dione;
2-(1,3-benzothiazol-2-yl)-4-methyl-5-(3-morpholin-4-ylpropyl)-1H-pyrazolo[4,3-c]pyridine-3,6(2H,5H)-dione;
5-(furan-2-ylmethyl)-4-methyl-2-phenyl-1H-pyrazolo[4,3-c]pyridine-3,6(2H,5H)-dione;
4-{[2-(1,3-benzothiazol-2-yl)-4-methyl-3,6-dioxo-1,2,3,6-tetrahydro-5H-pyrazolo[4,3-c]pyridin-5-yl]methyl}benzoic acid;
4-methyl-2-phenyl-5-(pyridin-3-ylmethyl)-1H-pyrazolo[4,3-c]pyridine-3,6(2H,5H)-dione;
4-methyl-2-phenyl-5-(2-phenylethyl)-1H-pyrazolo[4,3-c]pyridine-3,6(2H,5H)-dione;
5-[2-(4-acetylpiperazin-1-yl)ethyl]-2-(1,3-benzothiazol-2-yl)-4-methyl-1H-pyrazolo[4,3-c]pyridine-3,6(2H,5H)-dione;
2-(1,3-benzothiazol-2-yl)-4-methyl-5-(2-methylbutyl)-1H-pyrazolo[4,3-c]pyridine-3,6(2H,5H)-dione;
2-(1,3-benzothiazol-2-yl)-5-[2-(4-methoxyphenyl)ethyl]-4-methyl-1H-pyrazolo[4,3-c]pyridine-3,6(2H,5H)-dione;
2-(1,3-benzothiazol-2-yl)-5-[2-(4-hexanoylpiperazin-1-yl)ethyl]-4-methyl-1H-pyrazolo[4,3-c]pyridine-3,6(2H,5H)-dione;
2-(1,3-benzothiazol-2-yl)-1-benzyl-5-(furan-2-ylmethyl)-4-methyl-1H-pyrazolo[4,3-c]pyridine-3,6(2H,5H)-dione;
5-[2-(1H-indol-3-yl)ethyl]-4-methyl-1-(3-methylbenzyl)-2-phenyl-1H-pyrazolo[4,3-c]pyridine-3,6(2H,5H)-dione;
1-(4-fluorobenzyl)-5-[2-(1H-indol-3-yl)ethyl]-4-methyl-2-phenyl-1H-pyrazolo[4,3-c]pyridine-3,6(2H,5H)-dione;
1-(2-chlorobenzyl)-4-methyl-5-[3-(2-oxopyrrolidin-1-yl)propyl]-2-phenyl-1H-pyrazolo[4,3-c]pyridine-3,6(2H,5H)-dione;
2-(1,3-benzothiazol-2-yl)-1-benzyl-4-methyl-5-(tetrahydrofuran-2-ylmethyl)-1H-pyrazolo[4,3-c]pyridine-3,6(2H,5H)-dione;
1-(4-chlorobenzyl)-5-[2-(1H-imidazol-4-yl)ethyl]-4-methyl-2-phenyl-1H-pyrazolo[4,3-c]pyridine-3,6(2H,5H)-dione; and
5-(1,3-benzodioxol-5-ylmethyl)-4-methyl-2-phenyl-1H-pyrazolo[4,3-c]pyridine-3,6(2H,5H)-dione;
5-benzyl-4-methyl-2-phenyl-1H-pyrazolo[4,3-c]pyridine-3,6(2H,5H)-dione;
5-benzyl-2-(4-fluorophenyl)-4-methyl-1H-pyrazolo[4,3-c]pyridine-3,6(2H,5H)-dione;
5-benzyl-2-(4-methoxyphenyl)-4-methyl-1H-pyrazolo[4,3-c]pyridine-3,6(2H,5H)-dione;
2-(1,3-benzothiazol-2-yl)-4-methyl-5-morpholin-4-yl-1H-pyrazolo[4,3-c]pyridine-3,6(2H,5H)-dione;
5-benzyl-4-methyl-2-(4-nitrophenyl)-1H-pyrazolo[4,3-c]pyridine-3,6(2H,5H)-dione;
2-(1,3-benzothiazol-2-yl)-4-methyl-1-(3-methylbenzyl)-5-(3-morpholin-4-ylpropyl)-1H-pyrazolo[4,3-c]pyridine-3,6(2H,5H)-dione;
2-(1,3-benzothiazol-2-yl)-1-(4-fluorobenzyl)-4-methyl-5-(3-morpholin-4-ylpropyl)-1H-pyrazolo[4,3-c]pyridine-3,6(2H,5H)-dione;
2-(1,3-benzothiazol-2-yl)-4-methyl-1-(4-methylbenzyl)-5-(3-morpholin-4-ylpropyl)-1H-pyrazolo[4,3-c]pyridine-3,6(2H,5H)-dione;
2-(1,3-benzothiazol-2-yl)-1-(2-chlorobenzyl)-4-methyl-5-morpholin-4-yl-1H-pyrazolo[4,3-c]pyridine-3,6(2H,5H)-dione;
2-(1,3-benzothiazol-2-yl)-1-(4-bromobenzyl)-4-methyl-5-(2-morpholin-4-ylethyl)-1H-pyrazolo[4,3-c]pyridine-3,6(2H,5H)-dione;
2-[2-(1,3-benzothiazol-2-yl)-4-methyl-5-(3-morpholin-4-ylpropyl)-3,6-dioxo-2,3,5,6-tetrahydro-1H-pyrazolo[4,3-c]pyridin-1-yl]-N-phenylacetamide;
4-methyl-2-phenyl-5-(tetrahydrofuran-2-ylmethyl)-1H-pyrazolo[4,3-c]pyridine-3,6(2H,5H)-dione;
2-(1,3-benzothiazol-2-yl)-4-methyl-5-(2-phenylethyl)-1H-pyrazolo[4,3-c]pyridine-3,6(2H,5H)-dione;
5-[2-(1H-indol-3-yl)ethyl]-4-methyl-2-phenyl-1H-pyrazolo[4,3-c]pyridine-3,6(2H,5H)-dione;
4-methyl-5-morpholin-4-yl-2-phenyl-1H-pyrazolo[4,3-c]pyridine-3,6(2H,5H)-dione;
2-(1,3-benzothiazol-2-yl)-1-(2-chlorobenzyl)-4-methyl-5-(3-morpholin-4-ylpropyl)-1H-pyrazolo[4,3-c]pyridine-3,6(2H,5H)-dione;
5-benzyl-4-ethyl-2-(4-fluorophenyl)-1H-pyrazolo[4,3-c]pyridine-3,6(2H,5H)-dione;
4-ethyl-2-(4-fluorophenyl)-5-(2-phenylethyl)-1H-pyrazolo[4,3-c]pyridine-3,6(2H,5H)-dione;
4-ethyl-2-(4-fluorophenyl)-5-morpholin-4-yl-1H-pyrazolo[4,3-c]pyridine-3,6(2H,5H)-dione;
4-methyl-5-(2-morpholin-4-ylethyl)-2-phenyl-1H-pyrazolo[4,3-c]pyridine-3,6(2H,5H)-dione;
4-ethyl-5-morpholin-4-yl-2-phenyl-1H-pyrazolo[4,3-c]pyridine-3,6(2H,5H)-dione;
2-(2-chlorophenyl)-4-methyl-5-(pyridin-2-ylmethyl)-1H-pyrazolo[4,3-c]pyridine-3,6(2H,5H)-dione;
4-methyl-2-(2-methylphenyl)-5-(3-morpholin-4-ylpropyl)-1H-pyrazolo[4,3-c]pyridine-3,6(2H,5H)-dione;
2-(1,3-benzothiazol-2-yl)-4-methyl-1-(pyridin-2-ylmethyl)-5-(tetrahydrofuran-2-ylmethyl)-1H-pyrazolo[4,3-c]pyridine-3,6(2H,5H)-dione;
2-(1,3-benzothiazol-2-yl)-4-ethyl-5-(pyridin-2-ylmethyl)-1H-pyrazolo[4,3-c]pyridine-3,6(2H,5H)-dione;
2-(1,3-benzothiazol-2-yl)-4-ethyl-5-(3-morpholin-4-ylpropyl)-1H-pyrazolo[4,3-c]pyridine-3,6(2H,5H)-dione;
2-(1,3-benzothiazol-2-yl)-4-ethyl-5-(2-methoxyethyl)-1H-pyrazolo[4,3-c]pyridine-3,6(2H,5H)-dione;
2-(1,3-benzothiazol-2-yl)-4-ethyl-5-(4-methylpiperazin-1-yl)-1H-pyrazolo[4,3-c]pyridine-3,6(2H,5H)-dione;

2-(1,3-benzothiazol-2-yl)-4-ethyl-5-[1-(4-methylbenzyl)piperidin-4-yl]-1H-pyrazolo[4,3-c]pyridine-3,6(2H,5H)-dione;
4-ethyl-2-(4-fluorophenyl)-5-(pyridin-2-ylmethyl)-1H-pyrazolo[4,3-c]pyridine-3,6(2H,5H)-dione;
4-ethyl-2-(4-fluorophenyl)-5-(3-morpholin-4-ylpropyl)-1H-pyrazolo[4,3-c]pyridine-3,6(2H,5H)-dione;
4-ethyl-2-(4-fluorophenyl)-5-(2-methoxyethyl)-1H-pyrazolo[4,3-c]pyridine-3,6(2H,5H)-dione;
5-(2-morpholin-4-ylethyl)-2-pyridin-2-yl-1H-pyrazolo[4,3-c]pyridine-3,6(2H,5H)-dione;
2,4-diphenyl-5-(pyridin-3-ylmethyl)-1H-pyrazolo[4,3-c]pyridine-3,6(2H,5H)-dione;
2-(2-chlorophenyl)-4-ethyl-5-(pyridin-3-ylmethyl)-1H-pyrazolo[4,3-c]pyridine-3,6(2H,5H)-dione;
4-methyl-2-(2-methylphenyl)-5-(pyridin-2-ylmethyl)-1H-pyrazolo[4,3-c]pyridine-3,6(2H,5H)-dione;
4-ethyl-5-(3-morpholin-4-ylpropyl)-2-[4-(trifluoromethyl)phenyl]-1H-pyrazolo[4,3-c]pyridine-3,6(2H,5H)-dione;
4-ethyl-5-(3-morpholin-4-ylpropyl)-2-[4-(trifluoromethoxy)phenyl]-1H-pyrazolo[4,3-c]pyridine-3,6(2H,5H)-dione;
2-(2,5-difluorophenyl)-4-ethyl-5-(3-morpholin-4-ylpropyl)-1H-pyrazolo[4,3-c]pyridine-3,6(2H,5H)-dione; and
4-ethyl-2-(2-methoxyphenyl)-5-(3-morpholin-4-ylpropyl)-1H-pyrazolo[4,3-c]pyridine-3,6(2H,5H)-dione.

In another embodiment, the invention provides a method for treating a patient suffering from a disease or condition selected from cardiovascular disorders, respiratory disorders, metabolism disorders, skin disorders, bone disorders, neuroinflammatory and/or neurodegenerative disorders, kidney diseases, reproduction disorders, diseases affecting the eye and/or the lens and/or conditions affecting the inner ear, inflammatory disorders, liver diseases, pain, cancers allergic disorders, traumatisms, septic, hemorrhagic and anaphylactic shock, disorders of the gastrointestinal system and other diseases and disorders associated with Nicotinamide adenine dinucleotide phosphate oxidase (NADPH Oxidase). The method comprises administering a compound according to Formula (I) in a patient in need thereof.

In another embodiment, the invention provides a pyrazolo pyridine derivative according to the invention; as well as pharmaceutically acceptable salts and pharmaceutically active derivative thereof, for the treatment of a disease or condition selected from cardiovascular disorders, respiratory disorders, metabolism disorders, skin disorders, bone disorders, neuroinflammatory and/or neurodegenerative disorders, kidney diseases, reproduction disorders, diseases affecting the eye and/or the lens and/or conditions affecting the inner ear, inflammatory disorders, liver diseases, pain, cancers allergic disorders, traumatisms, septic, hemorrhagic and anaphylactic shock, disorders of the gastrointestinal system and other diseases and disorders associated with Nicotinamide adenine dinucleotide phosphate oxidase (NADPH Oxidase).

In another embodiment, the invention provides a pharmaceutical composition containing at least one derivative pyrazolo pyridine according to Formula (I) and a pharmaceutically acceptable carrier, diluent or excipient thereof.

The compounds of invention have been named according the IUPAC standards used in the program ACD/Name (product version 10.01).

Compounds according to the present invention also comprise its tautomers, its geometrical isomers, its optically active forms as enantiomers, diastereomers and its racemate forms, as well as pharmaceutically acceptable salts thereof. The derivatives exemplified in this invention may be prepared from readily available starting materials using the following general methods and procedures. It will be appreciated that where typical or preferred experimental conditions (i.e. reaction temperatures, time, moles of reagents, solvents etc.) are given, other experimental conditions can also be used unless otherwise stated. Optimum reaction conditions may vary with the particular reactants or solvents used, but such conditions can be determined by the person skilled in the art, using routine optimisation procedures.

References cited herein are hereby incorporated by reference in their entirety. The present invention is not to be limited in scope by the specific embodiments described herein, which are intended as single illustrations of individual aspects of the invention, and functionally equivalent methods and components are within the scope of the invention. Indeed, various modifications of the invention, in addition to those shown and described herein will become apparent to those skilled in the art from the foregoing description and accompanying drawings. Such modifications are intended to fall within the scope of the appended claims.

The invention having been described, the following examples are presented by way of illustration, and not limitation.

Synthesis of Compounds of the Invention:

The novel derivatives according to Formula (I) can be prepared from readily available starting materials using the following general methods and procedures. It will be appreciated that where typical or preferred experimental conditions (i.e. reaction temperatures, time, moles of reagents, solvents etc.) are given, other experimental conditions can also be used unless otherwise stated. Optimum reaction conditions may vary with the particular reactants or solvents used, but such conditions can be determined by the person skilled in the art, using routine optimisation procedures.

The general synthetic approach for obtaining compounds of Formula (I) is depicted in Scheme 1 below.

Scheme 1

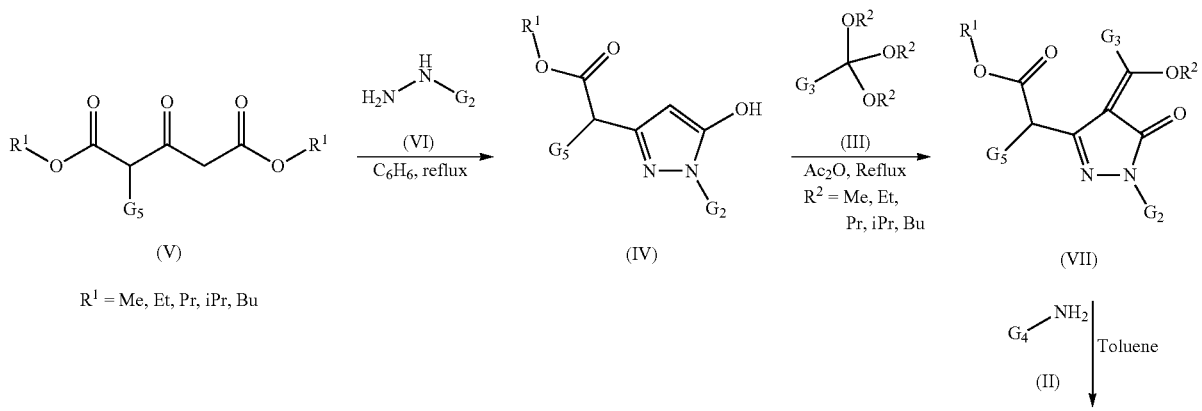

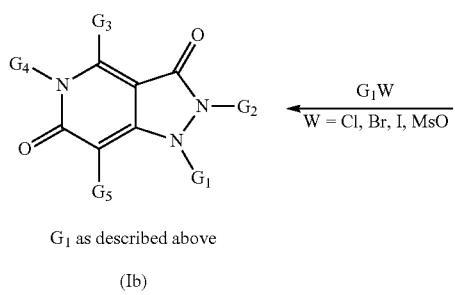

$G_1$ as described above (Ib)

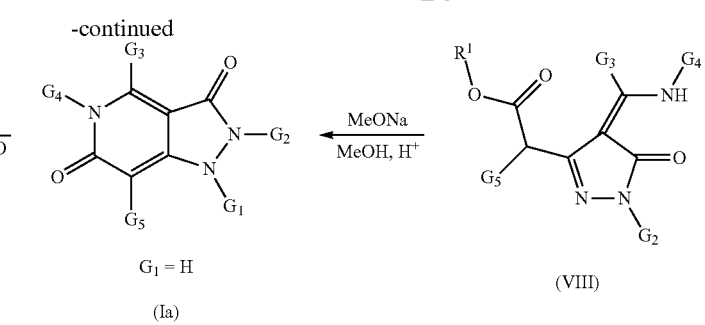

$G_1 = H$ (Ia)  (VIII)

Pyrazolo pyridine derivatives according to Formula (I), whereby the substituents $G_1$, $G_2$, $G_3$, $G_4$ and $G_5$ are as above defined, may be prepared in three chemical steps, from custom made or commercially available substituted hydrazine derivatives according to Formula (VI), acetone dicarboxylate derivatives according to Formula (V), primary amine derivatives according to Formula (II) and trialkyl ortho ester derivatives according to Formula (III), following synthetic protocol highlighted as outlined in the Scheme 1 below. In a more specific method, a hydrazine derivative according to Formula (VI) wherein $G_2$ is defined as above is reacted with an acetone dicarboxylate derivative according to Formula (V) wherein $G_5$ and $R^1$ are defined as above, in neutral and under refluxing conditions in a suitable solvents like benzene, toluene or other unreactive solvents over time depending of the intrinsic reactivity of compounds according to Formula (VI) to give the corresponding 4-substituted 2-hydroxyl pyrazole derivatives according to Formula (IV). The intermediate compounds according to Formula (IV) are further reacted with trialkyl ortho ester derivatives according to Formula (III) wherein $G_3$ and $R^2$ are defined as above, to allow formation of an intermediate of Formula (VII) in presence of acetic acid and under refluxing conditions. Intermediate compounds of Formula (VII) are further treated with primary amine derivatives according to Formula (II) wherein $G_4$ is defined as above, in solvents such as toluene or benzene under refluxing conditions, to obtain the intermediate compounds of Formula (VIII). The pyrazolo derivatives according to Formula (Ia), i.e. of Formula (I) wherein $G_1$ is H, are isolated after cyclisation of intermediate compounds of Formula (VIII), preferably in protic solvents in presence of base such as sodium methanolate, sodium isopropanolate or the like, using standard refluxing conditions well known to the person skilled in the art as shown in the Scheme 1.

This reaction may be performed in solvents like methanol, ethanol, isopropanol or other unreactive solvents at room temperature over time depending of the intrinsic reactivity of compounds according to Formula (VIII), but usually required the need of traditional thermic heating or microwave methods, using standard conditions well known to the person skilled in the art as shown in Scheme 1, above. In a subsequent step, the pyrazolo pyridine derivatives of Formula (Ia) were treated with an alkylating agent such as alkyl chlorides, bromides, iodides or mesylates, wherein $G_1$ is defined as above, in presence of a suitable base, e.g. Triethylamine, sodium hydride or potassium carbonate as a base in a suitable solvent, e.g. N,N-dimethylformamide or tetrahydrofuran, by traditional thermic method or using microwave technology. Following this process the pyrazolo pyridine derivatives according to Formula (I) are isolated, using standard conditions well known to the person skilled in the art as shown in the Scheme 1.

The Following Abbreviations Refer Respectively to the Definitions Below:

Å (Angström), Ac$_2$O (Acetic anhydride), eq. (equivalent), min (minute), h (hour), g (gram), MHz (Megahertz), mL (milliliter), mm (millimetre), mmol (millimole), mM (millimolar), ng (nanogram), nm (nanometer), rt (room temperature), NADPH (Nicotinamide adenine dinucleotide diphosphate reduced form), BSA (Bovine serum albumin), DCF (2,7-dichlorodihydrofluorescein), DCM (dichloromethane), DIPEA (di-isopropyl ethylamine), DMSO (Dimethyl Sulfoxide), DMF (N,N-Dimethylformamide), DAPI (4,6 Diamidino-2-phenylindole), DPI (Diphenyl-iodonium), cHex (Cyclohexane), EDTA (ethylenediaminetetraacetic acid), EGF (Epidermal Growth Factor), EtOAc (Ethyl acetate), FC (Flash Chromatography on silica gel), HBSS (Hank's Buffered Salt Solution), HPLC (High performance liquid chromatography), H$_2$DCF-DA (2',7'-dichlorodihydrofluorescein diacetate), MEM (2-methoxyethoxymethyl), MS (Mass Spectrometry), NBT (Nitroblue tetrazolium), NMR (Nuclear magnetic resonance), PBS (Phosphate Buffered Saline), PetEther (Petroleum ether), TEA (Triethyl amine), TFA (Trifluoroacetic acid), TGF-β (Tumor Growth Factor beta), THF (Tetrahydrofuran), tBuOK (Potassium tert-butoxide), ROS (Reactive oxygen species), SOD (Superoxide dismutase), SPA (Scintillation proximity assay), TLC (Thin layer chromatography), UV (Ultraviolet).

If the above set of general synthetic methods is not applicable to obtain compounds according to Formula (I) and/or necessary intermediates for the synthesis of compounds of Formula (I), suitable methods of preparation known by a person skilled in the art should be used. In general, the synthesis pathways for any individual compound of Formula (I) will depend on the specific substituents of each molecule and upon the ready availability of intermediates necessary; again such factors being appreciated by those of ordinary skill in the art. For all the protection and deprotection methods, see Philip J. Kocienski, in "Protecting Groups", Georg Thieme Verlag Stuttgart, New York, 1994 and, Theodora W. Greene and Peter G. M. Wuts in "Protective Groups in Organic Synthesis", Wiley Interscience, 3$^{rd}$ Edition 1999.

Compounds of this invention can be isolated in association with solvent molecules by crystallization from evaporation of an appropriate solvent. The pharmaceutically acceptable acid addition salts of the compounds of Formula (I), which contain a basic center, may be prepared in a conventional manner. For example, a solution of the free base may be treated with a suitable acid, either neat or in a suitable solution, and the resulting salt isolated either by filtration or by evaporation under vacuum of the reaction solvent. Pharmaceutically acceptable base addition salts may be obtained in an analogous manner by treating a solution of compound of Formula (I) with a suitable base. Both types of salts may be formed or interconverted using ion-exchange resin techniques.

In the following the present invention shall be illustrated by means of some examples, which are not to be viewed as limiting the scope of the invention.

The HPLC, NMR and MS data provided in the examples described below are obtained as followed: HPLC: column Waters Symmetry C8 50×4.6 mm, Conditions: MeCN/H$_2$O, 5 to 100% (8 min), max plot 230-400 nm; Mass spectra: PE-SCIEX API 150 EX (APCI and ESI), LC/MS spectra: Waters ZMD (ES); $^1$H-NMR: Bruker DPX-300 MHz.

The preparative HPLC purifications are performed with HPLC Waters Prep LC 4000 System equipped with columns Prep Nova-Pak® HR C18 6 μm 60 Å, 40×30 mm (up to 100 mg) or with XTerra® Prep MS C8, 10 μm, 50×300 mm (up to 1 g). All the purifications are performed with a gradient of MeCN/H$_2$O 0.09% TFA; UV detection at 254 nm and 220 nm; flow 20 mL/min (up to 50 mg). TLC Analysis is performed on Merck Precoated 60 F$_{254}$ plates. Purifications by flash chromatography are performed on SiO$_2$ support, using cyclohexane/EtOAc or DCM/MeOH mixtures as eluents.

EXAMPLE 1

Formation of 4-methyl-2-phenyl-5-(thiophen-2-ylmethyl)-1H-pyrazolo[4,3-c]pyridine-3,6(2H,5H)-dione (1) (Compound Ia, Scheme 1)

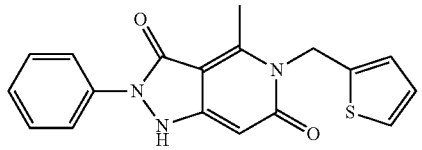 [SMILES: Cc1c2c(=O)n(-c3ccccc3)[nH]c2cc(=O)n1Cc1cccs1]

Following the general methods as outlined in Example 7 below, starting from phenylhydrazine, dimethyl 3-oxopentanedioate, 1,1,1-triethoxyethane and 1-thiophen-2-ylmethanamine, the title compound (1) was isolated as a white solid in 70% yield (98% purity by HPLC). MS (ESI$^+$): 338.6; MS (ESI$^-$): 336.4.

EXAMPLE 2

Formation of 2-(1,3-benzothiazol-2-yl)-5-[2-(1H-imidazol-4-yl)ethyl]-4-methyl-1H-pyrazolo[4,3-c]pyridine-3,6(2H,5H)-dione (2) (Compound Ia, Scheme 1)

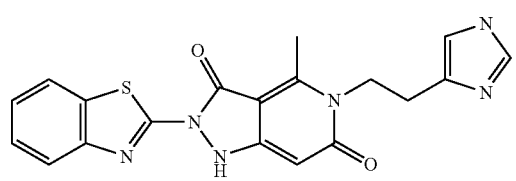 [SMILES: Cc1c2c(=O)n(-c3nc4ccccc4s3)[nH]c2cc(=O)n1CCc1c[nH]cn1]

Following the general methods as outlined in Example 7, starting from 2-hydrazino-1,3-benzothiazole, dimethyl 3-oxopentanedioate, 1,1,1-triethoxyethane and 2-(1H-imidazol-5-yl)ethanamine, the title compound (2) was isolated as a yellow-beige solid in 75% yield (98% purity by HPLC). MS (ESI$^+$): 393.5; MS (ESI$^-$): 391.6.

EXAMPLE 3

Formation of 2-(1,3-benzothiazol-2-yl)-5-[2-(1H-indol-3-yl)ethyl]-4-methyl-1H-pyrazolo[4,3-c]pyridine-3,6(2H,5H)-dione (3) (Compound Ia, Scheme 1)

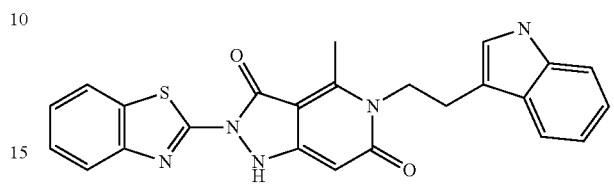

Following the general methods as outlined in Example 7, starting from 2-hydrazino-1,3-benzothiazole, dimethyl 3-oxopentanedioate, 1,1,1-triethoxyethane and 2-(1H-indol-3-yl)ethanamine, the title compound (3) was isolated as a white solid in 76% yield (98% purity by HPLC). MS (ESI$^+$): 442.6; MS (ESI$^-$): 440.7.

EXAMPLE 4

Formation of 2-(1,3-benzothiazol-2-yl)-4-methyl-5-(3-morpholin-4-yl propyl)-1H-pyrazolo[4,3-c]pyridine-3,6(2H,5H)-dione (4) (Compound Ia, Scheme 1)

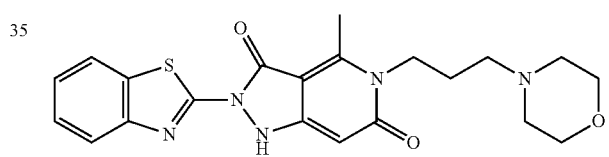

Following the general methods as outlined in Example 7, starting from 2-hydrazino-1,3-benzothiazole, dimethyl 3-oxopentanedioate, 1,1,1-triethoxyethane and 3-morpholin-4-ylpropan-1-amine, the title compound (4) was isolated as a white solid in 72% yield (96% purity by HPLC). MS (ESI$^+$): 426.6; MS (ESI$^-$): 424.7.

EXAMPLE 5

Formation of 5-(furan-2-ylmethyl)-4-methyl-2-phenyl-1H-pyrazolo[4,3-c]pyridine-3,6(2H,5H)-dione (5) (Compound Ia, Scheme 1)

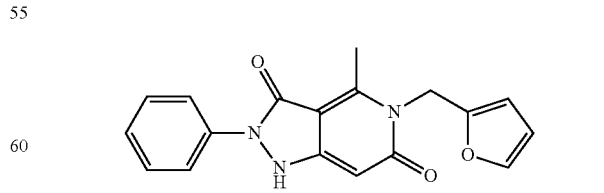

Following the general methods as outlined in Example 7, starting from phenylhydrazine, dimethyl 3-oxopentanedioate, 1,1,1-triethoxyethane and 1-furan-2-ylmethanamine, the title compound (5) was isolated as a white solid in 79% yield (96% purity by HPLC). MS (ESI$^+$): 322.5; MS (ESI$^-$): 320.4.

EXAMPLE 6

Formation of 4-{[2-(1,3-benzothiazol-2-yl)-4-methyl-3,6-dioxo-1,2,3,6-tetrahydro-5H-pyrazolo[4,3-c]pyridin-5-yl]methyl}benzoic acid (6) (Compound Ia, Scheme 1)

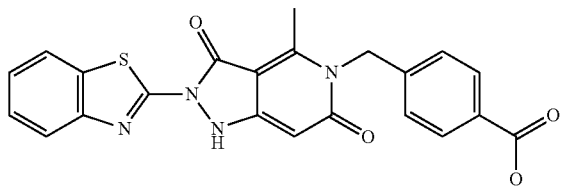 [SMILES: Cc1c2c(=O)n(-c3nc4ccccc4s3)[nH]c2cc(=O)n1Cc1ccc(C(=O)O)cc1]

Following the general methods as outlined in Example 7, starting from 2-hydrazino-1,3-benzothiazole, dimethyl 3-oxopentanedioate, 1,1,1-triethoxyethane and 4-(aminomethyl)benzoic acid, the title compound (6) was isolated as a white solid in 78% yield (99% purity by HPLC). MS (ESI$^+$): 433.5; MS (ESI$^-$): 431.4.

EXAMPLE 7

Formation of 4-methyl-2-phenyl-5-(pyridin-3-ylmethyl)-1H-pyrazolo[4,3-c]pyridine-3,6(2H,5H)-dione (7) (Compound Ia, Scheme 1)

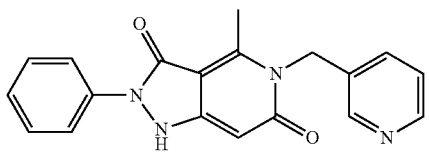 [SMILES: Cc1c2c(=O)n(-c3ccccc3)[nH]c2cc(=O)n1Cc1cccnc1]

a) Methyl (5-hydroxy-1-phenyl-1H-pyrazol-3-yl)acetate (Compound of Formula (IV), Scheme 1). The mixture of dimethyl 3-oxopentanedioate (10 mmol, 1.74 g) and phenylhydrazine (10 mmol, 1.08 g) in dry benzene (50 ml) was refluxed for 8 h, then solvent was removed in vacuo and the title compound was separated by recrystallization from i-PrOH (20 ml). Yield: 80%. $^1$HNMR (500 MHz, DMSO-d6, ppm): 3.49 (2H, s), 3.68 (3H, s), 5.43 (1H, s), 7.12 (1H, t, 7.4 Hz), 7.35 (2H, t, 7.6 Hz), 7.78 (2H, d, 7.9 Hz), 11.1 (1H, bs)

b) Methyl [(4Z)-4-(1-ethoxyethylidene)-5-oxo-1-phenyl-4,5-dihydro-1H-pyrazol-3-yl]acetate (Compound of Formula (VII), Scheme 1). The mixture of the above obtained methyl (5-hydroxy-1-phenyl-1H-pyrazol-3-yl)acetate (Compound of Formula (IV), 1.85 g), acetic anhydride (1.00 ml) and MeC(OEt)$_3$ (2.50 ml) was refluxed for 1 h. and left overnight at an ambient temperature. Resulting precipitate was collected by filtration and washed with ethyl ether (10 ml) in order to obtain crude product methyl [(4Z)-4-(1-ethoxyethylidene)-5-oxo-1-phenyl-4,5-dihydro-1H-pyrazol-3-yl]acetate (1.20 g, 80% purity) in 50% yields. $^1$HNMR (400 MHz, CDCl3, ppm): 1.42 (3H, t, 7.1 Hz), 2.78 (3H, s), 3.73 (3H, s), 3.76 (2H, s), 4.31 (2H, q, 6.9 Hz), 7.16 (1H, t, 7.2 Hz), 7.37 (2H, t, 7.6 Hz), 7.97 (2H, d, 8.0 Hz). MS (ESI$^+$): 303.3; MS (ESI$^-$): 301.2.

c) Methyl [(4Z)-5-oxo-1-phenyl-4-{1-[(pyridin-3-ylmethyl)amino]ethylidene}-4,5-dihydro-1H-pyrazol-3-yl]acetate (Compound of Formula (VIII), Scheme 1). The mixture of the above obtained methyl [(4Z)-4-(1-ethoxyethylidene)-5-oxo-1-phenyl-4,5-dihydro-1H-pyrazol-3-yl]acetate (Compound of Formula (VII), 1.20 g) and 3-aminomethylpyridine (0.45 g) was refluxed in toluene (20 ml) for 0.5 h and left overnight at an ambient temperature. Resulting expected product methyl [(4Z)-5-oxo-1-phenyl-4-{1-[(pyridin-3-ylmethyl)amino]ethylidene}-4,5-dihydro-1H-pyrazol-3-yl]acetate (0.87 g) was collected by filtration and washed with ethyl ether (20 ml). Yield 60%. $^1$HNMR (400 MHz, CDCl3, ppm): 2.38 (3H, s), 3.71 (3H, s), 3.82 (2H, s), 4.71 (2H, d, 5.9 Hz), 7.18 (1H, t, 7.2 Hz), 7.38 (3H, m), 7.70 (1H, d, 7.7 Hz), 7.97 (2H, d, 8.0 Hz), 8.63 (2H, bs), 12.17 (1H, bs). MS (ESI$^+$): 365.3; MS (ESI$^-$): 363.5.

d) 4-methyl-2-phenyl-5-(pyridin-3-ylmethyl)-1H-pyrazolo[4,3-c]pyridine-3,6(2H,5H)-dione (7) (Compound of Formula (Ia), Scheme 1)

An isopropanolic solution of NaOi-Pr, obtained by dissolving of sodium (0.055 g) in i-PrOH (50 ml), was treated with the above obtained methyl [(4Z)-5-oxo-1-phenyl-4-{1-[(pyridin-3-ylmethyl)amino]ethylidene}-4,5-dihydro-1H-pyrazol-3-yl]acetate (Compound of Formula (VIII), 0.87 g). The reaction mixture was refluxed for 9 h, then cooled and neutralized to pH 7 with aqueous HCl solution (20%). The precipitate formed was filtered off, washed with water (20 ml) and air-dried. 0.46 g of chromatographically pure product was obtained in yield of 58%. $^1$HNMR (400 MHz, DMSO-d6, ppm): 2.77 (3H, s), 5.38 (2H, s), 5.82 (1H, s), 7.18 (1H, t, 7.5 Hz), 7.36 (1H, m), 7.45 (2H, t, 7.6 Hz), 7.56 (1H, d, 7.7 Hz), 7.73 (2H, d, 8.0 Hz), 8.49 (2H, bs), 10.8 (1H, bs). MS (ESI$^+$): 333.5; MS (ESI$^-$): 331.5.

EXAMPLE 8

Formation of 4-methyl-2-phenyl-5-(2-phenylethyl)-1H-pyrazolo[4,3-c]pyridine-3,6(2H,5H)-dione (8) (Compound Ia, Scheme 1)

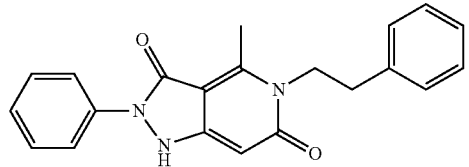 [SMILES: Cc1c2c(=O)n(-c3ccccc3)[nH]c2cc(=O)n1CCc1ccccc1]

Following the general methods as outlined in Example 7, starting from phenylhydrazine, dimethyl 3-oxopentanedioate, 1,1,1-triethoxyethane and 2-phenylethanamine, the title compound (8) was isolated as a white solid in 80% yield (98% purity by HPLC). MS (ESI$^+$): 346.7; MS (ESI$^-$): 344.5.

EXAMPLE 9

Formation of 5-[2-(4-acetylpiperazin-1-yl)ethyl]-2-(1,3-benzothiazol-2-yl)-4-methyl-1H-pyrazolo[4,3-c]pyridine-3,6(2H,5H)-dione (9) (Compound Ia, Scheme 1)

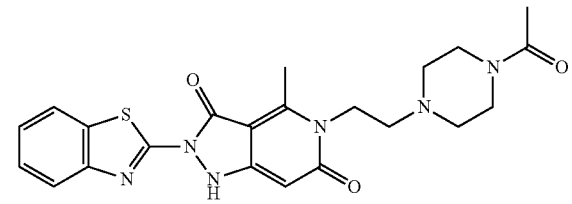 [SMILES: CC(=O)N1CCN(CCn2c(C)c3c(=O)n(-c4nc5ccccc5s4)[nH]c3cc2=O)CC1]

Following the general methods as outlined in Example 7, starting from 2-hydrazino-1,3-benzothiazole, dimethyl 3-oxopentanedioate, 1,1,1-triethoxyethane and 2-(4-acetylpiperazin-1-yl)ethanamine, the title compound (9) was

EXAMPLE 10

Formation of 2-(1,3-benzothiazol-2-yl)-4-methyl-5-(2-methylbutyl)-1H-pyrazolo[4,3-c]pyridine-3,6(2H,5H)-dione (10) (Compound Ia, Scheme 1)

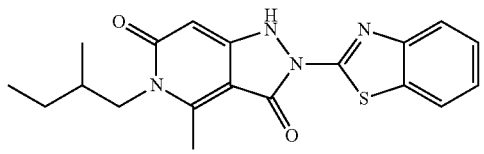 [SMILES: CCC(C)Cn1c(C)c2c(=O)n(-c3nc4ccccc4s3)[nH]c2cc1=O]

Following the general methods as outlined in Example 7, starting from 2-hydrazino-1,3-benzothiazole, dimethyl 3-oxopentanedioate, 1,1,1-triethoxyethane and 2-methylbutan-1-amine, the title compound (10) was isolated as a white solid in 77% yield (99% purity by HPLC). MS (ESI$^+$): 369.7; MS (ESI$^-$): 367.8.

EXAMPLE 11

Formation of 2-(1,3-benzothiazol-2-yl)-5-[2-(4-methoxyphenyl)ethyl]-4-methyl-1H-pyrazolo[4,3-c]pyridine-3,6(2H,5H)-dione (11) (Compound Ia, Scheme 1)

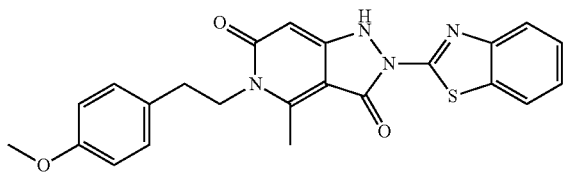 [SMILES: COc1ccc(CCn2c(C)c3c(=O)n(-c4nc5ccccc5s4)[nH]c3cc2=O)cc1]

Following the general methods as outlined in Example 7, starting from 2-hydrazino-1,3-benzothiazole, dimethyl 3-oxopentanedioate, 1,1,1-triethoxyethane and 2-(4-methoxyphenyl)ethanamine, the title compound (11) was isolated as a white solid in 79% yield (97% purity by HPLC). MS (ESI$^+$): 433.6; MS (ESI$^-$): 431.7.

EXAMPLE 12

Formation of 2-(1,3-benzothiazol-2-yl)-5-[2-(4-hexanoylpiperazin-1-yl)ethyl]-4-methyl-1H-pyrazolo[4,3-c]pyridine-3,6(2H,5H)-dione (12) (Compound Ia, Scheme 1)

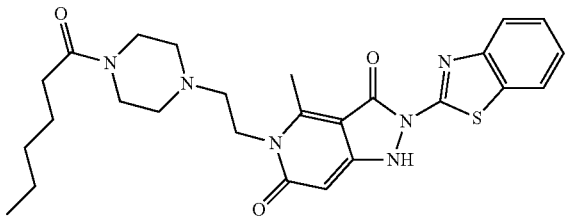 [SMILES: CCCCCC(=O)N1CCN(CCn2c(C)c3c(=O)n(-c4nc5ccccc5s4)[nH]c3cc2=O)CC1]

Following the general methods as outlined in Example 7, starting from 2-hydrazino-1,3-benzothiazole, dimethyl 3-oxopentanedioate, 1,1,1-triethoxyethane and 2-(4-hexanoylpiperazin-1-yl)ethanamine, the title compound (12) was isolated as a beige solid in 71% yield (95% purity by HPLC). MS (ESI$^+$): 508.8; MS (ESI$^-$): 506.6.

EXAMPLE 13

Formation of 2-(1,3-benzothiazol-2-yl)-1-benzyl-5-(furan-2-ylmethyl)-4-methyl-1H-pyrazolo[4,3-c]pyridine-3,6(2H,5H)-dione (13) (Compound Ib, Scheme 1)

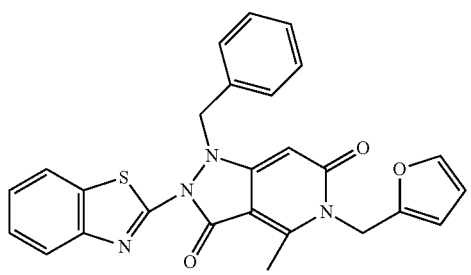 [SMILES: Cc1c2c(=O)n(-c3nc4ccccc4s3)n(Cc3ccccc3)c2cc(=O)n1Cc1ccco1]

Following the general methods as outlined in Example 7, starting from 2-hydrazino-1,3-benzothiazole, dimethyl 3-oxopentanedioate, 1,1,1-triethoxyethane, 1-furan-2-yl-methanamine and alkylation with (chloromethyl)benzene (1 eq.) and the corresponding intermediate compound according to Formula (Ia) (1 eq.) in presence of triethylamine (1.5 eq.) in refluxing THF, the title compound (13) was isolated as a beige solid in 61% yield (97% purity by HPLC). MS (ESI$^+$): 469.6; MS (ESI$^-$): 467.3.

EXAMPLE 14

Formation of 5-[2-(1H-indol-3-yl)ethyl]-4-methyl-1-(3-methylbenzyl)-2-phenyl-1H-pyrazolo[4,3-c]pyridine-3,6(2H,5H)-dione (14) (Compound Ib, Scheme 1)

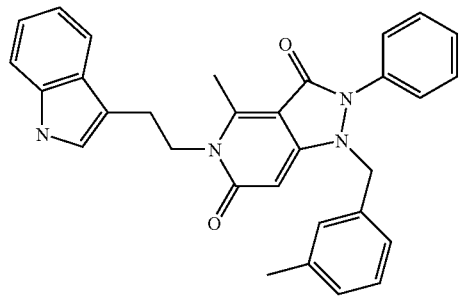 [SMILES: Cc1cccc(Cn2c3cc(=O)n(CCc4c[nH]c5ccccc45)c(C)c3c(=O)n2-c2ccccc2)c1]

Following the general methods as outlined in Examples 7 and 13, starting from phenylhydrazine, dimethyl 3-oxopentanedioate, 1,1,1-triethoxyethane, 2-(1H-indol-3-yl)ethanamine and 1-(chloromethyl)-3-methylbenzene, the title compound (14) was isolated as a white solid in 58% yield (98% purity by HPLC). MS (ESI$^+$): 489.6; MS (ESI$^-$): 487.5.

EXAMPLE 15

Formation of 1-(4-fluorobenzyl)-5-[2-(1H-indol-3-yl)ethyl]-4-methyl-2-phenyl-1H-pyrazolo[4,3-c]pyridine-3,6(2H,5H)-dione (15) (Compound Ib, Scheme 1)

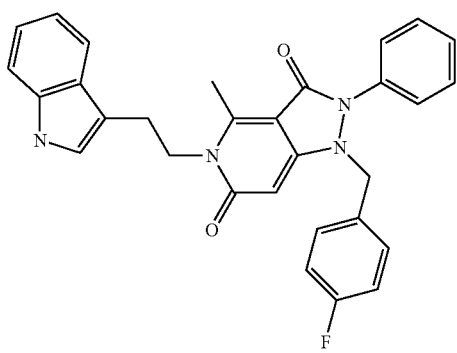 [SMILES: Cc1c2c(=O)n(-c3ccccc3)n(Cc3ccc(F)cc3)c2cc(=O)n1CCc1c[nH]c2ccccc12]

Following the general methods as outlined in Examples 7 and 13, starting from phenylhydrazine, dimethyl 3-oxopentanedioate, 1,1,1-triethoxyethane, 2-(1H-indol-3-yl)ethanamine and 1-(chloromethyl)-4-fluorobenzene, the title compound (15) was isolated as a white solid in 55% yield (95% purity by HPLC). MS (ESI$^+$): 493.6; MS (ESI$^-$): 491.6.

EXAMPLE 16

Formation of 1-(2-chlorobenzyl)-4-methyl-5-[3-(2-oxopyrrolidin-1-yl) propyl]-2-phenyl-1H-pyrazolo[4,3-c]pyridine-3,6(2H,5H)-dione (16) (Compound Ib, Scheme 1)

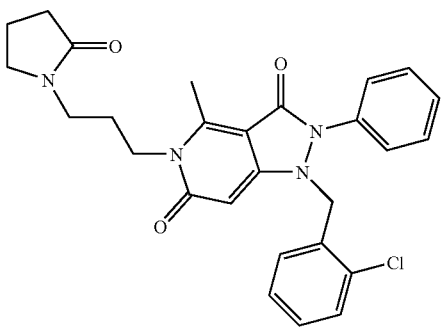 [SMILES: Cc1c2c(=O)n(-c3ccccc3)n(Cc3ccccc3Cl)c2cc(=O)n1CCCN1CCCC1=O]

Following the general methods as outlined in Examples 7 and 13, starting from phenylhydrazine, dimethyl 3-oxopentanedioate, 1,1,1-triethoxyethane, 1-(3-aminopropyl)pyrrolidin-2-one and 1-chloro-2-(chloromethyl)benzene, the title compound (16) was isolated as a white solid in 51% yield (98% purity by HPLC). MS (ESI$^+$): 492.1; MS (ESI$^-$): 490.0.

EXAMPLE 17

Formation of 2-(1,3-benzothiazol-2-yl)-1-benzyl-4-methyl-5-(tetrahydro furan-2-ylmethyl)-1H-pyrazolo[4,3-c]pyridine-3,6(2H,5H)-dione (17) (Compound Ib, Scheme 1)

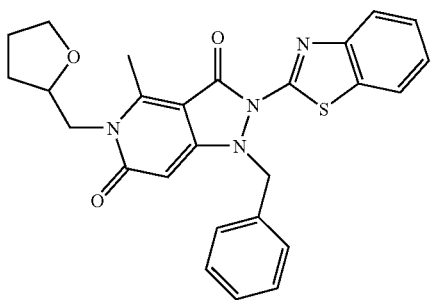 [SMILES: Cc1c2c(=O)n(-c3nc4ccccc4s3)n(Cc3ccccc3)c2cc(=O)n1CC1CCCO1]

Following the general methods as outlined in Examples 7 and 13, starting from 2-hydrazino-1,3-benzothiazole, dimethyl 3-oxopentanedioate, 1,1,1-triethoxyethane, 1-(tetrahydrofuran-2-yl)methanamine and (chloromethyl)benzene, the title compound (17) was isolated as a beige solid in 61% yield (97% purity by HPLC). MS (ESI$^+$): 473.7; MS (ESI$^-$): 471.6.

EXAMPLE 18

Formation of 1-(4-chlorobenzyl)-5-[2-(1H-imidazol-4-yl)ethyl]-4-methyl-2-phenyl-1H-pyrazolo[4,3-c]pyridine-3,6(2H,5H)-dione (18) (Compound Ib, Scheme 1)

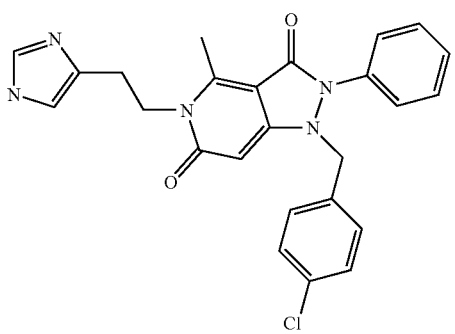 [SMILES: Cc1c2c(=O)n(-c3ccccc3)n(Cc3ccc(Cl)cc3)c2cc(=O)n1CCc1c[nH]cn1]

Following the general methods as outlined in Examples 7 and 13, starting from phenylhydrazine, dimethyl 3-oxopentanedioate, 1,1,1-triethoxyethane, 2-(1H-imidazol-5-yl)ethanamine and 1-chloro-4-(chloromethyl)benzene, the title compound (18) was isolated as a beige solid in 63% yield (98% purity by HPLC). MS (ESI$^+$): 461.0; MS (ESI$^-$): 459.0.

EXAMPLE 19

Formation of 5-(1,3-benzodioxol-5-ylmethyl)-4-methyl-2-phenyl-1H-pyrazolo[4,3-c]pyridine-3,6(2H,5H)-dione (19) (Compound Ia, Scheme 1)

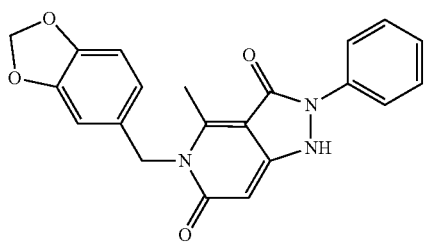 [SMILES: Cc1c2c(=O)n(-c3ccccc3)[nH]c2cc(=O)n1Cc1ccc2c(c1)OCO2]

Following the general methods as outlined in Example 7a), starting from phenylhydrazine, dimethyl 3-oxopentanedioate, 1,1,1-triethoxyethane and 1-(1,3-benzodioxol-5-yl)methanamine, the title compound (19) was isolated as a beige solid in 78% yield (99% purity by HPLC). MS (ESI$^+$): 376.5; MS (ESI$^-$): 374.5.

EXAMPLE 20

Formation of 5-benzyl-4-methyl-2-phenyl-1H-pyrazolo[4,3-c]pyridine-3,6(2H,5H)-dione (20) (Compound Ia, Scheme 1)

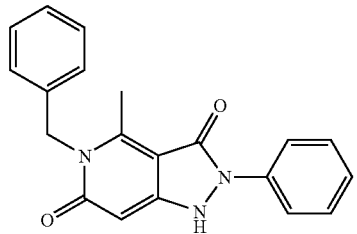 [SMILES: Cc1c2c(=O)n(-c3ccccc3)[nH]c2cc(=O)n1Cc1ccccc1]

Following the general methods as outlined in Example 7a), starting from phenylhydrazine, dimethyl 3-oxopentanedioate, 1,1,1-triethoxyethane and benzylamine, the title compound (20) was isolated as a beige solid in 79% yield (99% purity by HPLC). MS (ESI$^+$): 332.5; MS (ESI$^-$): 330.4.

EXAMPLE 21

Formation of 5-benzyl-2-(4-fluorophenyl)-4-methyl-1H-pyrazolo[4,3-c]pyridine-3,6(2H,5H)-dione (21) (Compound Ia, Scheme 1)

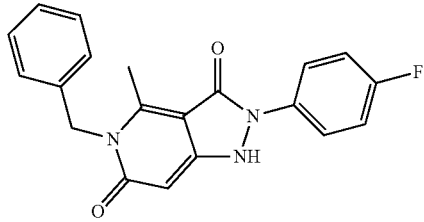 [SMILES: Cc1c2c(=O)n(-c3ccc(F)cc3)[nH]c2cc(=O)n1Cc1ccccc1]

Following the general methods as outlined in Example 7a), starting from (4-fluorophenyl)hydrazine, dimethyl 3-oxopentanedioate, 1,1,1-triethoxyethane and benzylamine, the title compound (21) was isolated as a white solid in 86% yield (99% purity by HPLC). MS (ESI$^+$): 350.5; MS (ESI$^-$): 348.6.

EXAMPLE 22

Formation of 5-benzyl-2-(4-methoxyphenyl)-4-methyl-1H-pyrazolo[4,3-c]pyridine-3,6(2H,5H)-dione (22) (Compound Ia, Scheme 1)

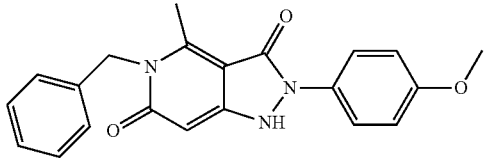 [SMILES: COc1ccc(-n2[nH]c3cc(=O)n(Cc4ccccc4)c(C)c3c2=O)cc1]

Following the general methods as outlined in Example 7a), starting from (4-methoxyphenyl)hydrazine, dimethyl 3-oxopentanedioate, 1,1,1-triethoxyethane and benzylamine, the title compound (22) was isolated as a beige solid in 78% yield (95% purity by HPLC). MS (ESI$^+$): 362.6; MS (ESI$^-$): 360.5.

EXAMPLE 23

Formation of 2-(1,3-benzothiazol-2-yl)-4-methyl-5-morpholin-4-yl-1H-pyrazolo[4,3-c]pyridine-3,6(2H,5H)-dione (23) (Compound Ia, Scheme 1)

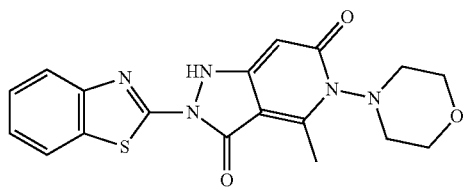 [SMILES: Cc1c2c(=O)n(-c3nc4ccccc4s3)[nH]c2cc(=O)n1N1CCOCC1]

Following the general methods as outlined in Example 7a), starting from 2-hydrazino-1,3-benzothiazole, dimethyl 3-oxopentanedioate, 1,1,1-triethoxyethane and morpholin-4-amine, the title compound (23) was isolated as a yellowish solid in 81% yield (99% purity by HPLC). MS (ESI$^+$): 384.5; MS (ESI$^-$): 382.5.

EXAMPLE 24

Formation of 5-benzyl-4-methyl-2-(4-nitrophenyl)-1H-pyrazolo[4,3-c]pyridine-3,6(2H,5H)-dione (24) (Compound Ia, Scheme 1)

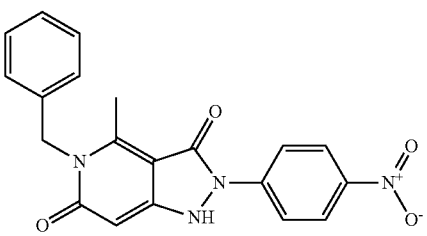 [SMILES: Cc1c2c(=O)n(-c3ccc([N+](=O)[O-])cc3)[nH]c2cc(=O)n1Cc1ccccc1]

Following the general methods as outlined in Example 7a), starting from (4-nitrophenyl)hydrazine, dimethyl 3-oxopentanedioate, 1,1,1-triethoxyethane and benzylamine, the title compound (24) was isolated as a yellow solid in 72% yield (96% purity by HPLC). MS (ESI$^+$): 377.6; MS (ESI$^-$): 375.5.

EXAMPLE 25

Formation of 2-(1,3-benzothiazol-2-yl)-4-methyl-1-(3-methylbenzyl)-5-(3-morpholin-4-ylpropyl)-1H-pyrazolo[4,3-c]pyridine-3,6(2H,5H)-dione (25) (Compound Ib, Scheme 1)

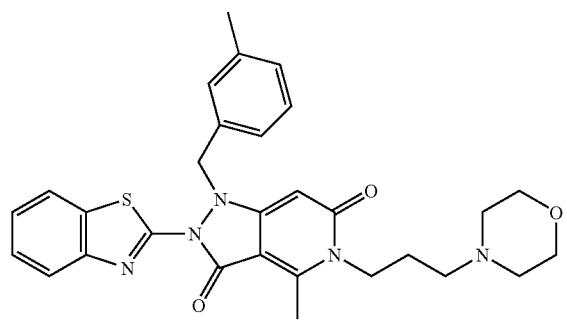 [SMILES: Cc1cccc(Cn2c3cc(=O)n(CCCN4CCOCC4)c(C)c3c(=O)n2-c2nc3ccccc3s2)c1]

Following the general methods as outlined in Examples 7 and 13, starting from 2-hydrazino-1,3-benzothiazole, dimethyl 3-oxopentanedioate, 1,1,1-triethoxyethane, 3-morpholin-4-ylpropan-1-amine and 1-(chloromethyl)-3-methylbenzene, the title compound (25) was isolated as a white solid in 68% yield (98% purity by HPLC). MS (ESI$^+$): 530.9; MS (ESI$^-$): 528.6.

EXAMPLE 26

Formation of 2-(1,3-benzothiazol-2-yl)-1-(4-fluorobenzyl)-4-methyl-5-(3-morpholin-4-ylpropyl)-1H-pyrazolo[4,3-c]pyridine-3,6(2H,5H)-dione (26) (Compound Ib, Scheme 1)

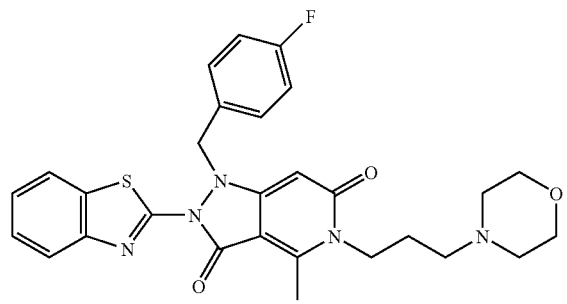 [SMILES: Cc1c2c(=O)n(-c3nc4ccccc4s3)n(Cc3ccc(F)cc3)c2cc(=O)n1CCCN1CCOCC1]

Following the general methods as outlined in Examples 7 and 13, starting from 2-hydrazino-1,3-benzothiazole, dimethyl 3-oxopentanedioate, 1,1,1-triethoxyethane, 3-morpholin-4-ylpropan-1-amine and 1-(chloromethyl)-4-fluorobenzene, the title compound (26) was isolated as a beige solid in 54% yield (98% purity by HPLC). MS (ESI$^+$): 534.9; MS (ESI$^-$): 532.6.

EXAMPLE 27

Formation of 2-(1,3-benzothiazol-2-yl)-4-methyl-1-(4-methylbenzyl)-5-(3-morpholin-4-ylpropyl)-1H-pyrazolo[4,3-c]pyridine-3,6(2H,5H)-dione (27) (Compound Ib, Scheme 1)

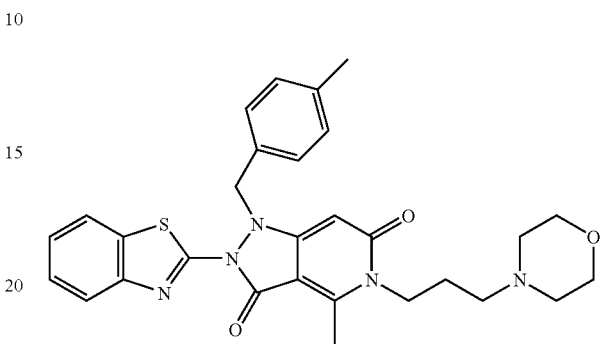

Following the general methods as outlined in Examples 7 and 13, starting from 2-hydrazino-1,3-benzothiazole, dimethyl 3-oxopentanedioate, 1,1,1-triethoxyethane, 3-morpholin-4-ylpropan-1-amine and 1-(bromomethyl)-4-methylbenzene, the title compound (27) was isolated as a beige solid in 62% yield (98% purity by HPLC). MS (ESI$^+$): 530.8; MS (ESI$^-$): 528.6.

EXAMPLE 28

Formation of 2-(1,3-benzothiazol-2-yl)-1-(2-chlorobenzyl)-4-methyl-5-morpholin-4-yl-1H-pyrazolo[4,3-c]pyridine-3,6(2H,5H)-dione (28) (Compound Ib, Scheme 1)

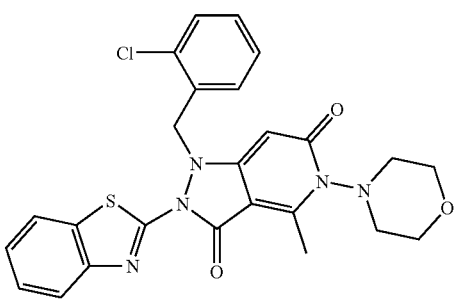 [SMILES: Cc1c2c(=O)n(-c3nc4ccccc4s3)n(Cc3ccccc3Cl)c2cc(=O)n1N1CCOCC1]

Following the general methods as outlined in Examples 7 and 13, starting from 2-hydrazino-1,3-benzothiazole, dimethyl 3-oxopentanedioate, 1,1,1-triethoxyethane, morpholin-4-amine and 1-chloro-2-(chloromethyl)benzene, the title compound (28) was isolated as a beige solid in 56% yield (98% purity by HPLC). MS (ESI$^+$): 509.1; MS (ESI$^-$): 507.0.

EXAMPLE 29

Formation of 2-(1,3-benzothiazol-2-yl)-1-(4-bromobenzyl)-4-methyl-5-(2-morpholin-4-ylethyl)-1H-pyrazolo[4,3-c]pyridine-3,6(2H,5H)-dione (29) (Compound Ib, Scheme 1)

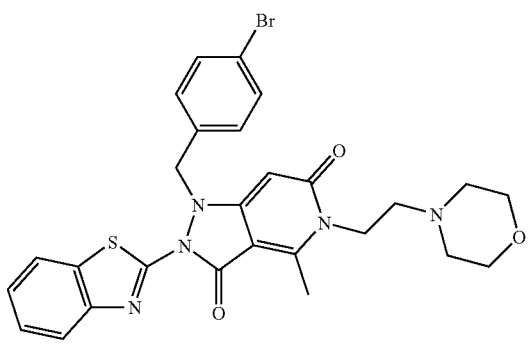 [SMILES: Cc1c2c(=O)n(-c3nc4ccccc4s3)n(Cc3ccc(Br)cc3)c2cc(=O)n1CCN1CCOCC1]

Following the general methods as outlined in Examples 7 and 13, starting from 2-hydrazino-1,3-benzothiazole, dimethyl 3-oxopentanedioate, 1,1,1-triethoxyethane, 2-morpholin-4-ylethanamine and 1-bromo-4-(chloromethyl)benzene, the title compound (29) was isolated as a beige solid in 50% yield (98% purity by HPLC). MS (ESI$^+$): 581.7; MS (ESI$^-$): 579.4.

EXAMPLE 30

Formation of 2-[2-(1,3-benzothiazol-2-yl)-4-methyl-5-(3-morpholin-4-ylpropyl)-3,6-dioxo-2,3,5,6-tetrahydro-1H-pyrazolo[4,3-c]pyridin-1-yl]-N-phenylacetamide (30) (Compound Ib, Scheme 1)

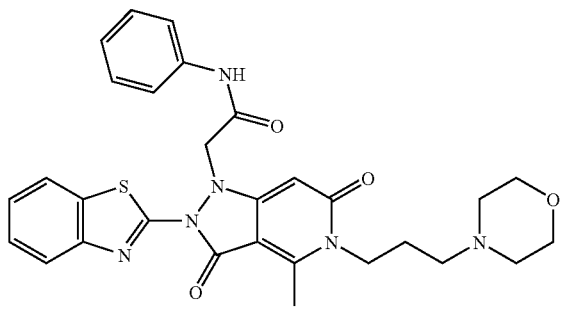 [SMILES: Cc1c2c(=O)n(-c3nc4ccccc4s3)n(CC(=O)Nc3ccccc3)c2cc(=O)n1CCCN1CCOCC1]

Following the general methods as outlined in Examples 7 and 13, starting from 2-hydrazino-1,3-benzothiazole, dimethyl 3-oxopentanedioate, 1,1,1-triethoxyethane, 3-morpholin-4-ylpropan-1-amine and 2-bromo-N-phenylacetamide, the title compound (30) was isolated as a beige solid in 67% yield (98% purity by HPLC). MS (ESI$^+$): 559.8; MS (ESI$^-$): 557.4.

EXAMPLE 31

Formation of 4-methyl-2-phenyl-5-(tetrahydrofuran-2-ylmethyl)-1H-pyrazolo[4,3-c]pyridine-3,6(2H,5H)-dione (31) (Compound Ia, Scheme 1)

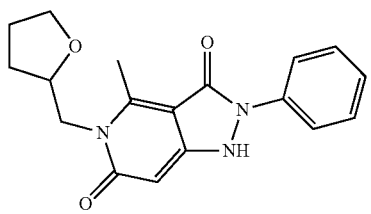 [SMILES: Cc1c2c(=O)n(-c3ccccc3)[nH]c2cc(=O)n1CC1CCCO1]

Following the general methods as outlined in Example 7a), starting from phenylhydrazine, dimethyl 3-oxopentanedioate, 1,1,1-triethoxyethane and 1-(tetrahydrofuran-2-yl)methanamine, the title compound (31) was isolated as a white solid in 78% yield (99% purity by HPLC). MS (ESI$^+$): 326.5; MS (ESI$^-$): 324.4.

EXAMPLE 32

Formation of 2-(1,3-benzothiazol-2-yl)-4-methyl-5-(2-phenylethyl)-1H-pyrazolo[4,3-c]pyridine-3,6(2H,5H)-dione (32) (Compound Ia, Scheme 1)

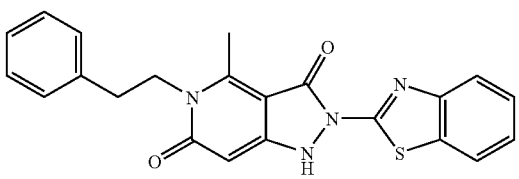 [SMILES: Cc1c2c(=O)n(-c3nc4ccccc4s3)[nH]c2cc(=O)n1CCc1ccccc1]

Following the general methods as outlined in Example 7a), starting from 2-hydrazino-1,3-benzothiazole, dimethyl 3-oxopentanedioate, 1,1,1-triethoxyethane and 2-phenylethanamine, the title compound (32) was isolated as a beige solid in 64% yield (97% purity by HPLC). MS (ESI$^+$): 403.7; MS (ESI$^-$): 401.5.

EXAMPLE 33

Formation of 5-[2-(1H-indol-3-yl)ethyl]-4-methyl-2-phenyl-1H-pyrazolo[4,3-c]pyridine-3,6(2H,5H)-dione (33) (Compound Ia, Scheme 1)

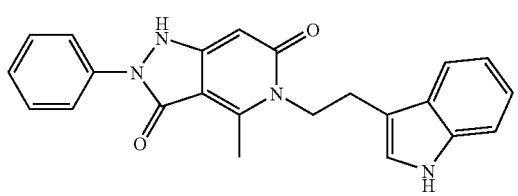 [SMILES: Cc1c2c(=O)n(-c3ccccc3)[nH]c2cc(=O)n1CCc1c[nH]c2ccccc12]

Following the general methods as outlined in Example 7a), starting from phenylhydrazine, dimethyl 3-oxopentanedioate, 1,1,1-triethoxyethane and 2-(1H-indol-3-yl)ethanamine, the title compound (33) was isolated as a beige solid in 82% yield (99% purity by HPLC). MS (ESI$^+$): 335.5; MS (ESI$^-$): 333.3.

EXAMPLE 34

Formation of 4-methyl-5-morpholin-4-yl-2-phenyl-1H-pyrazolo[4,3-c]pyridine-3,6(2H,5H)-dione (34) (Compound Ia, Scheme 1)

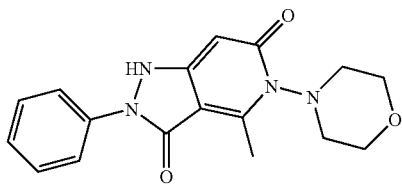 [SMILES: Cc1c2c(=O)n(-c3ccccc3)[nH]c2cc(=O)n1N1CCOCC1]

Following the general methods as outlined in Example 7a), starting from phenylhydrazine, dimethyl 3-oxopentanedioate, 1,1,1-triethoxyethane and morpholin-4-amine, the title compound (34) was isolated as a white solid in 87% yield (99% purity by HPLC). MS (ESI$^+$): 327.6; MS (ESI$^-$): 325.4.

EXAMPLE 35

Formation of 2-(1,3-benzothiazol-2-yl)-1-(2-chlorobenzyl)-4-methyl-5-(3-morpholin-4-ylpropyl)-1H-pyrazolo[4,3-c]pyridine-3,6(2H,5H)-dione (35) (Compound Ib, Scheme 1)

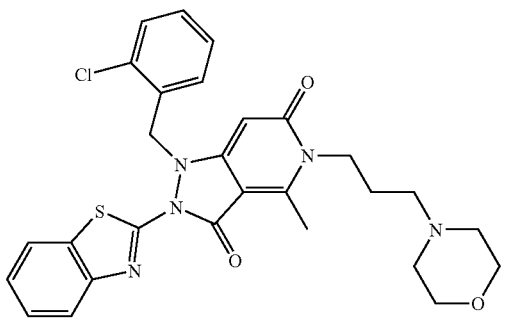 [SMILES: Cc1c2c(=O)n(-c3nc4ccccc4s3)n(Cc3ccccc3Cl)c2cc(=O)n1CCCN1CCOCC1]

Following the general methods as outlined in Examples 7 and 13, starting from 2-hydrazino-1,3-benzothiazole, dimethyl 3-oxopentanedioate, 1,1,1-triethoxyethane, 3-morpholin-4-ylpropan-1-amine and 1-chloro-2-(chloromethyl)benzene, the title compound (35) was isolated as a beige solid in 61% yield (98% purity by HPLC). MS (ESI$^+$): 551.2; MS (ESI$^-$): 549.4.

EXAMPLE 36

Formation of 5-benzyl-4-ethyl-2-(4-fluorophenyl)-1H-pyrazolo[4,3-c]pyridine-3,6(2H,5H)-dione (36) (Compound Ia, Scheme 1)

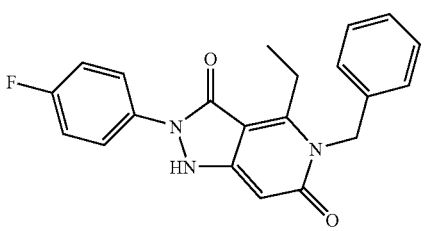 [SMILES: CCc1c2c(=O)n(-c3ccc(F)cc3)[nH]c2cc(=O)n1Cc1ccccc1]

Following the general methods as outlined in Example 7a), starting from (4-fluorophenyl)hydrazine, dimethyl 3-oxopentanedioate, 1,1,1-triethoxyethane and benzylamine, the title compound (36) was isolated as a yellowish solid in 80% yield (96% purity by HPLC). MS (ESI$^+$): 364.5; MS (ESI$^-$): 362.2.

EXAMPLE 37

Formation of 4-ethyl-2-(4-fluorophenyl)-5-(2-phenylethyl)-1H-pyrazolo[4,3-c]pyridine-3,6(2H,5H)-dione (37) (Compound Ia, Scheme 1)

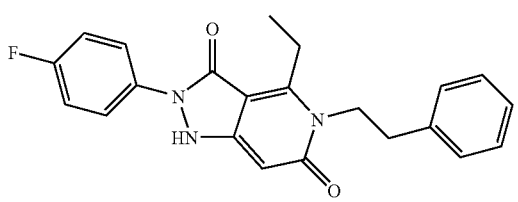 [SMILES: CCc1c2c(=O)n(-c3ccc(F)cc3)[nH]c2cc(=O)n1CCc1ccccc1]

Following the general methods as outlined in Example 7a), starting from (4-fluorophenyl)hydrazine, dimethyl 3-oxopentanedioate, 1,1,1-triethoxypropane and 2-phenylethanamine, the title compound (37) was isolated as a white solid in 83% yield (97% purity by HPLC). MS (ESI$^+$): 378.5; MS (ESI$^-$): 376.4.

EXAMPLE 38

Formation of 4-ethyl-2-(4-fluorophenyl)-5-morpholin-4-yl-1H-pyrazolo[4,3-c]pyridine-3,6(2H,5H)-dione (38) (Compound Ia, Scheme 1)

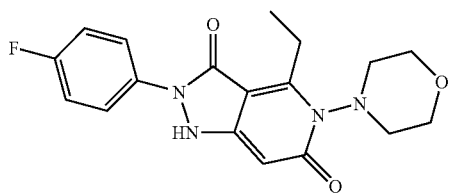 [SMILES: CCc1c2c(=O)n(-c3ccc(F)cc3)[nH]c2cc(=O)n1N1CCOCC1]

Following the general methods as outlined in Example 7a), starting from (4-fluorophenyl)hydrazine, dimethyl 3-oxopentanedioate, 1,1,1-triethoxypropane and morpholin-4-amine, the title compound (38) was isolated as a beige solid in 77% yield (99% purity by HPLC). MS (ESI$^+$): 358.7; MS (ESI$^-$): 356.2.

EXAMPLE 39

Formation of 4-methyl-5-(2-morpholin-4-ylethyl)-2-phenyl-1H-pyrazolo[4,3-c]pyridine-3,6(2H,5H)-dione (39) (Compound Ia, Scheme 1)

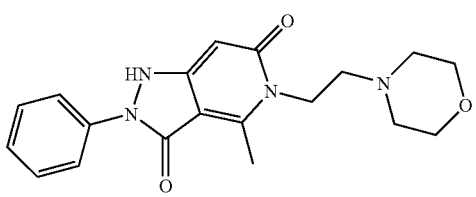 [SMILES: Cc1c2c(=O)n(-c3ccccc3)[nH]c2cc(=O)n1CCN1CCOCC1]

Following the general methods as outlined in Example 7a), starting from phenylhydrazine, dimethyl 3-oxopentanedioate, 1,1,1-triethoxyethane and 2-morpholin-4-ylethanamine, the title compound (39) was isolated as a beige solid in 63% yield (95% purity by HPLC). MS (ESI$^+$): 355.5; MS (ESI$^-$): 353.5.

EXAMPLE 40

Formation of 4-ethyl-5-morpholin-4-yl-2-phenyl-1H-pyrazolo[4,3-c]pyridine-3,6(2H,5H)-dione (40) (Compound Ia, Scheme 1)

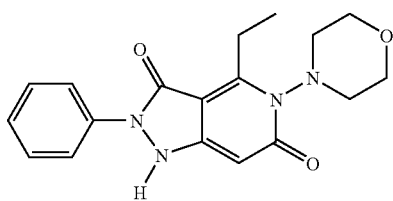 [SMILES: CCc1c2c(=O)n(-c3ccccc3)[nH]c2cc(=O)n1N1CCOCC1]

Following the general methods as outlined in Example 7a), starting from phenylhydrazine, dimethyl 3-oxopentanedioate, 1,1,1-triethoxypropane and morpholin-4-amine, the title compound (40) was isolated as a white solid in 89% yield (98% purity by HPLC). MS (ESI$^+$): 341.8; MS (ESI$^-$): 339.4.

EXAMPLE 41

Formation of 2-(2-chlorophenyl)-4-methyl-5-(pyridin-2-ylmethyl)-1H-pyrazolo[4,3-c]pyridine-3,6(2H,5H)-dione (41) (Compound Ia, Scheme 1)

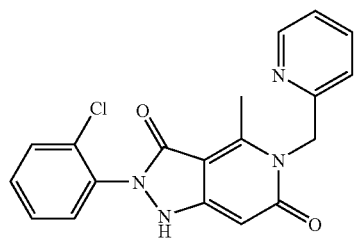

Following the general methods as outlined in Example 7a), starting from (2-chlorophenyl)hydrazine, dimethyl 3-oxopentanedioate, 1,1,1-triethoxyethane and 1-pyridin-2-ylmethanamine, the title compound (41) was isolated as a yellow solid in 81% yield (99% purity by HPLC). MS (ESI$^+$): 367.9; MS (ESI$^-$): 365.7.

EXAMPLE 42

Formation of 4-methyl-2-(2-methylphenyl)-5-(3-morpholin-4-ylpropyl)-1H-pyrazolo[4,3-c]pyridine-3,6(2H,5H)-dione (42) (Compound Ia, Scheme 1)

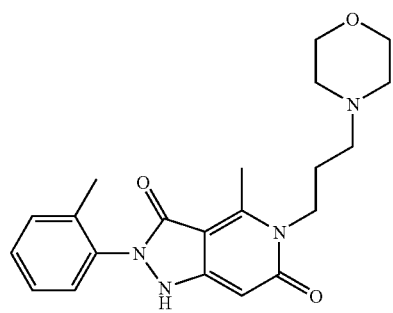 [SMILES: Cc1ccccc1-n1[nH]c2cc(=O)n(CCCN3CCOCC3)c(C)c2c1=O]

Following the general methods as outlined in Example 7a), starting from (2-methylphenyl)hydrazine, dimethyl 3-oxopentanedioate, 1,1,1-triethoxyethane and 3-morpholin-4-yl-propan-1-amine, the title compound (42) was isolated as a beige solid in 72% yield (98% purity by HPLC). MS (ESI$^+$): 383.6; MS (ESI$^-$): 381.5.

EXAMPLE 43

Formation of 2-(1,3-benzothiazol-2-yl)-4-methyl-1-(pyridin-2-ylmethyl)-5-(tetrahydrofuran-2-ylmethyl)-1H-pyrazolo[4,3-c]pyridine-3,6(2H,5H)-dione (43) (Compound Ib, Scheme 1)

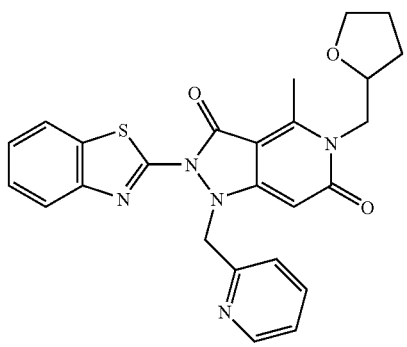 [SMILES: Cc1c2c(=O)n(-c3nc4ccccc4s3)n(Cc3ccccn3)c2cc(=O)n1CC1CCCO1]

Following the general methods as outlined in Examples 7 and 13, starting from 2-hydrazino-1,3-benzothiazole, dimethyl 3-oxopentanedioate, 1,1,1-triethoxyethane, 1-(tetrahydrofuran-2-yl)methanamine and 2-(chloromethyl)pyridine, the title compound (43) was isolated as a beige solid in 60% yield (98% purity by HPLC). MS (ESI$^+$): 474.6; MS (ESI$^-$): 472.5.

EXAMPLE 44

Formation of 2-(1,3-benzothiazol-2-yl)-4-ethyl-5-(pyridin-2-ylmethyl)-1H-pyrazolo[4,3-c]pyridine-3,6(2H,5H)-dione (44) (Compound Ia, Scheme 1)

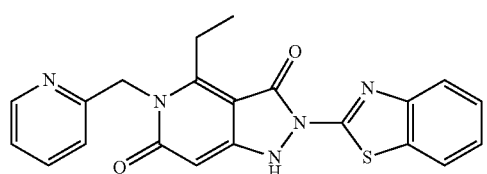

Following the general methods as outlined in Example 7a), starting from 2-hydrazino-1,3-benzothiazole, dimethyl 3-oxopentanedioate, 1,1,1-triethoxypropane and 1-pyridin-2-ylmethanamine, the title compound (44) was isolated as a yellow solid in 83% yield (95% purity by HPLC). MS (ESI$^+$): 404.6; MS (ESI$^-$): 402.5.

EXAMPLE 45

Formation of 2-(1,3-benzothiazol-2-yl)-4-ethyl-5-(3-morpholin-4-ylpropyl)-1H-pyrazolo[4,3-c]pyridine-3,6(2H,5H)-dione (45) (Compound Ia, Scheme 1)

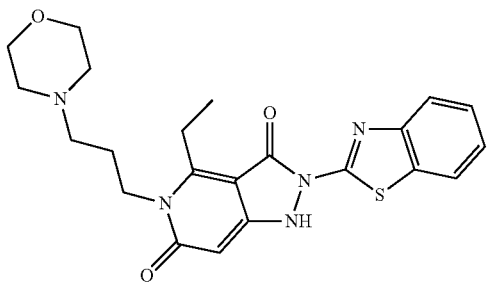 [SMILES: CCc1c2c(=O)n(-c3nc4ccccc4s3)[nH]c2cc(=O)n1CCCN1CCOCC1]

Following the general methods as outlined in Example 7a), starting from 2-hydrazino-1,3-benzothiazole, dimethyl 3-oxopentanedioate, 1,1,1-triethoxypropane and 3-morpholin-4-ylpropan-1-amine, the title compound (45) was isolated as a beige solid in 82% yield (98% purity by HPLC). MS (ESI$^+$): 440.5; MS (ESI$^-$): 438.4.

EXAMPLE 46

Formation of 2-(1,3-benzothiazol-2-yl)-4-ethyl-5-(2-methoxyethyl)-1H-pyrazolo[4,3-c]pyridine-3,6(2H,5H)-dione (46) (Compound Ia, Scheme 1)

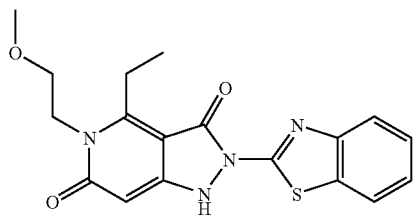 [SMILES: CCc1c2c(=O)n(-c3nc4ccccc4s3)[nH]c2cc(=O)n1CCOC]

Following the general methods as outlined in Example 7a), starting from 2-hydrazino-1,3-benzothiazole, dimethyl 3-oxopentanedioate, 1,1,1-triethoxypropane and 2-methoxyethanamine, the title compound (46) was isolated as a white solid in 69% yield (97% purity by HPLC). MS (ESI$^+$): 371.4; MS (ESI$^-$): 369.4.

EXAMPLE 47

Formation of 2-(1,3-benzothiazol-2-yl)-4-ethyl-5-(4-methylpiperazin-1-yl)-1H-pyrazolo[4,3-c]pyridine-3,6(2H,5H)-dione (47) (Compound Ia, Scheme 1)

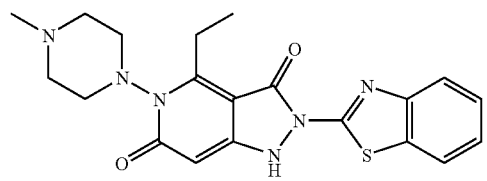 [SMILES: CCc1c2c(=O)n(-c3nc4ccccc4s3)[nH]c2cc(=O)n1N1CCN(C)CC1]

Following the general methods as outlined in Example 7a), starting from 2-hydrazino-1,3-benzothiazole, dimethyl 3-oxopentanedioate, 1,1,1-triethoxypropane and 4-methylpiperazin-1-amine, the title compound (47) was isolated as a beige solid in 78% yield (98% purity by HPLC). MS (ESI$^+$): 411.6; MS (ESI$^-$): 409.4.

EXAMPLE 48

Formation of 2-(1,3-benzothiazol-2-yl)-4-ethyl-5-[1-(4-methylbenzyl)piperidin-4-yl]-1H-pyrazolo[4,3-c]pyridine-3,6(2H,5H)-dione (48) (Compound Ia, Scheme 1)

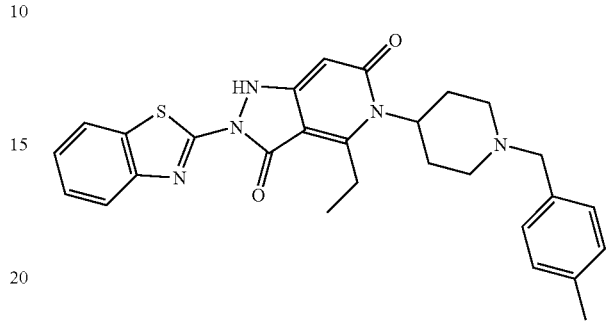

Following the general methods as outlined in Example 7a), starting from 2-hydrazino-1,3-benzothiazole, dimethyl 3-oxopentanedioate, 1,1,1-triethoxypropane and 1-(4-methylbenzyl)piperidin-4-amine, the title compound (48) was isolated as a yellow solid in 55% yield (92% purity by HPLC). MS (ESI$^+$): 500.6; MS (ESI$^-$): 498.6.

EXAMPLE 49

Formation of 4-ethyl-2-(4-fluorophenyl)-5-(pyridin-2-ylmethyl)-1H-pyrazolo[4,3-c]pyridine-3,6(2H,5H)-dione (49) (Compound Ia, Scheme 1)

Following the general methods as outlined in Example 7a), starting from (4-fluorophenyl)hydrazine, dimethyl 3-oxopentanedioate, 1,1,1-triethoxypropane and 1-pyridin-2-ylmethanamine, the title compound (49) was isolated as a yellowish solid in 77% yield (99% purity by HPLC). MS (ESI$^+$): 365.5; MS (ESI$^-$): 363.7.

EXAMPLE 50

Formation of 4-ethyl-2-(4-fluorophenyl)-5-(3-morpholin-4-ylpropyl)-1H-pyrazolo[4,3-c]pyridine-3,6(2H,5H)-dione (50) (Compound Ia, Scheme 1)

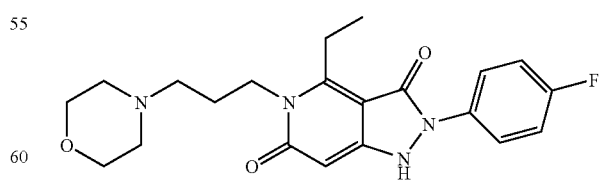

Following the general methods as outlined in Example 7a), starting from (4-fluorophenyl)hydrazine, dimethyl 3-oxopentanedioate, 1,1,1-triethoxypropane and 3-morpholin-4-ylpropan-1-amine, the title compound (50) was isolated as a beige solid in 78% yield (99% purity by HPLC). MS (ESI$^+$): 401.5; MS (ESI$^-$): 399.3.

EXAMPLE 51

Formation of 4-ethyl-2-(4-fluorophenyl)-5-(2-methoxyethyl)-1H-pyrazolo[4,3-c]pyridine-3,6(2H,5H)-dione (51) (Compound Ia, Scheme 1)

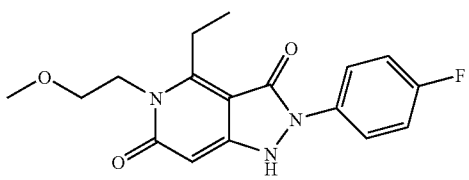 [SMILES: CCc1c2c(=O)n(-c3ccc(F)cc3)[nH]c2cc(=O)n1CCOC]

Following the general methods as outlined in Example 7a), starting from (4-fluorophenyl)hydrazine, dimethyl 3-oxopentanedioate, 1,1,1-triethoxypropane and 2-methoxyethanamine, the title compound (51) was isolated as a white solid in 76% yield (98% purity by HPLC). MS (ESI$^+$): 332.4; MS (ESI$^-$): 330.4.

EXAMPLE 52

Formation of 5-(2-morpholin-4-ylethyl)-2-pyridin-2-yl-1H-pyrazolo[4,3-c]pyridine-3,6(2H,5H)-dione (52) (Compound Ia, Scheme 1)

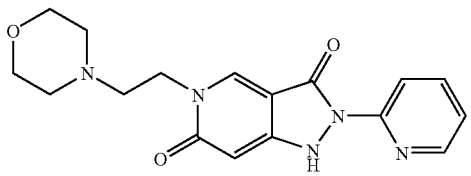 [SMILES: O=c1cc2[nH]n(-c3ccccn3)c(=O)c2cn1CCN1CCOCC1]

Following the general methods as outlined in Example 7a), starting from 2-hydrazinopyridine, dimethyl 3-oxopentanedioate, 1,1,1-triethoxymethane and 2-morpholin-4-ylethanamine, the title compound (52) was isolated as a yellowish solid in 68% yield (97% purity by HPLC). MS (ESI$^+$): 342.5; MS (ESI$^-$): 340.3.

EXAMPLE 53

Formation of 2,4-diphenyl-5-(pyridin-3-ylmethyl)-1H-pyrazolo[4,3-c]pyridine-3,6(2H,5H)-dione (53) (Compound Ia, Scheme 1)

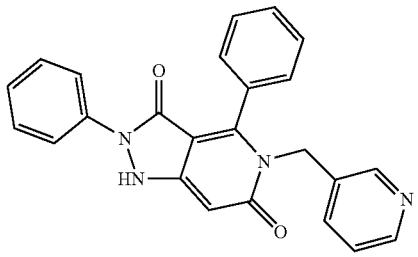 [SMILES: O=c1c2c(-c3ccccc3)n(Cc3cccnc3)c(=O)cc2[nH]n1-c1ccccc1]

Following the general methods as outlined in Example 7a), starting from phenylhydrazine, dimethyl 3-oxopentanedioate, (triethoxymethyl)benzene and 1-pyridin-3-ylmethanamine, the title compound (53) was isolated as a beige solid in 79% yield (96% purity by HPLC). MS (ESI$^+$): 395.5; MS (ESI$^-$): 393.2.

EXAMPLE 54

Formation of 2-(2-chlorophenyl)-4-ethyl-5-(pyridin-3-ylmethyl)-1H-pyrazolo[4,3-c]pyridine-3,6(2H,5H)-dione (54) (Compound Ia, Scheme 1)

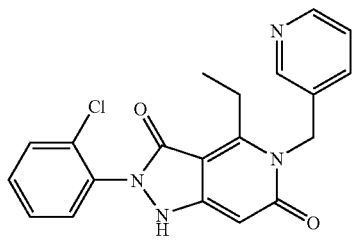 [SMILES: CCc1c2c(=O)n(-c3ccccc3Cl)[nH]c2cc(=O)n1Cc1cccnc1]

Following the general methods as outlined in Example 7a), starting from (2-chlorophenyl)hydrazine, dimethyl 3-oxopentanedioate, 1,1,1-triethoxypropane and 1-pyridin-3-ylmethanamine, the title compound (54) was isolated as a yellow solid in 74% yield (98% purity by HPLC). MS (ESI$^+$): 381.8; MS (ESI$^-$): 379.6.

EXAMPLE 55

Formation of 4-methyl-2-(2-methylphenyl)-5-(pyridin-2-ylmethyl)-1H-pyrazolo[4,3-c]pyridine-3,6(2H,5H)-dione (55) (Compound Ia, Scheme 1)

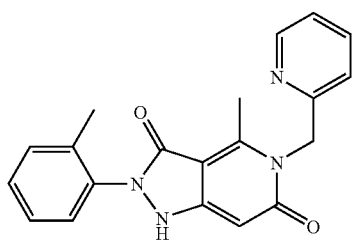 [SMILES: Cc1ccccc1-n1[nH]c2cc(=O)n(Cc3ccccn3)c(C)c2c1=O]

Following the general methods as outlined in Example 7a), starting from (2-methylphenyl)hydrazine, dimethyl 3-oxopentanedioate, 1,1,1-triethoxyethane and 1-pyridin-2-ylmethanamine, the title compound (55) was isolated as a yellow solid in 63% yield (98% purity by HPLC). MS (ESI$^+$): 347.5; MS (ESI$^-$): 345.6.

EXAMPLE 56

Formation of 4-ethyl-5-(3-morpholin-4-ylpropyl)-2-[4-(trifluoromethyl)phenyl]-1H-pyrazolo[4,3-c]pyridine-3,6(2H,5H)-dione (56) (Compound Ia, Scheme 1)

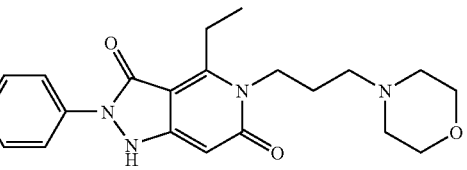

Following the general methods as outlined in Example 7a), starting from [4-(trifluoromethyl)phenyl]hydrazine, dimethyl 3-oxopentanedioate, 1,1,1-triethoxypropane and 3-morpholin-4-ylpropan-1-amine, the title compound (56) was isolated as a yellow solid in 59% yield (96% purity by HPLC). MS (ESI$^+$): 451.5; MS (ESI$^-$): 449.4.

EXAMPLE 57

Formation of 4-ethyl-5-(3-morpholin-4-ylpropyl)-2-[4-(trifluoromethoxy)phenyl]-1H-pyrazolo[4,3-c]pyridine-3,6(2H,5H)-dione (57) (Compound Ia, Scheme 1)

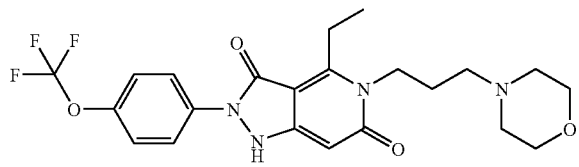 [SMILES: CCc1c2c(=O)n(-c3ccc(OC(F)(F)F)cc3)[nH]c2cc(=O)n1CCCN1CCOCC1]

Following the general methods as outlined in Example 7a), starting from [4-(trifluoromethoxy)phenyl]hydrazine, dimethyl 3-oxopentanedioate, 1,1,1-triethoxypropane and 3-morpholin-4-ylpropan-1-amine, the title compound (57) was isolated as a yellow solid in 67% yield (97% purity by HPLC). MS (ESI$^+$): 467.4; MS (ESI$^-$): 465.6.

EXAMPLE 58

Formation of 2-(2,5-difluorophenyl)-4-ethyl-5-(3-morpholin-4-ylpropyl)-1H-pyrazolo[4,3-c]pyridine-3,6(2H,5H)-dione (58) (Compound Ia, Scheme 1)

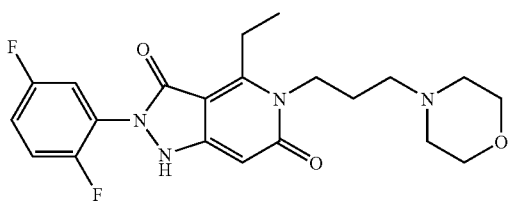 [SMILES: CCc1c2c(=O)n(-c3cc(F)ccc3F)[nH]c2cc(=O)n1CCCN1CCOCC1]

Following the general methods as outlined in Example 7a), starting from (2,5-difluorophenyl)hydrazine, dimethyl 3-oxopentanedioate, 1,1,1-triethoxypropane and 3-morpholin-4-ylpropan-1-amine, the title compound (58) was isolated as a yellow solid in 71% yield (98% purity by HPLC). MS (ESI$^+$): 419.7; MS (ESI$^-$): 417.3.

EXAMPLE 59

Formation of 4-ethyl-2-(2-methoxyphenyl)-5-(3-morpholin-4-ylpropyl)-1H-pyrazolo[4,3-c]pyridine-3,6(2H,5H)-dione (59) (Compound Ia, Scheme 1)

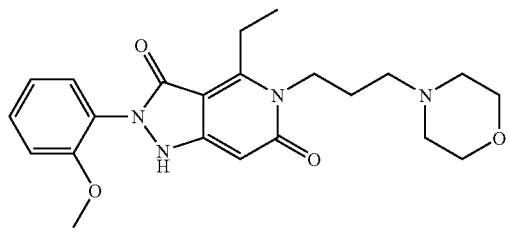 [SMILES: CCc1c2c(=O)n(-c3ccccc3OC)[nH]c2cc(=O)n1CCCN1CCOCC1]

Following the general methods as outlined in Example 7a), starting from (2-methoxyphenyl)hydrazine, dimethyl 3-oxopentanedioate, 1,1,1-triethoxypropane and 3-morpholin-4-ylpropan-1-amine, the title compound (59) was isolated as a yellowish solid in 67% yield (99% purity by HPLC). MS (ESI$^+$): 413.6; MS (ESI$^-$): 411.7.

EXAMPLE 60

Measurement of Levels of Reactive Oxygen Species in Different Cell Cultures

The activity of the compounds according to the invention may be tested for their activity in the inhibition or reduction of formation of reactive oxygen species (ROS) from oxygen in cells. The activity of the compounds is tested in the following cell cultures by different techniques such as nitroblue tetrazolium, Amplex Red, Chemiluminescence (Luminol) and 2',7'-dichlorodihydrofluorescein diacetate (H$_2$DCF-DA) according to the protocols detailed below.

Human Microglia Cell Line

Human microglia cell line (HMC3, human microglia clone 3) (Janabi et al, 1995, *Neurosci Lett* 195:105) were cultured in MEM (Eagle's minimum essential medium) containing 10% FBS with 50 U/ml penicillin G sodium 50 µg/ml streptomycin sulfate, and incubated at 37° C. for 24 hours. IFN-γ (human IFN-γ, Roche. 11 040 596 001) was added to the culture medium for a final concentration of 10 ng/ml 24 h, before detection of O$_2^-$ formation.

Human Umbilical Vein Endothelial Cells (HUVEC)

HUVEC are cultured in endothelial basal medium supplemented with hydrocortisone (1 µg/mL, CalbioChem), bovine brain extract (12 µg/mL), gentamicin (50 µg/mL, CalbioChem), amphotericin B (50 ng/mL, CalBioChem EGF (10 ng/mL, and 10% FCS until the fourth passage. When the fifth passage was started, cells were cultured with a lower concentration of FCS (2%) in the absence of EGF, if not indicated otherwise. All experiments were done with cells of the fifth passage. The cells were incubated with OxLDL (oxidized low-density lipoprotein) or its buffer as control for 24 h, before detection of O$_2^-$ formation.

HL-60 Cells

Human acute myeloid leukemia cell line HL-60 was cultured in RPMI 1640 (Invitrogen) supplemented with 10% heat-inactivated calf serum, 2 mM glutamine, 100 U/mL penicillin (Sigma), and 100 µg streptomycin (Sigma) at 37° C. under a humidified atmosphere of 5% CO$_2$. HL60 differentiation to the neutrophil phenotype was triggered by adding Me$_2$SO (final concentration 1.25% v/v for 6 days) to the culture medium.

1. Nitroblue Tetrazolium (NBT)

Intracellular and extracellular superoxide was measured by a colorimetric technique using a quantitative nitroblue tetrazolium (NBT) test. SOD-inhibitable conversion of NBT to formazan, a fine blue precipitate, in the presence of superoxide anion was measured using Fluostar Optima spectrometer (BMG labtech). Following incubation with appropriate stimuli, cells were trypsinized (1× Trypsin-EDTA), collected by centrifugation, and washed with PBS to remove medium. 5×10$^5$ cells were plated on 48-well plates and incubated in Hank's balanced salt solution containing 0.5 mg/mL NBT with or without 800 U/mL SOD in the presence or absence of compounds according to the invention. As a control, DPI was included at a final concentration of 10 µM. After 2.5 h, cells were fixed and washed with methanol to remove non reduced NBT. The reduced formazan was then dissolved in 230 µl of 2M potassium hydroxide and in 280 µl of dimethylsulfoxide. The absorption was measured at 630 nm. For calculation, the absorbance at 630 nm was normalized for each individual well. The mean of the four blank values was subtracted from each corrected value for each time point. NOX activities were expressed as % of the activity in control cells. Residual activity of DPI-treated cells was usually <10%.

2. Amplex Red

Extracellular hydrogen peroxide was measured using Amplex UltraRed (Molecular Probes). Cells were trypsinized (1× Trypsin-EDTA), collected by centrifugation, and resuspended in HBSS supplemented with 1% glucose. Cells were seeded into black 96-well plates at a density of 50'000 cells in 200 μl testing buffer (HBSS 1% glucose containing 0.005 U/mL horseradish peroxidase (Roche) and 50 μM Amplex Red in the presence or absence of compounds according to the invention. As a control, DPI was included at a final concentration of 10 μM The plates were placed in the fluorescent Optima Fluorescent plate reader and kept at 37° C. during 20 min. Fluorescence was measured for 15 min hours with excitation and emission wavelengths of 544 nm and 590 nm respectively. NOX activities were expressed as % of the activity in control cells. Residual activity of DPI-treated cells was usually <10%.

The Table 1 below summarizes the percentage of inhibition of NOX activity as measured by Amplex Red using DMSO-differentiated HL60 cells as described above:

TABLE 1

| Compound n° | Inhibition (%) |
|---|---|
| (1) | 53 |
| (9) | 51 |
| (12) | 60 |

The Table 2 below summarizes the $IC_{50}$ of NOX activity as measured by Amplex Red using DMSO-differentiated HL60 cells as described above:

TABLE 2

| Compound n° | $IC_{50}$ (μM) |
|---|---|
| (1) | 1.1 |
| (9) | 8.4 |
| (10) | 4.0 |
| (12) | 6.4 |
| (14) | 13.8 |
| (21) | 13.4 |
| (23) | 14.5 |
| (30) | 12.9 |
| (31) | 14.5 |
| (36) | 4.3 |
| (44) | 4.3 |
| (46) | 2.7 |
| (53) | 4.4 |

3. Chemiluminescence (Luminol)

ROS was measured using the chemiluminescent probe luminol. Cells were cultured and plated as for Amplex Red except that the Amplex Red agent was replaced by 10 μg/mL luminol (Sigma 09235). Light emission was recorded continuously at 37° C. for 60 minutes using the luminescence function of the FluoStar Optima fluorescent plate reader. The mean of the four blank values was subtracted from each corrected value for each time point. NOX activities were expressed as % of the activity in control cells. Residual activity of DPI-treated cells was usually <10%.

4. 2',7'-dichlorodihydrofluorescein Diacetate ($H_2$DCF-DA)

HUVEC were plated on coverslips and made quiescent overnight in 0.5% BSA before stimulation with TGF-β. Cells were loaded for 10 minutes with 5 μM CM-H2DCFDA in phenol-red-free medium in the dark and then treated with TGF-β (R&D Systems) in the presence or absence of compounds according to the invention. Cells were then visualized by immunofluorescence microscopy after fixation and staining of the nuclei with DAPI or examined live using confocal microscopy. DCF fluorescence was visualized at an excitation wavelength of 488 nm and emission at 515 to 540 nm. To avoid photo-oxidation of the indicator dye, images were collected with a single rapid scan using identical parameters for all samples. For calculation, the absorbance at 540 nm was normalized to absorbance at 540 nm for each individual well. The mean of the four blank values was subtracted from each corrected value for each time point. NOX activities were expressed as % of the activity in control cells. Residual activity of DPI-treated cells was usually <10%.

The invention claimed is:

1. A pharmaceutical composition comprising a pharmaceutically acceptable carrier, diluent or excipient and at least one pyrazolo pyridine derivative according to Formula (I):

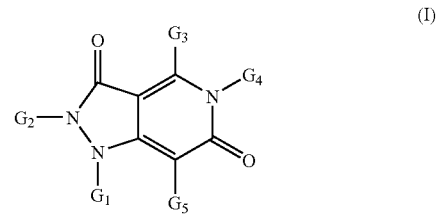

wherein $G_1$ is selected from H, optionally substituted alkyl, optionally substituted $C_3$-$C_8$-cycloalkyl alkyl, optionally substituted heterocycloalkyl alkyl, optionally substituted aryl alkyl and optionally substituted heteroaryl alkyl;

$G_2$ is selected from H, optionally substituted alkyl, optionally substituted alkenyl, optionally substituted alkynyl, optionally substituted aryl, optionally substituted alkyl aryl, optionally substituted aryl alkyl, optionally substituted heteroaryl, optionally substituted alkyl heteroaryl, optionally substituted heteroaryl alkyl, optionally substituted alkenyl aryl, optionally substituted aryl alkenyl, optionally substituted alkenyl heteroaryl, optionally substituted heteroaryl alkenyl, optionally substituted $C_3$-$C_8$-cycloalkyl, optionally substituted heterocycloalkyl, optionally substituted alkyl $C_3$-$C_8$-cycloalkyl, optionally substituted $C_3$-$C_8$-cycloalkyl alkyl, optionally substituted alkyl heterocycloalkyl and optionally substituted heterocycloalkyl alkyl;

$G_3$ is selected from H, optionally substituted alkyl, optionally substituted alkenyl, optionally substituted alkynyl, optionally substituted aryl, optionally substituted alkyl aryl, optionally substituted aryl alkyl, optionally substituted heteroaryl, optionally substituted alkyl heteroaryl, optionally substituted heteroaryl alkyl, optionally substituted alkenyl aryl, optionally substituted aryl alkenyl, optionally substituted alkenyl heteroaryl, optionally substituted heteroaryl alkenyl, optionally substituted $C_3$-$C_8$-cycloalkyl, optionally substituted heterocycloalkyl, optionally substituted alkyl $C_3$-$C_8$-cycloalkyl, optionally substituted $C_3$-$C_8$-cycloalkyl alkyl, optionally substituted alkyl heterocycloalkyl and optionally substituted heterocycloalkyl alkyl;

$G_4$ is selected from H, optionally substituted alkyl, optionally substituted alkenyl, optionally substituted alkynyl, optionally substituted aryl, optionally substituted alkyl aryl, optionally substituted aryl alkyl, optionally substituted heteroaryl, optionally substituted alkyl heteroaryl, optionally substituted heteroaryl alkyl, optionally substituted alkenyl aryl, optionally substituted aryl alkenyl, optionally substituted alkenyl heteroaryl, optionally substituted heteroaryl alkenyl, optionally substituted $C_3$-$C_8$-cycloalkyl, optionally substituted heterocycloalkyl, optionally substituted alkyl $C_3$-$C_8$-cycloalkyl, optionally substituted $C_3$-$C_8$-cycloalkyl alkyl, optionally substituted alkyl heterocycloalkyl and optionally substituted heterocycloalkyl alkyl;

$G_5$ is selected from H, optionally substituted alkyl, optionally substituted alkenyl, optionally substituted alkynyl, optionally substituted aryl, optionally substituted alkyl aryl, optionally substituted aryl alkyl, optionally substituted heteroaryl, optionally substituted alkyl heteroaryl, optionally substituted heteroaryl alkyl, optionally substituted alkenyl aryl, optionally substituted aryl alkenyl, optionally substituted alkenyl heteroaryl, optionally substituted heteroaryl alkenyl, optionally substituted $C_3$-$C_8$-cycloalkyl, optionally substituted heterocycloalkyl, optionally substituted alkyl $C_3$-$C_8$-cycloalkyl, optionally substituted $C_3$-$C_8$-cycloalkyl alkyl, optionally substituted alkyl heterocycloalkyl and optionally substituted heterocycloalkyl alkyl; or pharmaceutically acceptable salts thereof.

2. The pharmaceutical composition according to claim 1, wherein $G_1$ is H.

3. The pharmaceutical composition according to claim 1, wherein $G_1$ is optionally substituted aryl alkyl and optionally substituted heteroaryl alkyl.

4. The pharmaceutical composition according to claim 1, wherein $G_1$ is optionally substituted alkyl.

5. The pharmaceutical composition according to claim 1, wherein $G_2$ is selected from optionally substituted aryl and optionally substituted heteroaryl.

6. The pharmaceutical composition according to claim 1, wherein $G_3$ is H.

7. The pharmaceutical composition according to claim 1, wherein $G_3$ is optionally substituted alkyl.

8. The pharmaceutical composition according to claim 1, wherein $G_3$ is optionally substituted aryl.

9. The pharmaceutical composition according to claim 1, wherein $G_4$ is selected from optionally substituted alkyl, optionally substituted alkenyl and optionally substituted alkynyl.

10. The pharmaceutical composition according to claim 1, wherein $G_4$ is selected from optionally substituted aryl alkyl and optionally substituted heteroaryl alkyl.

11. The pharmaceutical composition according to claim 1, wherein $G_4$ is selected from optionally substituted heterocycloalkyl alkyl and optionally substituted $C_3$-$C_8$-cycloalkyl alkyl.

12. The pharmaceutical composition according to claim 1, wherein $G_4$ is optionally substituted heterocycloalkyl.

13. The pharmaceutical composition according to claim 1, wherein $G_5$ is H.

14. The pharmaceutical composition according to claim 1, wherein the pyrazolo pyridine derivative is selected from the following group:
    4-methyl-2-phenyl-5-(thiophen-2-ylmethyl)-1H-pyrazolo [4,3-c]pyridine-3,6(2H.5H)-dione;
    2-(1,3-benzothiazol-2-yl)-5-[2-(1H-imidazol-4-yl)ethyl]-4-methyl-1H-pyrazolo[4,3-c]pyridine-3,6(2H,5H)-dione;
    2-(1,3-benzothiazol-2-yl)-5-[2-(1H-indol-3-yl)ethyl]-4-methyl-1H-pyrazolo[4,3-c]pyridine-3,6(2H,5H)-dione;
    2-(1,3-benzothiazol-2-yl)-4-methyl-5-(3-morpholin-4-yl-propyl)-1H-pyrazolo[4,3-c]pyridine-3,6(2H,5H)-dione;
    5-(furan-2-ylmethyl)-4-methyl-2-phenyl-1H-pyrazolo[4,3-c]pyridine-3,6(2H,5H)-dione;
    4-{[2-(1,3-benzothiazol-2-yl)-4-methyl-3,6-dioxo-1,2,3,6-tetrahydro-5H-pyrazolo [4,3-c]pyridin-5-yl]methyl}benzoic acid;
    4-methyl-2-phenyl-5-(pyridin-3-ylmethyl)-1H-pyrazolo [4,3-c]pyridine-3,6(2H,5H)-dione;
    4-methyl-2-phenyl-5-(2-phenylethyl)-1H-pyrazolo[4,3-c]pyridine-3,6(2H,5H)-dione;
    5-[2-(4-acetylpiperazin-1-ypethyl]-2-(1,3-benzothiazol-2-yl)-4-methyl-1H-pyrazolo [4,3-c]pyridine-3,6(2H,5H)-dione;
    2-(1,3-benzothiazol-2-yl)-4-methyl-5-(2-methylbutyl)-1H-pyrazolo[4,3-c]pyridine-3,6(2H,5H)-dione;
    2-(1,3-benzothiazol-2-yl)-5-[2-(4-methoxyphenyl)ethyl]-4-methyl-1H-pyrazolo[4,3-c]pyridine-3,6(2H,5H)-dione;
    2-(1,3-benzothiazol-2-yl)-5-[2-(4-hexanoylpiperazin-1-yl)ethyl]-4-methyl-1H-pyrazolo [4,3-c]pyridine-3,6(2H,5H)-dione;
    2-(1,3-benzothiazol-2-yl)-1-benzyl-5-(furan-2-ylmethyl)-4-methyl-1H-pyrazolo [4,3-c]pyridine-3,6(2H,5H)-dione;
    5-[2-(1H-indol-3-yl)ethyl]-4-methyl-1-(3-methylbenzyl)-2-phenyl-1H-pyrazolo [4,3-c]pyridine-3,6(2H,5H)-dione;
    1-(4-fluorobenzyl)-5-[2-(1H-indol-3-yl)ethyl]-4-methyl-2-phenyl-1H-pyrazolo [4,3-c]pyridine-3,6(2H,5H)-dione;
    1-(2-chlorobenzyl)-4-methyl-5-[3-(2-oxopyrrolidin-1-yl)propyl]-2-phenyl-1H-pyrazolo [4,3-c]pyridine-3,6(2H,5H)-dione;
    2-(1,3-benzothiazol-2-yl)-1-benzyl-4-methyl-5-(tetrahydrofuran-2-ylmethyl)-1H-pyrazolo [4,3-c]pyridine-3,6(2H,5H)-dione;
    1-(4-chlorobenzyl)-5-[2-(1H-imidazol-4-yl)ethyl]-4-methyl-2-phenyl-1H-pyrazolo [4,3-c]pyridine-3,6(2H,5H)-dione;
    5-(1,3-benzodioxol-5-ylmethyl)-4-methyl-2-phenyl-1H-pyrazolo [4,3-c]pyridine-3,6(2H,5H)-dione;
    5-benzyl-4-methyl-2-phenyl-1H-pyrazolo [4,3-c]pyridine-3,6(2H,5H)-dione;
    5-benzyl-2-(4-fluorophenyl)-4-methyl-1H-pyrazolo [4,3-c]pyridine-3,6(2H,5H)-dione;
    5-benzyl-2-(4-methoxyphenyl)-4-methyl-1H-pyrazolo [4,3-c]pyridine-3,6(2H,5H)-dione;
    2-(1,3-benzothiazol-2-yl)-4-methyl-5-morpholin-4-yl-1H-pyrazolo[4,3-c]pyridine-3,6(2H,5H)-dione;
    5-benzyl-4-methyl-2-(4-nitrophenyl)-1H-pyrazolo [4,3-c]pyridine-3,6(2H, 5H)-dione;
    2-(1,3-benzothiazol-2-yl)-4-methyl-1-(3-methylbenzyl)-5-(3-morpholin-4-ylpropyl)-1H-pyrazolo [4,3-c]pyridine-3,6(2H,5H)-dione;
    2-(1,3-benzothiazol-2-yl)-1-(4-fluorobenzyl)-4-methyl-5-(3-morpholin-4-ylpropyl)-1H-pyrazolo [4,3-c]pyridine-3,6(2H,5H)-dione;
    2-(1,3-benzothiazol-2-yl)-4-methyl-1-(4-methylbenzyl)-5-(3-morpholin-4-ylpropyl)-1H-pyrazolo [4,3-c]pyridine-3,6(2H,5H)-dione;
    2-(1,3-benzothiazol-2-yl)-1-(2-chlorobenzyl)-4-methyl-5-morpholin-4-yl-1H-pyrazolo [4,3-c]pyridine-3,6(2H, 5H)-dione;

2-(1,3-benzothiazol-2-yl)-1-(4-bromobenzyl)-4-methyl-5-(2-morpholin-4-ylethyl)-1H-pyrazolo [4,3-c]pyridine-3,6(2H,5H)-dione;

2-[2-(1,3-benzothiazol-2-yl)-4-methyl-5-(3-morpholin-4-ylpropyl)-3,6-dioxo-2,3,5,6-tetrahydro-1H-pyrazolo[4,3-c]pyridin-1-yl]-N-phenylacetamide;

4-methyl-2-phenyl-5-(tetrahydrofuran-2-ylmethyl)-1H-pyrazolo[4,3-c]pyridine-3,6(2H,5H)-dione;

2-(1,3-benzothiazol-2-yl)-4-methyl-5-(2-phenylethyl)-1H-pyrazolo[4,3-c]pyridine-3,6(2H,5H)-dione;

5-[2-(1H-indol-3-yl)ethyl]-4-methyl-2-phenyl-1H-pyrazolo[4,3-c]pyridine-3,6(2H,5H)-dione;

4-methyl-5-morpholin-4-yl-2-phenyl-1H-pyrazolo[4,3-c]pyridine-3,6(2H,5H)-dione;

2-(1,3-benzothiazol-2-yl)-1-(2-chlorobenzyl)-4-methyl-5-(3-morpholin-4-ylpropyl)-1H-pyrazolo[4,3-c]pyridine-3,6(2H,5H)-dione;

5-benzyl-4-ethyl-2-(4-fluorophenyl)-1H-pyrazolo[4,3-c]pyridine-3,6(2H,5H)-dione;

4-ethyl-2-(4-fluorophenyl)-5-(2-phenylethyl)-1H-pyrazolo[4,3-c]pyridine-3,6(2H,5H)-dione;

4-ethyl-2-(4-fluorophenyl)-5-morpholin-4-yl-1H-pyrazolo[4,3-c]pyridine-3,6(2H,5H)-dione;

4-methyl-5-(2-morpholin-4-ylethyl)-2-phenyl-1H-pyrazolo[4,3-c]pyridine-3,6(2H,5H)-dione;

4-ethyl-5-morpholin-4-yl-2-phenyl-1H-pyrazolo[4,3-c]pyridine-3,6(2H,5H)-dione;

2-(2-chlorophenyl)-4-methyl-5-(pyridin-2-ylmethyl)-1H-pyrazolo[4,3-c]pyridine-3,6(2H,5H)-dione;

4-methyl-2-(2-methylphenyl)-5-(3-morpholin-4-ylpropyl)-1H-pyrazolo[4,3-c]pyridine-3,6(2H,5H)-dione;

2-(1,3-benzothiazol-2-yl)-4-methyl-1-(pyridin-2-ylmethyl)-5-(tetrahydrofuran-2-ylmethyl)-1H-pyrazolo[4,3-c]pyridine-3,6(2H,5H)-dione;

2-(1,3-benzothiazol-2-yl)-4-ethyl-5-(pyridin-2-ylmethyl)-1H-pyrazolo[4,3-c]pyridine-3,6 (2H,5H)-dione;

2-(1,3-benzothiazol-2-yl)-4-ethyl-5-(3-morpholin-4-ylpropyl)-1H-pyrazolo[4,3-c]pyridine-3,6(2H,5H)-dione;

2-(1,3-benzothiazol-2-yl)-4-ethyl-5-(2-methoxyethyl)-1H-pyrazolo[4,3-c]pyridine-3,6(2H,5H)-dione;

2-(1,3-benzothiazol-2-yl)-4-ethyl-5-(4-methylpiperazin-1-yl)-1H-pyrazolo [4,3-c]pyridine-3,6(2H,5H)-dione;

2-(1,3-benzothiazol-2-yl)-4-ethyl-5-[1-(4-methylbenzyl)piperidin-4-yl]-1H-pyrazolo[4,3-c]pyridine-3,6(2H,5H)-dione;

4-ethyl-2-(4-fluorophenyl)-5-(pyridin-2-ylmethyl)-1H-pyrazolo [4,3-c]pyridine-3,6(2H,5H)-dione;

4-ethyl-2-(4-fluorophenyl)-5-(3-morpholin-4-ylpropyl)-1H-pyrazolo[4,3-c]pyridine-3,6 (2H,5H)-dione;

4-ethyl-2-(4-fluorophenyl)-5-(2-methoxyethyl)-1H-pyrazolo[4,3-c]pyridine-3,6(2H,5H)-dione;

5-(2-morpholin-4-ylethyl)-2-pyridin-2-yl-1H-pyrazolo[4,3-c]pyridine-3,6(2H,5H)-dione;

2,4-diphenyl-5-(pyridin-3-ylmethyl)-1H-pyrazolo[4,3-c]pyridine-3,6(2H,5H)-dione;

2-(2-chlorophenyl)-4-ethyl-5-(pyridin-3-ylmethyl)-1H-pyrazolo[4,3-c]pyridine-3,6(2H,5H)-dione;

4-methyl-2-(2-methylphenyl)-5-(pyridin-2-ylmethyl)-1H-pyrazolo[4,3-c]pyridine-3,6(2H,5H)-dione;

4-ethyl-5-(3-morpholin-4-ylpropyl)-2-[4-(trifluoromethyl)phenyl]-1H-pyrazolo[4,3-c]pyridine-3,6(2H,5H)-dione;

4-ethyl-5-(3-morpholin-4-ylpropyl)-2-[4-(trifluoromethoxy)phenyl]-1H-pyrazolo [4,3-c]pyridine-3,6 (2H,5H)-dione;

2-(2,5-difluorophenyl)-4-ethyl-5-(3-morpholin-4-ylpropyl)-1H-pyrazolo[4,3-c]pyridine-3,6 (2H,5H)-dione; or 4-ethyl-2-(2-methoxyphenyl)-5-(3-morpholin-4-ylpropyl)-1H-pyrazolo[4,3-c]pyridine-3,6 (2H,5H)-dione.

15. A method of preparing a pharmaceutical composition comprising combining a pyrazolo pyridine derivative according to claim 1, or pharmaceutically acceptable salts thereof, with a pharmaceutically acceptable carrier, excipient or diluent.

16. A method for the treatment of a patient suffering from disease or condition selected from hypertension, atherosclerosis, pulmonary fibrosis, pulmonary hypertension, Alzheimer's disease, diabetes, asthma, hearing loss and balance problems in response to ototoxic drugs, vascular injuries after balloon surgery, inflammation, cardiovascular complications of Type I or Type II diabetes, intimal hyperplasia, coronary heart disease, cerebral, coronary or arterial vasospasm, endothelial dysfunction, heart failure, peripheral artery disease, restenosis, trauma caused by a stent, stroke, ischemic attack, vascular complications after organ transplantation, viral or bacterial infections, myocardial infarction, platelet aggregation, angina pectoris, aneurysm, aortic dissection, ischemic heart disease, cardiac hypertrophy, pulmonary embolus, thrombotic events, injury caused after ischemia by restoration of blood flow or oxygen delivery in or an transplantation, open heart surgery angioplasty, hemorrhagic shock, angioplasty of ischemic organs, bronchial asthma, bronchitis, allergic rhinitis, adult respiratory syndrome, viral lung infection (influenza), pulmonary hypertension, chronic obstructive pulmonary diseases (COPD), hay fever, obesity, metabolic syndrome, Type II diabetes, soriasis eczema, dermatitis, wound healing, scar formation, osteoporosis, osteoporasis, osteosclerosis, periodontitis, hyperparathyroidism, Huntington's disease, amyotrophic lateral sclerosis, epilepsy, muscular dystrophy, leukoencephalopathies, leukodystrophies, diabetic nephropathy, renal failure, glomerulonephritis, nephrotoxicity of aminoglycosides and platinum compounds, hyperactive bladder, erectile dysfunction, fertility disorders, prostatic hypertrophy, benign prostatic hypertrophy cataracts re-opacification of the lens post cataract surgery, diabetic retinopathy, presbyacusis, tinnitus, Meniere's disease and other balance problems, utriculolithiasis, vestibular migraine, noise induced hearing loss, inflammatory bowel disease, sepsis, septic shock, adult respiratory distress syndrome, pancreatitis, shock induced by trauma, bronchial asthma, allergic rhinitis, rheumatoid arthritis, chronic rheumatoid arthritis, arteriosclerosis, intracerebral hemorrhage, cerebral infarction, cystic fibrosis, stroke, acute bronchitis, chronic bronchitis, acute bronchiolitis, chronic bronchiolitis, osteoarthritis, gout, myelitis, ankylosing spondylitis, Reuter syndrome psoriatic arthritis, spondylarthritis, juvenile arthritis, juvenile ankylosing spondylitis, reactive arthritis, gonococcal arthritis, tuberculous arthritis, viral arthritis, bacterial arthritis, syphilitic arthritis, Lyme disease, polyarteritis nodosa, anaphylactic angiitis, Luegenec granulomatosis, rheumatoid polymyalgia, articular cell rheumatism, calcium crystal deposition arthritis, pseudogout, non-arthritic rheumatism, bursitis, tendosynovitis, epicondyle inflammation (tennis elbow), carpal tunnel syndrome, mixed form of arthritis, neuropathic arthropathy, hemorrhagic arthritis, vascular peliosis, hypertrophic osteoarthropathy, multicentric reticulohistiocytosis, arthritis induced by specific diseases, blood pigmentation, sickle cell disease and other hemoglobin abnormality, hyperlipoproteinemia, dysgammaglobulinemia, hyperparathyroidism, acromegaly, familial Mediterranean fever, Bechet's disease, systemic autoimmune disease erythematosus, multiple sclerosis, Crohn's disease, chronic inflammatory bowel diseases (IBD), liver fibrosis, alcohol induced fibrosis, steatosis, non alcoholic steatohepatitis, pain, prostate cancer, breast cancer, pancreatic cancer or renal cancer comprising administering a composition according to claim 1, to a patient in need of treatment of said disease or condition.

17. The composition according to claim 1, wherein said pyrazolo pyridine derivative has Formula (I):

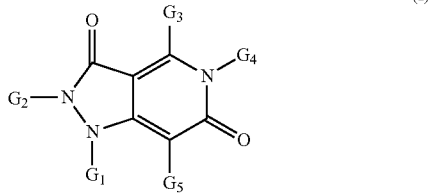

(I)

wherein $G_1$, $G_2$, $G_3$, $G_4$ and $G_5$ are as defined in claim 1, and said derivative is selected from the group consisting of:
5-benzyl-4-ethyl-2-(4-fluorophenyl)-1H-pyrazolo[4,3c]pyridine-3,6(2H,5H)-dione;
4-ethyl-2-(4-fluorophenyl)-5-(2-phenylethyl)-1Hpyrazolo[4,3-c]pyridine-3,6(2,H5H)-dione;
4-ethyl-2-(4-fluorophenyl)-5-morpholin-4-yl-1Hpyrazolo[4,3-c]pyridine-3,6(2,H5H)-dione;
2-(2-chlorophenyl)-4-methyl-5-(pyridin-2-ylmethyl)-1Hpyrazolo[4,3-c]pyridine-3,6(2H,5H)-dione;
4-methyl-2-(2-methylphenyl)-5-(3-morpholin-4-ylpropyl)1H-pyrazolo[4,3-c]pyridine-3,6(2H,5H)-dione;
2-{1,3-benzothiazol-2-yl)-4-methyl-1-(pyridin-2-ylmethyl)5-(tetrahydrofuran-2-ylmethyl)-1H-pyrazolo[4,3-c]pyridine-3,6(2H,5H}-dione;
2-(1,3-benzothiazol-2-yl)-4-ethyl-5-(pyridin-2-ylmethyl)1H-pyrazolo[4,3-c]pyridine-3,6(2H,5H)-dione;
2-(1,3-benzothiazol-2-yl)-4-ethyl-5-(3-morpholin-4yl-propyl)-1H-pyrazolo[4,3-c]pyridine-3,6(2H,5H)-dione;
2-(1,3-benzothiazol-2-yl)-4-ethyl-5-(2-methoxyethyl)-1H-pyrazolo [4,3-c]pyridine-3,6(2H,5H)-dione;
2-(1,3-benzothiazol-2-yl)-4-ethyl-5-(4-methylpiperazin-1yl)-1H-pyrazolo [4,3-c]pyridine-3,6(2H,5H)-dione;
4-ethyl-2-(4-fluorophenyl)-5-(pyridin-2-ylmethyl)-1H-pyrazolo[4,3-c]pyridine-3,6(2H,5H)-dione;
4-ethyl-2-(4-fluorophenyl)-5-(3-morpholin-4-ylpropyl)-1H-pyrazolo[4,3-c]pyridine-3,6(2H,5H)-dione;
4-ethyl-2-(4-fluorophenyl)-5-(2-methoxyethyl)-1H-pyrazolo[4,3-c]pyridine-3,6(2H,5H)-dione;
5-(2-morpholin-4-ylethyl)-2-pyridin-2-yl-1H-pyrazolo[4,3c]pyridine-3,6(2H,5H)-dione;
4-ethyl-5-(3-morpholin-4-ylpropyl)-2-[4-(trifluoromethyl)phenyl)-1H-pyrazolo [4,3-c]pyridine-3,6(2H,5H)-dione;
4-ethyl-5-(3-morpholin-4-ylpropyl)-2-[4-(trifluoromethoxy)phenyl)-1H-pyrazolo[4,3-c]pyridine-3,6(2H,-5H)-dione; or
2-(2,5-difluorophenyl)-4-ethyl-5-(3-morpholin-4-ylpropyl)1H-pyrazolo [4,3-c]pyridine-3,6(2H,5H)-dione; and pharmaceutically acceptable salts thereof.

18. The method according to claim 16, wherein said disease or condition is selected from hypertension, atherosclerosis, pulmonary fibrosis, pulmonary hypertension, Alzheimer's disease, diabetes, asthma, hearing loss and balance problems in response to ototoxic drugs, or vascular injuries after balloon surgery.

19. The method according to claim 16, wherein said disease or condition is inflammation.

20. A pyrazolo pyridine derivative selected from the group consisting of:
5-benzyl-4-ethyl-2-(4-fluorophenyl)-1H-pyrazolo[4,3c]pyridine-3,6(2H,5H)-dione;
4-ethyl-2-(4-fluorophenyl)-5-(2-phenylethyl)-1Hpyrazolo[4,3-c]pyridine-3,6(2H,5H)-dione;
4-ethyl-2-(4-fluorophenyl)-5-morpholin-4-yl-1Hpyrazolo[4,3-c]pyridine-3,6(2H,5H)-dione;
2-(2-chlorophenyl)-4-methyl-5-(pyridin-2-ylmethyl)-1Hpyrazolo [4,3-c]pyridine-3,6(2,5H)-dione;
4-methyl-2-(2-methylphenyl)-5-(3-morpholin-4-ylpropyl)1H-pyrazolo [4,3-c]pyridine-3,6(2H,5H)-dione;
2-{1,3-benzothiazol-2-yl)-4-methyl-1-(pyridin-2-ylmethyl)5-(tetrahydrofuran-2-ylmethyl)-1H-pyrazolo[4,3-c]pyridine-3,6(2H,5H}-dione;
2-(1,3-benzothiazol-2-yl)-4-ethyl-5-(pyridin-2-ylmethyl)1H-pyrazolo [4,3-c]pyridine-3,6(2H,5H)-dione;
2-(1,3-benzothiazol-2-yl)-4-ethyl-5-(3-morpholin-4yl-propyl)-1H-pyrazolo [4,3-c]pyridine-3,6(2H,5H)-dione;
2-(1,3-benzothiazol-2-yl)-4-ethyl-5-(2-methoxyethyl)-1H-pyrazolo[4,3-c]pyridine-3,6(2H,5H)-dione;
2-(1,3-benzothiazol-2-yl)-4-ethyl-5-(4-methylpiperazin-1yl)-1H-pyrazolo [4,3-c]pyridine-3,6(2H,5H)-dione;
4-ethyl-2-(4-fluorophenyl)-5-(pyridin-2-ylmethyl)-1H-pyrazolo[4,3-c]pyridine-3,6(2H,5H)-dione;
4-ethyl-2-(4-fluorophenyl)-5-(3-morpholin-4-ylpropyl)-1H-pyrazolo[4,3-c]pyridine-3,6(2H,5H)-dione;
4-ethyl-2-(4-fluorophenyl)-5-(2-methoxyethyl)-1H-pyrazolo[4,3-c]pyridine-3,6(2H,5H)-dione;
5-(2-morpholin-4-ylethyl)-2-pyridin-2-yl-1H-pyrazolo[4,3c]pyridine-3,6(2H,5H)-dione;
4-ethyl-5-(3-morpholin-4-ylpropyl)-2-[4-(trifluoromethyl)phenyl)-1H-pyrazolo [4,3-c]pyridine-3,6(2H,5H)-dione;
4-ethyl-5-(3-morpholin-4-ylpropyl)-2-[4-(trifluoromethoxy)phenyl)-1H-pyrazolo[4,3-c]pyridine-3,6(2H,-5H)-dione;
2-(2,5-difluorophenyl)-4-ethyl-5-(3-morpholin-4-ylpropyl)1H-pyrazolo [4,3-c]pyridine-3,6(2H,5H)-dione; and pharmaceutically acceptable salts thereof.

21. The method according to claim 16, wherein said disease or condition is cardiovascular complications of Type I or Type II diabetes, intimal hyperplasia, coronary heart disease, cerebral, coronary or arterial vasospasm, endothelial dysfunction, heart failure, peripheral artery disease, restenosis, trauma caused by a stent, stroke, ischemic attack, vascular complications after organ transplantation, viral or bacterial infections, myocardial infarction, platelet aggregation, angina pectoris, aneurysm, aortic dissection, ischemic heart disease, cardiac hypertrophy, pulmonary embolus, thrombotic events, injury caused after ischemia by restoration of blood flow or oxygen delivery in organ transplantation, open heart surgery, angioplasty, hemorrhagic shock, or angioplasty of ischemic organs.

22. The method according to claim 16, wherein said disease or condition is bronchial asthma, bronchitis, allergic rhinitis, adult respiratory syndrome, viral lung infection (influenza), pulmonary hypertension or chronic obstructive pulmonary diseases (COPD).

23. The method according to claim 16, wherein said disease or condition is hay fever.

24. The method according to claim 16, wherein said disease or condition is obesity, metabolic syndrome or Type II diabetes.

25. The method according to claim 16, wherein said disease or condition is psoriasis, eczema, dermatitis, wound healing or scar formation.

26. The method according to claim 16, wherein said disease or condition is osteoporosis, osteoporasis, osteosclerosis, periodontitis, or hyperparathyroidism.

27. The method according to claim 16, wherein said disease or condition is Huntington's disease, amyotrophic lateral sclerosis, epilepsy, muscular dystrophy, leukoencephalopathies or leukodystrophies.

28. The method according to claim 16, wherein said disease or condition is diabetic nephropathy, renal failure, glomerulonephritis, nephrotoxicity of aminoglycosides and platinum compounds or hyperactive bladder.

29. The method according to claim 16, wherein said disease or condition is erectile dysfunction, fertility disorders, prostatic hypertrophy or benign prostatic hypertrophy.

30. The method according to claim 16, wherein said disease or condition is cataracts, re-opacification of the lens post cataract surgery, or diabetic retinopathy.

31. The method according to claim 16, wherein said disease or condition presbyacusis, tinnitus, Meniere's disease and other balance problems, utriculolithiasis, vestibular migraine, or noise induced hearing loss.

32. The method according to claim 16, wherein said disease or condition is inflammatory bowel disease, sepsis, septic shock, adult respiratory distress syndrome, pancreatitis, shock induced by trauma, bronchial asthma, allergic rhinitis, rheumatoid arthritis, chronic rheumatoid arthritis, arteriosclerosis, intracerebral hemorrhage, cerebral infarction, cystic fibrosis, stroke, acute bronchitis, chronic bronchitis, acute bronchiolitis, chronic bronchiolitis, osteoarthritis, gout, myelitis, ankylosing spondylitis, Reuter syndrome, psoriatic arthritis, spondylarthritis, juvenile arthritis, juvenile ankylosing spondylitis, reactive arthritis, gonococcal arthritis, tuberculous arthritis, viral arthritis, bacterial arthritis, syphilitic arthritis, Lyme disease, polyarteritis nodosa, anaphylactic angiitis, Luegenec granulomatosis, rheumatoid polymyalgia, articular cell rheumatism, calcium crystal deposition arthritis, pseudogout, non-arthritic rheumatism, bursitis, tendosynovitis, epicondyle inflammation (tennis elbow), carpal tunnel syndrome, mixed form of arthritis, neuropathic arthropathy, hemorrhagic arthritis, vascular peliosis, hypertrophic osteoarthropathy, multicentric reticulohistiocytosis, arthritis induced by specific diseases, blood pigmentation, sickle cell disease and other hemoglobin abnormality, hyperlipoproteinemia, dysgammaglobulinemia, hyperparathyroidism, acromegaly, familial Mediterranean fever, Bechet's disease, systemic autoimmune disease erythematosus, multiple sclerosis, Crohn's disease, or chronic inflammatory bowel diseases (IBD).

33. The method according to claim 16, wherein said disease or condition is liver fibrosis, alcohol induced fibrosis, steatosis or non alcoholic steatohepatitis.

34. The method according to claim 16, wherein said disease or condition is pain.

35. The method according to claim 16, wherein said disease or condition is pancreatic cancer, breast cancer, prostatic carcinoma or renal cell carcinoma.

* * * * *

UNITED STATES PATENT AND TRADEMARK OFFICE
CERTIFICATE OF CORRECTION

PATENT NO.        : 8,389,518 B2
APPLICATION NO.   : 12/532336
DATED             : March 5, 2013
INVENTOR(S)       : Patrick Page et al.

It is certified that error appears in the above-identified patent and that said Letters Patent is hereby corrected as shown below:

Title Page,
Item (75) Inventors, "Patrick Page, Savonni (FR)" should read
--Patrick Page, Saint-Julien-en-Genevois (FR)--.

In the Specifications

Column 1,
Lines 40-41, "(super-oxide anion [.$O_2^-$], hydroxyl [HO.], peroxyl [ROO.], alkoxyl [RO.] and hydroperoxyl [HOO.])" should read
--(super-oxide anion [•$O_2^-$], hydroxyl [HO•], peroxyl [ROO•], alkoxyl [RO•] and hydroperoxyl [HOO•])--.

Column 7,
Line 12, "where R, R and R''" should read --where R, R' and R''--.

Column 9,
Line 7, "from to acid" should read --from two acid--.

Column 10,
Line 59, "disease erythematosus" should read --disease, erythematosus--.

Column 11,
Line 33, "disorders ischemic" should read --disorders, ischemic--.

Column 16,
Lines 66-67, "selected from optionally substituted optionally substituted aryl" should read --selected from optionally substituted aryl--.

Column 17,
Lines 3-4, "$G_4$ is optionally substituted optionally substituted $C_3$-$C_8$-cycloalky" should read --$G_4$ is optionally substituted $C_3$-$C_8$-cycloalkyl--.

Signed and Sealed this
Twenty-seventh Day of August, 2013

Teresa Stanek Rea
*Acting Director of the United States Patent and Trademark Office*

CERTIFICATE OF CORRECTION (continued)

In the Claims

Column 52,
Lines 13-15, "5-[2-(4-acetylpiperazin-1-ypethyl]-2-(1,3-benzothiazol-2-yl)-4-methyl-1H-pyrazolo[4,3-c]pyridine-3,6(2H,5H)-dione;" should read
--5-[2-(4-acetylpiperazin-1-yl)ethyl]-2-(1,3-benzothiazol-2-yl)-4-methyl-1H-pyrazolo[4,3-c]pyridine-3,6(2H,5H)-dione;--.

Column 54,
Line 25, "delivery in or an" should read --delivery in organ--.
Line 31, "soriasis eczema" should read --psoriasis, eczema--.
Line 39, "hypertrophy cataracts" should read --hypertrophy, cataracts,--.
Lines 50-51, "Reuter syndrome psoriatic" should read --Reuter syndrome, psoriatic--.

Column 55,
Lines 25-30, "4-ethyl-2-(4-fluorophenyl)-5-(2-phenylethyl)-1Hpyrazolo[4,3-c]pyridine-3,6(2H,5H)-dione;
    4-ethyl-2-(4-fluorophenyl)-5-morpholin-4-yl-1Hpyrazolo[4,3-c]pyridine-3,6(2,H5H)-dione;
    2-(2-chlorophenyl)-4-methyl-5-(pyridin-2-ylmethyl)-1Hpyrazolo[4,3-c]pyridine-3,6(2H,5H)-dione;"
should read
    --4-ethyl-2-(4-fluorophenyl)-5-(2-phenylethyl)-1H-pyrazolo[4,3-c]pyridine-3,6(2H,5H)-dione;
    4-ethyl-2-(4-fluorophenyl)-5-morpholin-4-yl-1H-pyrazolo[4,3-c]pyridine-3,6(2H,5H)-dione;
    2-(2-chlorophenyl)-4-methyl-5-(pyridin-2-ylmethyl)-1H-pyrazolo[4,3-c]pyridine-3,6(2H,5H)-dione;--.
Lines 59-60, "2-(2,5-difluorophenyl)-4-ethyl-5-(3-morpholin-4-ylpropyl)1H-pyrazolo[4,3-c]pyridine-3,6(2H,5H)-dione" should read
    2-(2,5-difluorophenyl)-4-ethyl-5-(3-morpholin-4-ylpropyl)-1H-pyrazolo[4,3-c]pyridine-3,6(2H,5H)-dione--.

CERTIFICATE OF CORRECTION (continued)
U.S. Pat. No. 8,389,518 B2

Column 56,
Lines 7-14, "4-ethyl-2-(4-fluorophenyl)-5-(2-phenylethyl)-1Hpyrazolo[4,3-c]pyridine-
3,6(2H,5H)-dione;
    4-ethyl-2-(4-fluorophenyl)-5-morpholin-4-yl-1Hpyrazolo[4,3-c]pyridine-
3,6(2H,5H)-dione;
    2-(2-chlorophenyl)-4-methyl-5-(pyridin-2-ylmethyl)-1Hpyrazolo[4,3-c]
pyridine-3,6(2,5H)-dione;
    4-methyl-2-(2-methylphenyl)-5-(3-morpholin-4-ylpropyl)1H-pyrazolo[4,3-c]
pyridine-3,6(2H,5H)-dione;"
should read
    --4-ethyl-2-(4-fluorophenyl)-5-(2-phenylethyl)-1H-pyrazolo[4,3-c]pyridine-
3,6(2H,5H)-dione;
    4-ethyl-2-(4-fluorophenyl)-5-morpholin-4-yl-1H-pyrazolo[4,3-c]pyridine-
3,6(2H,5H)-dione;
    2-(2-chlorophenyl)-4-methyl-5-(pyridin-2-ylmethyl)-1H-pyrazolo[4,3-c]
pyridine-3,6(2H,5H)-dione;
    4-methyl-2-(2-methylphenyl)-5-(3-morpholin-4-ylpropyl)-1H-pyrazolo[4,3-c]
pyridine-3,6(2H,5H)-dione--.
Lines 18-19, "2-(1,3-benzothiazol-2-yl)-4-ethyl-5-(pyridin-2-ylmethyl)1H-pyrazolo[4,3-
c]pyridine-3,6(2H,5H)-dione" should read
    --2-(1,3-benzothiazol-2-yl)-4-ethyl-5-(pyridin-2-ylmethyl)-1H-pyrazolo[4,3-
c]pyridine-3,6(2H,5H)-dione--.

Column 56,
Lines 38-42, "4-ethyl-5-(3-morpholin-4-ylpropyl)-2-[4-(trifluoromethoxy)phenyl]-1H-
pyrazolo[4,3-c]pyridine-3,6(2H,-5H)-dione;
    2-(2,5-difluorophenyl)-4-ethyl-5-(3-morpholin-4-ylpropyl)1H-pyrazolo
[4,3-c]pyridine-3,6(2H,5H)-dione"
should read
    --4-ethyl-5-(3-morpholin-4-ylpropyl)-2-[4-(trifluoromethoxy)phenyl]-1H-
pyrazolo[4,3-c]pyridine-3,6(2H,5H)-dione;
    2-(2,5-difluorophenyl)-4-ethyl-5-(3-morpholin-4-ylpropyl)-1H-pyrazolo
[4,3-c]pyridine-3,6(2H,5H)-dione--.

UNITED STATES PATENT AND TRADEMARK OFFICE
CERTIFICATE OF CORRECTION

| | |
|---|---|
| PATENT NO. | : 8,389,518 B2 |
| APPLICATION NO. | : 12/532336 |
| DATED | : March 5, 2013 |
| INVENTOR(S) | : Patrick Page et al. |

It is certified that error appears in the above-identified patent and that said Letters Patent is hereby corrected as shown below:

Title Page,

Item (75) Inventors, "Patrick Page, Savonni (FR)" should read
--Patrick Page, Saint-Julien-en-Genevois (FR)--.

In the Specifications

Column 1,
Lines 40-41, "(super-oxide anion [.$O_2^-$], hydroxyl [HO.], peroxyl [ROO.], alkoxyl [RO.] and hydroperoxyl [HOO.])" should read --(super-oxide anion [•$O_2^-$], hydroxyl [HO•], peroxyl [ROO•], alkoxyl [RO•] and hydroperoxyl [HOO•])--.

Column 7,
Line 12, "where R, R and R''" should read --where R, R' and R''--.

Column 9,
Line 7, "from to acid" should read --from two acid--.

Column 10,
Line 59, "disease erythematosus" should read --disease, erythematosus--.

Column 11,
Line 33, "disorders ischemic" should read --disorders, ischemic--.

Column 16,
Lines 66-67, "selected from optionally substituted optionally substituted aryl"
should read --selected from optionally substituted aryl--.

This certificate supersedes the Certificate of Correction issued August 27, 2013.

Signed and Sealed this
Eleventh Day of February, 2014

Michelle K. Lee
*Deputy Director of the United States Patent and Trademark Office*

CERTIFICATE OF CORRECTION (continued)
U.S. Pat. No. 8,389,518 B2

Column 17,
Lines 3-4, "G$_4$ is optionally substituted optionally substituted C$_3$-C$_8$-cycloalkyl" should
read --G$_4$ is optionally substituted C$_3$-C$_8$-cycloalkyl--.

In the Claims

Column 52,
Lines 13-15, "5-[2-(4-acetylpiperazin-1-ypethyl]-2-(1,3-benzothiazol-2-yl)-4-methyl-1H-
pyrazolo[4,3-c]pyridine-3,6(2H,5H)-dione;" should read
--5-[2-(4-acetylpiperazin-1-yl)ethyl]-2-(1,3-benzothiazol-2-yl)-4-methyl-
1H-pyrazolo[4,3-c]pyridine-3,6(2H,5H)-dione;--.

Column 54,
Line 25, "delivery in or an" should read --delivery in organ--.
Line 31, "soriasis eczema" should read --psoriasis, eczema--.
Line 39, "hypertrophy cataracts" should read --hypertrophy, cataracts,--.
Lines 50-51, "Reuter syndrome psoriatic" should read --Reuter syndrome, psoriatic--.

Column 55,
Lines 25-30, "4-ethyl-2-(4-fluorophenyl)-5-(2-phenylethyl)-1Hpyrazolo[4,3-c]pyridine-
3,6(2H,5H)-dione;
4-ethyl-2-(4-fluorophenyl)-5-morpholin-4-yl-1Hpyrazolo[4,3-c]pyridine-
3,6(2,H5H)-dione;
2-(2-chlorophenyl)-4-methyl-5-(pyridin-2-ylmethyl)-1Hpyrazolo[4,3-c]
pyridine-3,6(2H,5H)-dione;"
should read
--4-ethyl-2-(4-fluorophenyl)-5-(2-phenylethyl)-1H-pyrazolo[4,3-c]pyridine-
3,6(2H,5H)-dione;
4-ethyl-2-(4-fluorophenyl)-5-morpholin-4-yl-1H-pyrazolo[4,3-c]pyridine-
3,6(2H,5H)-dione;
2-(2-chlorophenyl)-4-methyl-5-(pyridin-2-ylmethyl)-1H-pyrazolo[4,3-c]
pyridine-3,6(2H,5H)-dione;--.
Lines 59-60, "2-(2,5-difluorophenyl)-4-ethyl-5-(3-morpholin-4-ylpropyl)1H-
pyrazolo[4,3-c]pyridine-3,6(2H,5H)-dione" should read
--2-(2,5-difluorophenyl)-4-ethyl-5-(3-morpholin-4-ylpropyl)-1H-
pyrazolo[4,3-c]pyridine-3,6(2H,5H)-dione--.

Column 56,
Lines 7-14, "4-ethyl-2-(4-fluorophenyl)-5-(2-phenylethyl)-1Hpyrazolo[4,3-c]pyridine-
3,6(2H,5H)-dione;
4-ethyl-2-(4-fluorophenyl)-5-morpholin-4-yl-1Hpyrazolo[4,3-c]pyridine-
3,6(2H,5H)-dione;
2-(2-chlorophenyl)-4-methyl-5-(pyridin-2-ylmethyl)-1Hpyrazolo[4,3-c]
pyridine-3,6(2,5H)-dione;
4-methyl-2-(2-methylphenyl)-5-(3-morpholin-4-ylpropyl)1H-pyrazolo[4,3-c]
pyridine-3,6(2H,5H)-dione;"

CERTIFICATE OF CORRECTION (continued)
U.S. Pat. No. 8,389,518 B2 should read
--4-ethyl-2-(4-fluorophenyl)-5-(2-phenylethyl)-1H-pyrazolo[4,3-c]pyridine-3,6(2H,5H)-dione;
4-ethyl-2-(4-fluorophenyl)-5-morpholin-4-yl-1H-pyrazolo[4,3-c]pyridine-3,6(2H,5H)-dione;
2-(2-chlorophenyl)-4-methyl-5-(pyridin-2-ylmethyl)-1H-pyrazolo[4,3-c]pyridine-3,6(2H,5H)-dione;
4-methyl-2-(2-methylphenyl)-5-(3-morpholin-4-ylpropyl)-1H-pyrazolo[4,3-c]pyridine-3,6(2H,5H)-dione;--.

Lines 18-19, "2-(1,3-benzothiazol-2-yl)-4-ethyl-5-(pyridin-2-ylmethyl)1H-pyrazolo[4,3-c]pyridine-3,6(2H,5H)-dione" should read
--2-(1,3-benzothiazol-2-yl)-4-ethyl-5-(pyridin-2-ylmethyl)-1H-pyrazolo[4,3-c]pyridine-3,6(2H,5H)-dione--.

Lines 38-42, "4-ethyl-5-(3-morpholin-4-ylpropyl)-2-[4-(trifluoromethoxy)phenyl]-1H-pyrazolo[4,3-c]pyridine-3,6(2H,-5H)-dione;
2-(2,5-difluorophenyl)-4-ethyl-5-(3-morpholin-4-ylpropyl)1H-pyrazolo[4,3-c]pyridine-3,6(2H,5H)-dione"
should read
--4-ethyl-5-(3-morpholin-4-ylpropyl)-2-[4-(trifluoromethoxy)phenyl]-1H-pyrazolo[4,3-c]pyridine-3,6(2H,5H)-dione;
2-(2,5-difluorophenyl)-4-ethyl-5-(3-morpholin-4-ylpropyl)-1H-pyrazolo[4,3-c]pyridine-3,6(2H,5H)-dione--.